(12) United States Patent
Heil et al.

(10) Patent No.: US 10,993,439 B2
(45) Date of Patent: May 4, 2021

(54) MESOIONIC IMIDAZOPYRIDINES AS INSECTICIDES

(71) Applicant: BAYER AKTIENGESELLSCHAFT, Leverkusen (DE)

(72) Inventors: Markus Heil, Leichlingen (DE); Laura Hoffmeister, Duesseldorf (DE); Matthew Webber, Duesseldorf (DE); Kerstin Ilg, Cologne (DE); Ulrich Goergens, Ratingen (DE); Andreas Turberg, Haan (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 0 days.

(21) Appl. No.: 16/606,126

(22) PCT Filed: Apr. 16, 2018

(86) PCT No.: PCT/EP2018/059662
§ 371 (c)(1),
(2) Date: Jan. 13, 2020

(87) PCT Pub. No.: WO2018/192872
PCT Pub. Date: Oct. 25, 2018

(65) Prior Publication Data
US 2020/0146292 A1 May 14, 2020

(30) Foreign Application Priority Data

Apr. 21, 2017 (EP) .................................. 17167575

(51) Int. Cl.
*A01N 43/90* (2006.01)
*C07D 471/04* (2006.01)

(52) U.S. Cl.
CPC ........... *A01N 43/90* (2013.01); *C07D 471/04* (2013.01)

(58) Field of Classification Search
CPC .............................. A01N 43/90; C07D 471/04
See application file for complete search history.

(56) References Cited

U.S. PATENT DOCUMENTS

| 5,824,687 | A | 10/1998 | Senn-Bilfinger | |
| 8,552,007 | B2* | 10/2013 | Holyoke, Jr. | A61P 33/10 514/259.4 |
| 8,697,707 | B2* | 4/2014 | Holyoke, Jr. | A01N 43/90 514/259.41 |
| 8,722,690 | B2* | 5/2014 | Zhang | C07D 495/14 514/259.41 |
| 9,018,220 | B2* | 4/2015 | Holyoke, Jr. | A61P 33/00 514/259.4 |
| 9,210,932 | B2* | 12/2015 | Zhang | A01N 43/90 |
| 9,314,025 | B2* | 4/2016 | Holyoke, Jr. | A61P 33/00 |
| 9,596,856 | B2* | 3/2017 | Zhang | C07D 417/06 |
| 2010/0323887 | A1 | 12/2010 | Holyoke, Jr. et al. | |
| 2012/0114624 | A1 | 5/2012 | Lahm et al. | |
| 2012/0115722 | A1* | 5/2012 | Holyoke, Jr. | A01N 43/90 504/100 |
| 2012/0122679 | A1* | 5/2012 | Zhang | C07D 513/04 504/100 |
| 2012/0122680 | A1* | 5/2012 | Holyoke, Jr. | C07D 498/04 504/100 |
| 2012/0277100 | A1* | 11/2012 | Zhang | C07D 417/06 504/100 |
| 2013/0338002 | A1 | 12/2013 | Holyoke, Jr. et al. | |
| 2014/0088309 | A1 | 3/2014 | Smith | |
| 2014/0187776 | A1* | 7/2014 | Holyoke, Jr. | A01N 43/90 544/282 |
| 2014/0206536 | A1* | 7/2014 | Zhang | A01N 43/54 504/100 |
| 2014/0221203 | A1 | 8/2014 | Lahm et al. | |
| 2016/0066577 | A1* | 3/2016 | Zhang | A61P 43/00 504/100 |
| 2018/0282323 | A1 | 10/2018 | Heil et al. | |

(Continued)

FOREIGN PATENT DOCUMENTS

| EP | 0695303 B1 | 11/2001 |
| WO | 2009/099929 A1 | 8/2009 |
| WO | 2010/129500 A2 | 11/2010 |

(Continued)

OTHER PUBLICATIONS

Edstrom; J. Org. Chem. 1994, 59, 9, 2473-2481. (Year: 1994).*
Kielland; Chem. Commun., 2012, 48, 7401-7403, with Electronic Supplementary Material S1-S23. (Year: 2012).*
Lawson; J. Chem. Soc., 1959, 2865-2871. (Year: 1959).*
International Search report of International Patent Application No. PCT/EP2018/059662, filed Jun. 21, 2018.
Database Chemical Abstract [Online], 1971, Database accession No. 1971:125564.
Database Chemical Abstract [Online], 1998, Database accession No. 1999:629080.
Database Chemical Abstract [Online], 2011, Database accession No. 2011:1344559.
Database Chemical Abstract [Online], 1977, Database accession No. 1977:6380.

(Continued)

*Primary Examiner* — Daniel R Carcanague
(74) *Attorney, Agent, or Firm* — McBee Moore & Vanik IP, LLC

(57) ABSTRACT

Provided are compounds of the formula (I)

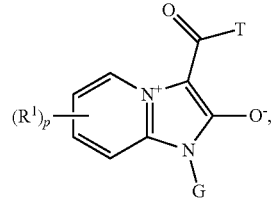

which are suitable for controlling animal pests, including arthropods and in particular insects, arachnids and nematodes, and in which the structural elements $R^1$, p, T and G have the meanings given in the description, as are processes for their preparation and their use as insecticides.

19 Claims, No Drawings

(56) References Cited

U.S. PATENT DOCUMENTS

2020/0037600 A1* 2/2020 Hoffmeister ............ A61P 33/14

FOREIGN PATENT DOCUMENTS

| WO | WO2011017347 | * | 2/2011 | ............ A01N 43/54 |
| WO | 2017/093214 A1 | | 6/2017 | |
| WO | WO-2018108730 A1 | * | 6/2018 | ......... A01N 2300/00 |
| WO | WO-2018189077 A1 | * | 10/2018 | ............ A01M 25/00 |
| WO | WO-2018208595 A1 | * | 11/2018 | ............ A01N 43/90 |
| WO | WO-2018229202 A1 | * | 12/2018 | ........... C07D 487/04 |
| WO | WO-2019086474 A1 | * | 5/2019 | ........... C07D 471/04 |

OTHER PUBLICATIONS

Database Chemical Abstract [Online], 2000, Database accession No. 2000:629434.

Database Chemical Abstract [Online], 1949, Database accession No. 1949:2681.

Newton, Christopher G. et al., "Cyclic Meso-ionic Compounds. Part 22. Meso-ionic Derivatives of the Imidazo[1,2-a] pyridinium System and the Unexpected Synthesis of Stable Pyridinium Dinitromethylides", Journal of the Chemical Society, Perkin Transactions 1, 1984, pp. 69-73.

Cuadro, Ana M. et al., "Synthesis of Highly Stabilised Ylides from N-[2-(1,3-Benzazolylmethyl)] Pyridinium Salts", Tetrahedron, 1990, pp. 6033-6046, vol. 46, No. 17.

Anderson, Wayne K. et al., "Synthesis of 1-Substituted Derivatives of Anhydro(3-chloroacetyl-2-hydroxyimidazo[1,2-α]pyridinium Hydroxide", Canadian Journal of Chemistry, 1971, pp. 668-671, vol. 49.

Guinamant, J.L. et al., "Reaction des dicyanoepoxydes avec les reactifs binucleophiles azotes ou avec leurs halohydrates. Nouvelles syntheses en serie imidazole et imidazole condense", Tetrahedron, 1986, pp. 1169-1177, vol. 42, No. 4.

Lindner, Anika Sabine et al., "Synthesis and properties of imidazo[1,2-α]pyridinium-3-olate. Some revised structures", Tetrahedron, 2009, pp. 7591-7596, vol. 65.

Moody, Christopher J. et al., "Ligand Effects in the Metal Catalysed Reactions of N-Aryldiazoamides: Ylide Formation vs. Insertion Reactions", Tetrahedron, 1998, pp. 9689-9700, vol. 54.

Rybakov, Victor B. et al., "1-Methyl-3-(4-chlorobenzoyl)imidazo-[1,2-a]pyridin-1-ium-2-olate", Acta Crystaliographica, Section E: Structure Reports Online, 2011, 67(10), 2814.

European Search Report of European Patent Application No. 17167575, dated Jul. 14, 2017.

* cited by examiner

MESOIONIC IMIDAZOPYRIDINES AS INSECTICIDES

CROSS-REFERENCE TO RELATED APPLICATIONS

This application is a National Stage entry of International Application No. PCT/EP2018/059662, filed 16 Apr. 2018, which claims priority to European Patent Application No. 17167575.4, filed 21 Apr. 2017.

BACKGROUND

Field

The present invention relates to novel mesoionic imidazopyridine derivatives, to processes for their preparation and to their use for controlling animal pests, especially arthropods and in particular insects, arachnids and nematodes.

Description of Related Art

Certain mesoionic imidazopyridine derivatives are already known, see, for example, J. Chem. Soc. Perkin Trans I, 1984, 69-73; Tetrahedron 1990, 46, 6033-6046; Can. J. Chem. 1971, 49, 668-671; Tetrahedron 1986, 42, 1169-1177; Tetrahedron 2009, 65, 7591-7596; Tetrahedron 1998, 54, 9689-9700; Acta Crystallographica, Section E: Structure Reports Online (2011), 67(10), 2814. No biological action has been described in the publications cited.

SUMMARY

It was an object of the present invention to provide compounds which broaden the spectrum of the pesticides in various aspects and/or improve their activity.

It has now been found that, surprisingly, particular novel mesoionic imidazopyridine derivatives have significant insecticidal properties and are at the same time well tolerated by plants and have favourable homeotherm toxicity and good environmental compatibility. The novel compounds according to the invention have not been disclosed to date.

The present invention therefore provides compounds of the general formula (I)

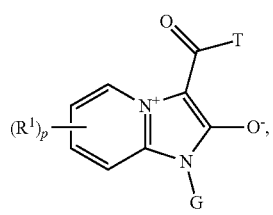

in which (Configuration 1-1):

T represents hydrogen, $C(R^{5a})(R^{5b})(R^{5c})$, $C_2$-$C_8$-alkenyl, $C_3$-$C_8$-alkynyl or $C_3$-$C_8$-cycloalkyl, where $C_2$-$C_8$-alkenyl, $C_3$-$C_8$-alkynyl and $C_3$-$C_8$-cycloalkyl may each optionally be mono- to trisubstituted and the substituents independently of one another are selected from the group consisting of halogen and/or may each optionally be monosubstituted and the substituent is selected from the group consisting of cyano, $C_1$-$C_6$-alkyl, $C_1$-$C_6$-haloalkyl, $C_1$-$C_6$-alkoxy, $C_1$-$C_6$-haloalkoxy, $C_3$-$C_6$-cycloalkyl, $C_1$-$C_6$-alkylthio, $C_1$-$C_6$-alkylsulfinyl, $C_1$-$C_6$-alkylsulfonyl, $C_1$-$C_6$-haloalkylsulfonyl, aryl, hetaryl, aryl-$C_1$-$C_6$-alkyl and hetaryl-$C_1$-$C_6$-alkyl, where aryl, hetaryl, aryl-$C_1$-$C_6$-alkyl and hetaryl-$C_1$-$C_6$-alkyl for their part may each optionally be mono- to trisubstituted and the substituents independently of one another are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy, or T represents aryl, $C_1$-$C_6$-alkylenedioxyaryl, hetaryl, $C_3$-$C_8$-heterocyclyl, $C_3$-$C_8$-oxoheterocyclyl or $C_3$-$C_8$-dioxoheterocyclyl, where the radicals mentioned above may each optionally be mono- to pentasubstituted and the substituents independently of one another are selected from the group consisting of halogen, nitro, amino, cyano, $SF_5$, SCN, $C_1$-$C_6$-alkylamino, di-($C_1$-$C_6$-alkyl)amino, hydroxy, COOH, $C_1$-$C_6$-alkyl, $C_3$-$C_6$-cycloalkyl, $C_3$-$C_6$-heterocyclyl, $C_1$-$C_6$-haloalkyl, $C_1$-$C_6$-alkoxy, $C_1$-$C_6$-haloalkoxy, $C_3$-$C_6$-halocycloalkyl, $C_3$-$C_6$-halocycloalkyl-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, SH, $C_1$-$C_6$-alkylthio, $C_1$-$C_6$-alkylsulfinyl, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, tri-($C_1$-$C_6$-alkyl)silyl, aryl, hetaryl, heterocyclyl, aryl-$C_1$-$C_6$-alkyl and hetaryl-$C_1$-$C_6$-alkyl, where aryl, hetaryl, aryl-$C_1$-$C_6$-alkyl and hetaryl-$C_1$-$C_6$-alkyl for their part may each optionally be mono- to trisubstituted and the substituents independently of one another are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy, or T represents $N(R^{7a})(R^{7b})$ or $N(R^8)$—$N(R^{11a})(R^{11}$ b)

or

T represents $C(=W)R^{12}$ or $C(=O)OR^{13}$,

W represents O or N—$OR^{15}$,

G represents $C_1$-$C_6$-alkyl or $C_2$-$C_6$-alkenyl, where the radicals mentioned above are each mono- to pentasubstituted by halogen and/or mono- to disubstituted by cyano, $C_1$-$C_4$-alkoxy, $C_1$-$C_4$-alkylcarbonyl, $C_1$-$C_4$-alkoxycarbonyl, $C_1$-$C_4$-carbonyl-$C_1$-$C_4$-alkoxy or $C_1$-$C_4$-alkoxyimino-$C_1$-$C_4$-alkyl, $R^1$ in each case represents hydrogen, halogen, cyano, nitro, $SF_5$, SCN, amino, $C_1$-$C_6$-alkylamino, di-($C_1$-$C_6$)-alkylamino, hydroxy, COOH, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_3$-$C_6$-halocycloalkyl-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_2$-$C_6$-alkenyloxy, $C_3$-$C_6$-alkynyl, $C_3$-$C_6$-alkynyloxy, SH, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-haloalkylsulfinyl, $C_1$-$C_6$-haloalkylsulfonyl, $C_1$-$C_6$-alkylcarbonyl, $C_3$-$C_6$-cycloalkylcarbonyl, $C_1$-$C_6$-haloalkylcarbonyl, $C_1$-$C_6$-alkoxyimino-$C_1$-$C_6$-alkyl, $C_1$-$C_6$-alkoxycarbonyl, $C_1$-$C_6$-alkylaminocarbonyl, di-($C_1$-$C_6$)-alkylaminocarbonyl, aryl, hetaryl, aryl-$C_1$-$C_6$-alkyl or hetaryl-$C_1$-$C_6$-alkyl, where aryl, hetaryl, aryl-$C_1$-$C_6$-alkyl and hetaryl-$C_1$-$C_6$-alkyl may each optionally be mono- or polysubstituted and the substituents independently of one another are selected from the group consisting of halogen, cyano, nitro, hydroxy, $C_1$-$C_6$-alkyl, $C_2$-$C_6$-alkenyl, $C_2$-$C_6$- alkynyl, $C_3$-$C_6$-cycloalkyl, $C_1$-$C_6$-alkoxy, $C_1$-$C_6$-haloalkyl, $C_1$-$C_6$-haloalkoxy and $C_1$-$C_6$-alkylthio, or two radicals $R^1$ together form a 5- or 6-membered aliphatic, aromatic, heteroaromatic or heterocyclic ring which may optionally contain 1 to 2 atoms from the group consisting of O, S and N and which may optionally be mono- or polysubstituted, where the substituents independently of one another are selected from the group consisting of halogen and $C_1$-$C_4$-alkyl, p represents 0, 1, 2 or 3, $R^{5a}$ and $R^{5b}$ independently of one another represent hydrogen, halogen, cyano, $C_1$-$C_6$-alkyl, $C_1$-$C_6$-haloalkyl or $C_1$-$C_6$-alkoxy, $R^{5c}$ represents hydrogen, fluorine, chlorine, bromine, cyano, $C_1$-$C_6$-alkoxycarbonyl, $C_1$-$C_6$-alkyl, $C_1$-$C_6$-alkoxy, $C_3$-$C_8$-cycloalkyl, $C_2$-$C_6$-alkenyl or $C_2$-$C_6$-alkynyl, where $C_1$-$C_6$-alkyl, $C_3$-$C_8$-cycloalkyl, $C_2$-$C_6$-alkenyl and $C_2$-$C_6$-alkynyl may each optionally be mono- to pentasubstituted and the substituents independently of one another are selected from the group consisting of halogen and/or may each optionally be monosubstituted and the substituent is selected from the group consisting of nitro, cyano, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-haloalkylsulfonyl, $C_1$-$C_6$-alkylcarbonylamino, $C_1$-$C_6$-alkylaminocarbonyl, di-($C_1$-$C_6$-alkyl)aminocarbonyl, $C_1$-$C_6$-alkylcarbonyl, $C_1$-$C_6$-alkoxycarbonyl, $C_1$-$C_6$-alkoxyimino-$C_1$-$C_6$-alkyl, aryl, hetaryl and heterocyclyl, where aryl, hetaryl and heterocyclyl for their part may each optionally be mono- to trisubstituted and the substituents independently of one another are selected from the group consisting of halogen, nitro, cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, $C_1$-$C_6$-alkylcarbonylamino, aryl and hetaryl, where aryl and hetaryl for their part may each optionally be mono- or polysubstituted and the substituents independently of one another are selected from the group consisting of halogen, cyano, nitro, hydroxy, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy and $C_1$-$C_6$-alkylthio, or $R^{5c}$ represents aryl, C-bound hetaryl, N-bound hetaryl, $C_3$-$C_8$-heterocyclyl, $C_3$-$C_8$-oxoheterocyclyl or $C_3$-$C_8$-dioxoheterocyclyl, where the radicals mentioned above may each optionally be mono- to pentasubstituted and the substituents independently of one another are selected from the group consisting of halogen, nitro, amino, cyano, $SF_5$, SCN, $C_1$-$C_6$-alkylamino, di-($C_1$-$C_6$-alkyl)amino, hydroxy, COOH, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_3$-$C_6$-halocycloalkyl-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, SH, $C_1$-$C_6$-alkylthio, $C_1$-$C_6$-alkylsulfinyl, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$-alkyl)aminocarbonyl, $C_1$-$C_6$-alkylcarbonylamino, tri-($C_1$-$C_6$-alkyl)silyl, aryl, hetaryl, heterocyclyl, aryl-$C_1$-$C_6$-alkyl and hetaryl-$C_1$-$C_6$-alkyl, where aryl, hetaryl, aryl-$C_1$-$C_6$-alkyl and hetaryl-$C_1$-$C_6$-alkyl for their part may each optionally be mono- to trisubstituted and the substituents independently of one another are selected from the group consisting of halogen, cyano, nitro, hydroxy, $C_1$-$C_6$-alkyl, $C_2$-$C_6$-alkenyl, $C_2$-$C_6$-alkynyl, $C_1$-$C_6$-haloalkyl, $C_1$-$C_6$-alkoxy and $C_1$-$C_6$-haloalkoxy or $C_1$-$C_6$-alkylthio, $R^{13}$ and $R^{15}$ independently of one another represent hydrogen, or represent $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, heterocyclyl, heterocyclyl-$C_1$-$C_6$-alkyl, aryl, hetaryl, aryl-$C_1$-$C_6$-alkyl or hetaryl-$C_1$-$C_6$-alkyl, $C_3$-$C_6$-oxoheterocyclyl or $C_3$-$C_6$-dioxoheterocyclyl, where the radicals mentioned above may each optionally be mono- to trisubstituted and the substituents independently of one another are selected from the group consisting of halogen, and/or may each optionally be monosubstituted and the substituent is selected from the group consisting of nitro, cyano, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, $C_1$-$C_6$-alkylcarbonyl, $C_1$-$C_6$-alkoxyimino-$C_1$-$C_6$-alkyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, aryl and hetaryl, where aryl and hetaryl for their part may each optionally be mono- to trisubstituted and the substituents independently of one another are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy, $R^{7a}$ and $R^{11a}$ independently of one another represent hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy, $C_1$-$C_4$-alkoxy-$C_1$-$C_6$-alkyl, $C_1$-$C_6$-alkoxycarbonyl, $C_1$-$C_6$-alkylcarbonyl or $C_1$-$C_6$-alkylsulfonyl, $R^{7b}$ and $R^{11b}$ independently of one another represent hydrogen, $C_1$-$C_6$-alkyl, $C_2$-$C_6$-alkenyl, $C_2$-$C_6$-alkynyl, $C_3$-$C_6$-cycloalkyl or $C_3$-$C_6$-heterocyclyl, where $C_1$-$C_6$-alkyl, $C_2$-$C_6$-alkenyl, $C_2$-$C_6$-alkynyl, $C_3$-$C_6$-cycloalkyl and $C_3$-$C_6$-heterocyclyl may each optionally be mono- to pentasubstituted and the substituents independently of one another are selected from the group consisting of halogen, and/or may each optionally be monosubstituted and the substituent is selected from the group consisting of nitro, cyano, hydroxy, $C_3$-$C_6$-cycloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, aryl, hetaryl, heterocyclyl and oxoheterocyclyl, where aryl, $C_3$-$C_6$-cycloalkyl, hetaryl, heterocyclyl and oxoheterocyclyl for their part may each optionally be mono- to trisubstituted and the substituents independently of one another are selected from the group consisting of halogen, nitro, cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$- alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, $C_1$-$C_6$-alkylcarbonylamino, aryl and hetaryl, where aryl and hetaryl for their part may each optionally be mono- or polysubstituted and the substituents independently of one another are selected from the group consisting of halogen, cyano, nitro, hydroxy, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy and $C_1$-$C_6$-alkylthio, or $R^{7b}$ and $R^{11b}$ independently of one another represent aryl or hetaryl, where the radicals mentioned above may each optionally be mono- to trisubstituted and the substituents independently of one another are selected from the group consisting of halogen, nitro, amino, cyano, $SF_5$, SCN, $C_1$-$C_6$-alkylamino, di-($C_1$-$C_6$)-alkylamino, hydroxy, COOH, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_3$-$C_6$-halocycloalkyl-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, SH, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfinyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl and tri-($C_1$-$C_6$-alkyl)silyl, or $R^{7a}$ and $R^{7b}$ may be attached to one another via two to six carbon atoms and form a ring which may optionally additionally contain a further atom from the group consisting of O, S and N and which may optionally be mono- to tetrasubstituted and where the substituents independently of one another are selected from the group consisting of $C_1$-$C_2$-alkyl, halogen, cyano, amino and $C_1$-$C_2$-alkoxy, or $R^{11a}$ and $R^{11b}$ may be attached to one another via two to six carbon atoms and form a ring which may optionally additionally contain a further atom from the group consisting of O, S and N and which may optionally be mono- to tetrasubstituted and where the substituents independently of one another are selected from the group consisting of $C_1$-$C_2$-alkyl, halogen, cyano, amino and $C_1$-$C_2$-alkoxy, or $R^8$ represents hydrogen, $C_1$-$C_6$-alkyl, $C_2$-$C_6$-alkenyl, $C_2$-$C_6$-alkynyl, $C_3$-$C_6$-cycloalkyl, $C_1$-$C_4$-alkoxy-$C_1$-$C_6$-alkyl, $C_1$-$C_6$-alkoxycarbonyl or $C_1$-$C_6$-alkylcarbonyl, and $R^{12}$ represents hydrogen, $C_1$-$C_6$-alkyl, $C_2$-$C_6$-alkenyl, $C_2$-$C_6$-alkynyl, $C_3$-$C_6$-cycloalkyl or $C_3$-$C_6$-heterocyclyl, where $C_1$-$C_6$-alkyl, $C_2$-$C_6$-alkenyl, $C_2$-$C_6$-alkynyl, $C_3$-$C_6$-cycloalkyl and $C_3$-$C_6$-heterocyclyl may each optionally be mono- to pentasubstituted and the substituents independently of one another are selected from the group consisting of halogen, and/or may each optionally be monosubstituted and the substituent is selected from the group consisting of nitro, cyano, $C_3$-$C_6$-cycloalkyl, $C_1$-$C_6$-alkoxy, $C_1$-$C_6$-haloalkoxy, $C_1$-$C_6$-alkylthio, $C_1$-$C_6$-alkylsulfinyl, $C_1$-$C_6$-alkylsulfonyl, aryl, hetaryl, heterocyclyl and oxoheterocyclyl, where aryl, hetaryl, heterocyclyl and oxoheterocyclyl for their part may each optionally be mono- to trisubstituted and the substituents independently of one another are selected from the group consisting of halogen, nitro, cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl, $C_1$-$C_6$-alkylcarbonylamino, aryl and hetaryl, where aryl and hetaryl for their part may each optionally be mono- or polysubstituted and the substituents independently of one another are selected from the group consisting of halogen, cyano, nitro, hydroxy, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy and $C_1$-$C_6$-alkylthio, or $R^{12}$ represents aryl or hetaryl, where the radicals mentioned above may each optionally be mono- to trisubstituted and the substituents independently of one another are selected from the group consisting of halogen, nitro, amino, cyano, $SF_5$, SCN, $C_1$-$C_6$-alkylamino, di-($C_1$-$C_6$)-alkylamino, hydroxy, COOH, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_3$-$C_6$-halocycloalkyl-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, SH, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfinyl, $C_1$-$C_6$-alkylsulfonyl, $C_1$-$C_6$-haloalkylsulfonyl, $C_1$-$C_6$-alkylaminocarbonyl, di-($C_1$-$C_6$)-alkylaminocarbonyl and tri-($C_1$-$C_6$-alkyl)silyl.

The compounds of the formula (I) likewise encompass any diastereomers or enantiomers and E/Z isomers which exist, and also salts and N-oxides of compounds of the formula (I), and the use thereof for control of animal pests.

DETAILED DESCRIPTION OF A PREFERRED EMBODIMENT

The substituted mesoionic imidazole derivatives are defined in general terms by the formula (I). Preferred radical definitions for the formulae specified above and hereinafter are given below.

Preference (Configuration 2-1) is given to the compounds of the formula (I) in which T represents hydrogen, $C(R^{5a})(R^{5b})(R^{5c})$, $C_2$-$C_6$-alkenyl, $C_3$-$C_6$-alkynyl or $C_3$-$C_6$-cycloalkyl, where $C_2$-$C_6$-alkenyl, $C_3$-$C_6$-alkynyl and $C_3$-$C_6$-cycloalkyl may each optionally be mono- to trisubstituted and the substituents independently of one another are selected from the group consisting of halogen, and/or may each optionally be monosubstituted and the substituent is selected from the group consisting of cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylsulfinyl and $C_1$-$C_4$-alkylsulfonyl, or T represents aryl, $C_1$-$C_6$-alkylenedioxyphenyl, hetaryl or $C_3$-$C_6$-heterocyclyl, where the radicals mentioned above may each optionally be mono- to pentasubstituted and the substituents independently of one another are selected from the group consisting of halogen, nitro, cyano, $C_1$-$C_4$-alkyl, $C_3$-$C_6$-heterocyclyl, $C_1$-$C_4$-haloalkyl, $C_1$-$C_4$-alkoxy, $C_1$-$C_4$-haloalkoxy, $C_2$-$C_4$-alkenyl, $C_3$-$C_4$-alkynyl, $C_1$-$C_4$-alkylthio, $C_1$-$C_4$-alkylsulfinyl, $C_1$-$C_4$-alkylcarbonyl, $C_3$-$C_6$-cycloalkylcarbonyl, $C_2$-$C_4$-alkenylcarbonyl, $C_1$-$C_4$-haloalkylcarbonyl, $C_1$-$C_4$-alkoxycarbonyl, $C_1$-$C_4$-alkylsulfonyl, $C_1$-$C_4$-haloalkylsulfonyl, aryl, hetaryl, heterocyclyl, aryl-$C_1$-$C_6$-alkyl and hetaryl-$C_1$-$C_6$-alkyl, where aryl, hetaryl, aryl-$C_1$-$C_6$-alkyl and hetaryl-$C_1$-$C_6$-alkyl for their part may each be mono- to trisubstituted and the substituents independently of one another are selected from the group consisting of halogen, cyano, $C_1$-$C_4$-alkyl, $C_1$-$C_4$-haloalkyl, $C_1$-$C_4$-alkoxy and $C_1$-$C_4$-haloalkoxy,
or T represents $N(R^{7a})(R^{7b})$ or $N(R^8)$—$N(R^{11a})(R^{11b})$,
or T represents $C(=W)R^{12}$ or $C(=O)OR^{13}$, W represents O or N—$OR^{15}$, G represents $C_1$-$C_6$-alkyl or $C_2$-$C_6$-alkenyl, where the radicals mentioned above are each mono- to pentasubstituted by halogen and/or mono- to disubstituted by cyano, $C_1$-$C_4$-alkoxy, $C_1$-$C_4$-alkylcarbonyl, $C_1$-$C_4$-alkoxycarbonyl, $C_1$-$C_4$-carbonyl-$C_1$-$C_4$-alkoxy, $C_1$-$C_4$-alkoxyimino-$C_1$-$C_4$-alkyl, $R^1$ represents hydrogen, halogen, cyano, $C_1$-$C_4$-alkyl, $C_1$-$C_4$-haloalkyl, $C_1$-$C_4$-alkoxy or $C_1$-$C_4$-haloalkoxy, p represents 1 or 2, $R^{5a}$ and $R^{5b}$ independently of one another represent hydrogen, halogen, cyano, $C_1$-$C_4$-alkyl, $C_1$-$C_4$-haloalkyl or $C_1$-$C_4$-alkoxy, $R^{5c}$ represents hydrogen, fluorine, chlorine, bromine, cyano, $C_1$-$C_4$-alkoxycarbonyl, $C_1$-$C_4$-alkyl, $C_1$-$C_4$-alkoxy, $C_3$-$C_6$-cycloalkyl, $C_2$-$C_6$-alkenyl or $C_2$-$C_6$-alkynyl, where $C_1$-$C_4$-alkyl, $C_3$-$C_6$-cycloalkyl, $C_2$-$C_6$-alkenyl and $C_2$-$C_6$-alkynyl may each optionally be mono- to pentasubstituted and the substituents independently of one another are selected from the group consisting of halogen, and/or may each optionally be monosubstituted and the substituent is selected from the group consisting of nitro, cyano, $C_1$-$C_4$-haloalkyl, $C_1$-$C_4$-alkoxy, $C_1$-$C_4$-haloalkoxy, $C_1$-$C_4$-alkylcarbonyl and $C_1$-$C_4$-alkoxycarbonyl,
or $R^{5c}$ represents aryl or C-bound hetaryl, where the radicals mentioned above may each optionally be mono- to pentasubstituted and the substituents independently of one another are selected from the group consisting of halogen, nitro, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxycarbonyl, $C_1$-$C_4$-alkylthio, $C_1$-$C_4$-alkylsulfinyl and $C_1$-$C_4$-alkylsulfonyl,
or $R^{5c}$ represents Y, Y represents one of the radicals Y-1 to Y-23,

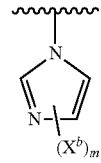

Y-1

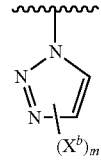

Y-2

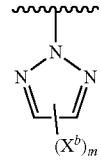

Y-3

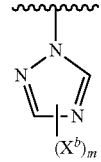

Y-4

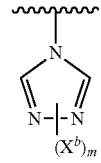

Y-5

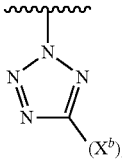

Y-6

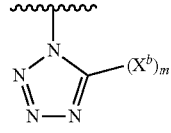

Y-7

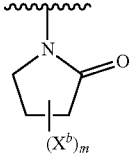

Y-8

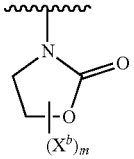

Y-9

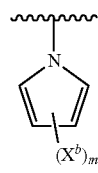

Y-10

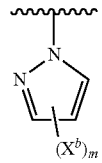

Y-11

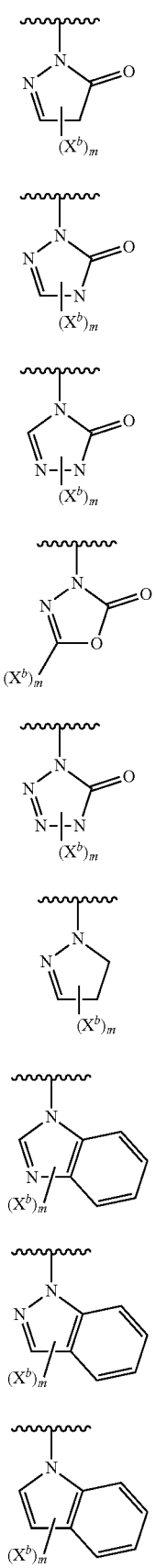

$X^b$ represents halogen, nitro, cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-alkylsulfinyl, $C_1$-$C_6$-haloalkylsulfonyl, $C_1$-$C_6$-alkylaminocarbonyl, di-($C_1$-$C_6$)-alkylaminocarbonyl, $C_1$-$C_6$-alkylcarbonylamino, aryl or hetaryl, where aryl and hetaryl for their part may each optionally be mono- to trisubstituted and the substituents independently of one another are selected from the group consisting of halogen, cyano, nitro, hydroxy, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy and $C_1$-$C_6$-alkylthio and where the ring nitrogen atoms in Y-13, Y-14 and Y-16 are not substituted by halogen, nitro, cyano, $C_1$-$C_4$-alkoxy, $C_1$-$C_4$-haloalkoxy or $C_1$-$C_4$-alkoxy-$C_1$-$C_4$-alkyloxy, m represents 0, 1 or 2, $R^{13}$ and $R^{15}$ independently of one another represent hydrogen, or represent $C_1$-$C_4$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl, $C_3$-$C_6$-heterocyclyl, $C_3$-$C_6$-heterocyclyl-$C_1$-$C_4$-alkyl, $C_3$-$C_6$-oxoheterocyclyl, $C_3$-$C_6$-dioxoheterocyclyl, phenyl, pyridyl, phenyl-$C_1$-$C_4$-alkyl or pyridyl-$C_1$-$C_4$-alkyl, where the radicals mentioned above may each optionally be mono- to trisubstituted and the substituents independently of one another are selected from the group consisting of halogen, and/or may each optionally be monosubstituted and the substituent is selected from the group consisting of nitro, cyano, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkoxycarbonyl, aryl and hetaryl, where aryl and hetaryl for their part may each optionally be mono- to trisubstituted and the substituents independently of one another are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy, $R^{7a}$ and $R^{11a}$ independently of one another represent hydrogen, $C_1$-$C_4$-alkyl, $C_1$-$C_4$-alkoxy, $C_1$-$C_4$-alkoxy-$C_1$-$C_4$-alkyl, $C_1$-$C_4$-alkoxycarbonyl or $C_1$-$C_6$-alkylcarbonyl, $R^{7b}$ and $R^{11b}$ independently of one another represent hydrogen, or independently of one another represent $C_1$-$C_6$-alkyl to $C_3$-$C_6$-cycloalkyl, where the radicals mentioned above may each optionally be mono- to trisubstituted and the substituents independently of one another are selected from the group consisting of halogen, and/or may optionally be monosubstituted and the substituent is selected from the group consisting of cyano, nitro, hydroxy and $C_1$-$C_4$-alkoxy, $C_3$-$C_6$-cycloalkyl, aryl and hetaryl, where aryl, $C_3$-$C_6$-cycloalkyl and hetaryl for their part may be mono- to trisubstituted and the substituents independently of one another are selected from the group consisting of halogen, nitro, cyano, $C_1$-$C_4$-alkyl, $C_1$-$C_4$-haloalkyl, $C_1$-$C_4$-alkoxy and $C_1$-$C_4$-haloalkoxy, or $R^{7b}$ and $R^{11b}$ independently of one another represent aryl or hetaryl, where the radicals mentioned above may each optionally be mono- to trisubstituted and the substituents independently of one another are selected from the group consisting of halogen, nitro, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylsulfinyl and $C_1$-$C_4$-alkylsulfonyl, or $R^{7a}$ and $R^{7b}$ may be attached to one another via two to six carbon atoms and form a ring which may optionally additionally contain a further atom from the group consisting of O, S and N and which may optionally be mono- to tetrasubstituted and where the substituents independently of one another are selected from the group consisting of $C_1$-$C_2$-alkyl, fluorine, chlorine, bromine and $C_1$-$C_2$-alkoxy, or $R^{11a}$ and $R^{11b}$ may be attached to one another via two to six carbon atoms and form a ring which may optionally additionally contain a further atom from the group consisting of O, S and N and which may optionally be mono- to tetrasubstituted and where the substituents independently of one another are selected from the group consisting of $C_1$-$C_2$-alkyl, fluorine, chlorine, bromine and $C_1$-$C_2$-alkoxy, or $R^8$ represents hydrogen, $C_1$-$C_6$-alkyl, $C_3$-$C_6$-cycloalkyl, $C_1$-$C_6$-alkoxycarbonyl or $C_1$-$C_6$-alkylcarbonyl, and $R^{12}$ represents $C_1$-$C_6$-alkyl which may optionally be mono- to pentasubstituted and where the substituents independently of one another are selected from the group consisting of halogen, and/or which may optionally be monosubstituted and where the substituent is selected from the group consisting of nitro, cyano, $C_1$-$C_4$-alkoxy and $C_1$-$C_4$-haloalkoxy, or $R^{12}$ represents aryl or hetaryl, where the radicals mentioned above may each optionally be mono- to trisubstituted and the substituents independently of one another are selected from the group consisting of halogen, nitro, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylsulfinyl and $C_1$-$C_4$-alkylsulfonyl.

Further preferred (Configuration 3-1) are the compounds of the formula (I) in which T represents hydrogen, $C(R^{5a})(R^{5b})(R^{5c})$, $C_2$-$C_4$-alkenyl, $C_3$-$C_4$-alkynyl or $C_3$-$C_6$-cycloalkyl, where $C_2$-$C_4$-alkenyl, $C_3$-$C_4$-alkynyl or $C_3$-$C_6$-cycloalkyl may each optionally be mono- to trisubstituted and the substituents independently of one another are selected from the group consisting of halogen, and/or may each optionally be monosubstituted and the substituent is selected from the group consisting of cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylsulfinyl and $C_1$-$C_4$-alkylsulfonyl, or T represents phenyl, $C_1$-$C_4$-alkylenedioxyphenyl, naphthyl, furanyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidyl, thiophenyl, pyridazinyl, pyrazinyl, 1,2,3-triazinyl, 1,2,4-triazinyl, 1,3,5-triazinyl, benzofuranyl, indolyl, benzothiazolyl, benzoxazolyl, benzimidazolyl, pyrazolopyridinyl, quinolinyl, isoquinolinyl, cinnolinyl, azetidinyl, azolidinyl, azinanyl, oxetanyl, oxolanyl, oxanyl, dioxanyl, thiethanyl, thiolanyl, thianyl, or dihydroisoxazolyl, where the radicals mentioned above may each optionally be mono- to tetrasubstituted and the substituents independently of one another are selected from the group consisting of fluorine and chlorine, and/or may each optionally be mono- to disubstituted and the substituents independently of one another are selected from the group consisting of bromine, nitro, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylsulfonyl, phenyl, pyridyl and morpholinyl, where in total at most five of the substituents mentioned above are present and where phenyl and pyridyl for their part may each additionally be mono- to trisubstituted and the substituents independently of one another are selected from the group consisting of halogen, cyano, $C_1$-$C_4$-alkyl, $C_1$-$C_4$-haloalkyl, $C_1$-$C_4$-alkoxy and $C_1$-$C_4$-haloalkoxy, or T represents $N(R^{7a})(R^{7b})$, or T represents $C(=W)R^{12}$ or $C(=O)OR^{13}$, W represents O or N—$OR^{15}$, G represents $C_1$-$C_4$-alkyl or $C_2$-$C_4$-alkenyl, where the radicals mentioned above are each mono- to trisubstituted by halogen and/or monosubstituted by cyano, $R^1$ represents hydrogen, fluorine, chlorine, methyl, ethyl, methoxy or ethoxy, p represents 1, $R^{5a}$ and $R^{5b}$ independently of one another represent hydrogen, halogen, $C_1$-$C_4$-alkyl or $C_1$-$C_4$-alkoxy, $R^{5c}$ represents hydrogen, fluorine, chlorine, bromine, cyano, $C_1$-$C_4$-alkoxycarbonyl, $C_1$-$C_4$-alkyl, $C_1$-$C_4$-alkoxy or $C_3$-$C_6$-cycloalkyl, where $C_1$-$C_4$-alkyl and $C_3$-$C_6$-cycloalkyl may each optionally be mono- to trisubstituted and the substituents independently of one another are selected from the group consisting of halogen, and/or may each optionally be monosubstituted and the substituent is selected from the group consisting of cyano, $C_1$-$C_4$-haloalkyl, $C_1$-$C_4$-alkoxy and $C_1$-$C_4$-alkoxycarbonyl, or $R^{5c}$ represents phenyl or C-bound pyridyl, where the radicals mentioned above may each optionally be mono- to trisubstituted and the substituents independently of one another are selected from the group consisting of halogen, nitro, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxycarbonyl, $C_1$-$C_4$-alkylthio, $C_1$-$C_4$-alkylsulfinyl and $C_1$-$C_4$-alkylsulfonyl, or $R^{5c}$ represents Y, Y represents one of the radicals Y-2, Y-3, Y-4, Y-5, Y-6 or Y-7, $X^b$ represents halogen, cyano, methyl, ethyl, trifluoromethyl, difluoromethyl, methylaminocarbonyl, methylcarbonylamino, methoxy, ethoxy, trifluoromethoxy, methylthio, ethylthio, methylsulfinyl, methylsulfonyl or methoxycarbonyl, m represents 0, 1 or 2, $R^{13}$ and $R^{15}$ independently of one another represent hydrogen, or represent $C_1$-$C_4$-alkyl, $C_3$-$C_6$-cycloalkyl, $C_3$-$C_6$-heterocyclyl or $C_3$-$C_6$-dioxoheterocyclyl, where the radicals mentioned above may each optionally be mono- to trisubstituted and the substituents independently of one another are selected from the group consisting of halogen, and/or may each optionally be monosubstituted and the substituent is selected from the group consisting of cyano, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylthio, $C_1$-$C_4$-alkylsulfinyl, $C_1$-$C_4$-alkylsulfonyl, $C_1$-$C_4$-alkoxycarbonyl, phenyl and pyridyl, where phenyl and pyridyl for their part may each be mono- to trisubstituted and the substituents independently of one another are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy, $R^{7a}$ represents hydrogen or $C_1$-$C_4$-alkyl, $R^{7b}$ represents hydrogen, or represents $C_1$-$C_6$-alkyl or $C_3$-$C_6$-cycloalkyl, where the radicals mentioned above may each optionally be mono- to trisubstituted and the substituents independently of one another are selected from the group consisting of halogen, and/or may optionally be monosubstituted and the substituent is selected from the group consisting of $C_3$-$C_6$-cycloalkyl and phenyl, where $C_3$-$C_6$-cycloalkyl and phenyl for their part may be mono- to trisubstituted and the substituents independently of one another are selected from the group consisting of halogen, $C_1$-$C_4$-alkyl, $C_1$-$C_4$-haloalkyl and $C_1$-$C_4$-alkoxy, or $R^{7b}$ represents phenyl, pyridyl or pyrazolyl, where the radicals mentioned above may each optionally be mono- to trisubstituted and the substituents independently of one another are selected from the group consisting of halogen, cyano, $C_1$-$C_4$-alkyl, $C_1$-$C_4$-haloalkyl, $C_1$-$C_4$-alkoxy, $C_1$-$C_4$-alkylthio, $C_1$-$C_4$-alkylsulfinyl and $C_1$-$C_4$-alkylsulfonyl, or $R^{7a}$ and $R^{7b}$ may be attached to one another via two to six carbon atoms and form a ring which may optionally additionally contain a further atom from the group consisting of O, S and N and which may optionally be mono- to trisubstituted and where the substituents independently of one another are selected from the group consisting of methyl, ethyl, fluorine, methoxy and ethoxy, and $R^{12}$ represents $C_1$-$C_4$-alkyl which may optionally be mono- to pentasubstituted and where the substituents independently of one another are selected from the group consisting of halogen, or $R^{12}$ represents phenyl which may optionally be mono- to trisubstituted and where the substituents independently of one another are selected from the group consisting of halogen.

Particularly preferred (Configuration 4-1) are the compounds of the formula (I) in which T represents hydrogen, $C(R^{5a})(R^{5b})(R^{5c})$, ethenyl, propenyl, cyclopropyl, cyclobutyl, cyclopentyl or cyclohexyl, where ethenyl, propenyl, cyclopropyl, cyclobutyl, cyclopentyl and cyclohexyl may each optionally be mono- to trisubstituted and the substituents independently of one another are selected from the group consisting of fluorine and chlorine, and/or may each optionally be monosubstituted and the substituent is selected from the group consisting of cyano, methyl, ethyl, trifluoromethyl and methoxy, or T represents phenyl, pyridyl, pyrimidyl, thiophenyl, furanyl, pyrrolyl, thiazolyl, isothiazolyl, oxazolyl, isoxazolyl, pyrazolyl, imidazolyl, pyrazolopyridinyl, benzothiazolyl, benzofuranyl, benzoxazolyl, quinolinyl, oxolanyl or dihydroisoxazolyl, where the radicals mentioned above may each optionally be mono- to tetrasubstituted and the substituents independently of one another are selected from the group consisting of fluorine and chlorine, and/or may each optionally be mono- to disubstituted and the substituents independently of one another are selected from the group consisting of bromine, cyano, methyl, ethyl, difluoromethyl, trifluoromethyl, trifluoroethyl, pentafluoroethyl, trifluoropropyl, methoxy, ethoxy, trifluoromethoxy, methylthio, methylsulfinyl, methylsulfonyl, morpholinyl and phenyl, or T represents $N(R^{7a})(R^{7b})$, or T represents $C(=W)R^{12}$ or $C(=O)OR^{13}$, W represents O or N—$OR^{15}$, G represents cyanomethyl, 2-cyanoethyl, 2,2,2-trifluoroethyl or 3,3,3-trifluoropropyl, $R^1$ represents hydrogen or methyl, p represents 1, $R^{5a}$ and $R^{5b}$ independently of one another represent hydrogen, fluorine, chlorine, methyl, ethyl, methoxy or ethoxy, $R^{5c}$ represents hydrogen, fluorine, chlorine, bromine, cyano, methoxy and methoxycarbonyl, or represents methyl, ethyl, n-propyl, isopropyl, n-butyl, isobutyl, sec-butyl, tert-butyl, cyclopropyl or phenyl, where the radicals mentioned above may each optionally be mono- to trisubstituted and the substituents independently of one another are selected from the group consisting of fluorine and chlorine, and/or may each optionally be monosubstituted and the substituent is selected from the group consisting of cyano, methoxy, methoxycarbonyl and trifluoromethyl, where in total at most three of the substituents mentioned above are present, or $R^{5c}$ represents Y, Y represents the radical Y-2, $X^b$ represents fluorine, chlorine, bromine, cyano, methyl, ethyl, methoxy, ethoxy, methylthio, difluoromethyl or trifluoromethyl, m represents 0 or 1, $R^{13}$ and $R^{15}$ independently of one another represent hydrogen, or represent $C_1$-$C_4$-alkyl, cyclopropyl, cyclobutyl, cyclopentyl, cyclohexyl, oxanyl or 1,1-dioxothianyl, where the radicals mentioned above may each optionally be mono- to trisubstituted and the substituents independently of one another are selected from the group consisting of fluorine and chlorine, and/or may each optionally be monosubstituted and the substituent is selected from the group consisting of cyano, methyl, methoxy, trifluoromethyl, or $R^{13}$ and $R^{15}$ independently of one another represent cyclopropylmethyl, or represent phenylmethyl or pyridylmethyl, where the radicals mentioned above may each optionally be mono- to trisubstituted and the substituents independently of one another are selected from the group consisting of fluorine and chlorine, and/or may each optionally be monosubstituted and the substituent is selected from the group consisting of cyano, methyl, methoxy, trifluoromethyl, where in total at most three of the substituents mentioned above are present, $R^{7a}$ represents hydrogen, $R^{7b}$ represents $C_1$-$C_4$-alkyl, cyclopropyl, benzyl or cyclopropylmethyl, where the radicals mentioned above may each optionally be mono- to trisubstituted and the substituents independently of one another are selected from the group consisting of fluorine and chlorine, or represents phenyl, pyridyl or pyrazolyl, where the radicals mentioned above may optionally be mono- to trisubstituted and the substituents independently of one another are selected from the group consisting of fluorine and chlorine, and/or may optionally be monosubstituted and the substituent is selected from the group consisting of cyano, methyl, methoxy, trifluoromethyl, methylthio, methylsulfinyl and methylsulfonyl, where in total at most three of the substituents mentioned above are present, and $R^{12}$ represents methyl, ethyl, n-propyl, isopropyl, n-butyl, isobutyl, sec-butyl, tert-butyl or phenyl, where the radicals mentioned above may each optionally be mono- to trisubstituted and the substituents independently of one another are selected from the group consisting of fluorine and chlorine.

Particular preference is also given (Configuration 4-2) to the compounds of the formula (I) in which T represents hydrogen, $C(R^{5a})(R^{5b})(R^{5c})$, ethenyl, propenyl, cyclopropyl, cyclobutyl, cyclopentyl or cyclohexyl, where ethenyl, propenyl, cyclopropyl, cyclobutyl, cyclopentyl and cyclohexyl may each optionally be mono- to trisubstituted and the substituents independently of one another are selected from the group consisting of fluorine and chlorine, and/or may each optionally be monosubstituted and the substituent is selected from the group consisting of cyano, methyl, ethyl, trifluoromethyl and methoxy, or T represents phenyl, pyridyl, pyrimidyl, thiophenyl, furanyl, pyrrolyl, thiazolyl, isothiazolyl, 1,3-oxazolyl, 1,2-oxazolyl, pyrazolyl, imidazolyl, 1,2,4-oxadiazolyl, pyrazolopyridinyl, benzothiazolyl, benzofuranyl, benzoxazolyl, quinolinyl, oxolanyl or dihydroisoxazolyl, where the radicals mentioned above may each optionally be mono- to tetrasubstituted and the substituents independently of one another are selected from the group consisting of fluorine and chlorine, and/or may each optionally be mono- to disubstituted and the substituents independently of one another are selected from the group consisting of bromine, cyano, methyl, ethyl, difluoromethyl, trifluoromethyl, trifluoroethyl, pentafluoroethyl, trifluoropropyl, methoxy, ethoxy, trifluoromethoxy, methylthio, methylsulfinyl, methylsulfonyl, morpholinyl and phenyl, or T represents $N(R^{7a})(R^{7b})$, or T represents $C(=W)R^{12}$ or $C(=O)OR^{13}$, W represents O or N—$OR^{15}$, G represents cyanomethyl, 2-cyanoethyl, 2,2,2-trifluoroethyl or 3,3,3-trifluoropropyl, $R^1$ represents hydrogen or methyl, p represents 1, $R^{5a}$ and $R^{5b}$ independently of one another represent hydrogen, fluorine, chlorine, methyl, ethyl, methoxy or ethoxy, $R^{5c}$ represents hydrogen, fluorine, chlorine, bromine, cyano, methoxy and methoxycarbonyl, or represents methyl, ethyl, n-propyl, isopropyl, n-butyl, isobutyl, sec-butyl, tert-butyl, cyclopropyl or phenyl, where the radicals mentioned above may each optionally be mono- to trisubstituted and the substituents independently of one another are selected from the group consisting of fluorine and chlorine, and/or may each optionally be monosubstituted and the substituent is selected from the group consisting of cyano, methoxy, methoxycarbonyl and trifluoromethyl, where in total at most three of the substituents mentioned above are present, or $R^{5c}$ represents Y, Y represents the radical Y-2, $X^b$ represents fluorine, chlorine, bromine, cyano, methyl, ethyl, methoxy, ethoxy, methylthio, difluoromethyl or trifluoromethyl, m represents 0 or 1, $R^{13}$ and $R^{15}$ independently of one another represent hydrogen, or represent $C_1$-$C_4$-alkyl, cyclopropyl, cyclobutyl, cyclopentyl, cyclohexyl, oxanyl or 1,1-dioxothianyl, where the radicals mentioned above may each optionally be mono- to trisubstituted and the substituents independently of one another are selected from the group consisting of fluorine and chlorine, and/or may each optionally be monosubstituted and the substituent is selected from the group consisting of cyano, methyl, methoxy, trifluoromethyl, or $R^{13}$ and $R^{15}$ independently of one another represent cyclopropylmethyl or cyclobutylmethyl, or represent phenylmethyl or pyridylmethyl, where the radicals mentioned above may each optionally be mono- to trisubstituted and the substituents independently of one another are selected from the group consisting of fluorine and chlorine, and/or may each optionally be monosubstituted and the substituent is selected from the group consisting of cyano, methyl, methoxy, trifluoromethyl, where in total at most three of the substituents mentioned above are present, $R^{7a}$ represents hydrogen, $R^{7b}$ represents $C_1$-$C_4$-alkyl, cyclopropyl, benzyl or cyclopropylmethyl, where the radicals mentioned above may each optionally be mono- to trisubstituted and the substituents independently of one another are selected from the group consisting of fluorine and chlorine, or represents phenyl, pyridyl or pyrazolyl, where the radical mentioned above may optionally be mono- to trisubstituted and the substituents independently of one another are selected from the group consisting of fluorine, chlorine and methyl, and/or may optionally be monosubstituted and the substituent is selected from the group consisting of cyano, methyl, methoxy, trifluoromethyl, methylthio, methylsulfinyl and methylsulfonyl, where in total at most three of the substituents mentioned above are present,
and $R^{12}$ represents methyl, ethyl, n-propyl, isopropyl, n-butyl, isobutyl, sec-butyl, tert-butyl or phenyl, where the radicals mentioned above may each optionally be mono- to trisubstituted and the substituents independently of one another are selected from the group consisting of fluorine and chlorine.

Very particularly preferred (Configuration 5-1) are the compounds of the formula (I) in which T represents $C(R^{5a})(R^{5b})(R^{5c})$, cyclopropyl, phenyl, 3-trifluoromethylphenyl, oxazol-2-yl or 1-methylpyrazol-4-yl,
or T represents $N(R^{7a})(R^{7b})$,
or T represents $C(=W)R^{12}$ or $C(=O)OR^{13}$, W represents O, G represents 2-cyanoethyl or 2,2,2-trifluoroethyl, $R^1$ represents hydrogen or methyl, p represents 1, $R^{5a}$ and $R^{5b}$ independently of one another represent hydrogen or fluorine, $R^{5c}$ represents hydrogen, fluorine, methoxy or 4-chloropyrazol-1-yl, $R^{7a}$ represents hydrogen, $R^{7b}$ represents cyclopropyl, 2,6-dichlorophenyl, 3-fluoropyridin-2-yl, 3-trifluoromethylpyridin-2-yl, 2,4-dichloropyridin-3-yl or 1-methylpyrazol-5-yl, $R^{12}$ represents methyl, and $R^{13}$ represents methyl, ethyl, 2,2,2-trifluoroethyl or cyclobutyl.

Very particular preference is also given (Configuration 5-2) to the compounds of the formula (I) in which T represents $C(R^{5a})(R^{5b})(R^{5c})$, cyclopropyl, phenyl, 3-trifluoromethylphenyl, 1,3-thiazol-2-yl, 1,3-oxazol-2-yl, 1,2-oxazol-5-yl, 3-phenyl-1,2,4-oxadiazol-5-yl, 5-trifluoromethylfuran-2-yl, 1-methylpyrazol-3-yl or 1-methylpyrazol-4-yl,
or T represents $N(R^{7a})(R^{7b})$,
or T represents $C(=W)R^{12}$ or $C(=O)OR^{13}$, W represents O or methoximino, G represents 2-cyanoethyl or 2,2,2-trifluoroethyl, $R^1$ represents hydrogen or methyl, p represents 1, $R^{5a}$ and $R^{5b}$ independently of one another represent hydrogen or fluorine, $R^{5c}$ represents hydrogen, fluorine, chlorine, methoxy, trifluoromethyl or 4-chloropyrazol-1-yl, $R^{7a}$ represents hydrogen, $R^{7b}$ represents cyclopropyl, 2,6-dichlorophenyl, 2,6-difluorophenyl, 2,6-dimethylphenyl, 2-chloro-6-cyanophenyl, 3-fluoropyridin-2-yl, 3-trifluoromethylpyridin-2-yl, 2,4-dichloropyridin-3-yl or 1-methylpyrazol-5-yl, $R^{12}$ represents methyl, and $R^{13}$ represents methyl, ethyl, 2,2,2-trifluoroethyl, cyclobutyl, cyclobutylmethyl, 1-methylcyclopropyl.

In a further preferred embodiment, the invention relates to compounds of the formula (I-1)

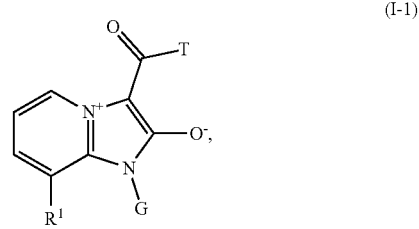

(I-1)

in which the structural elements $R^1$, G and T have the meaning given in Configuration (1-1) or in Configuration (2-1) or in Configuration (3-1) or in Configuration (4-1) or in Configuration (5-1).

In a further preferred embodiment, the invention relates to the compounds of the formula (I-1a)

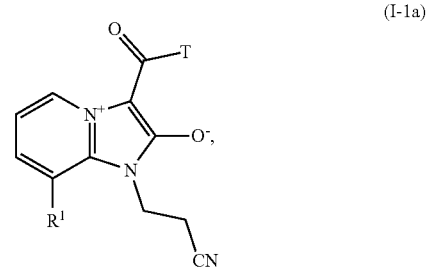

(I-1a)

Among these, particular preference is given to the configurations shown below:

| Compounds of the formula | Structural elements $R^1$ and T according to |
|---|---|
| I-1a | Configuration (1-1) |
| I-1a | Configuration (2-1) |
| I-1a | Configuration (3-1) |
| I-1a | Configuration (4-1) |
| I-1a | Configuration (5-1) |

In a further preferred embodiment, the invention relates to the compounds of the formula (I-1b)

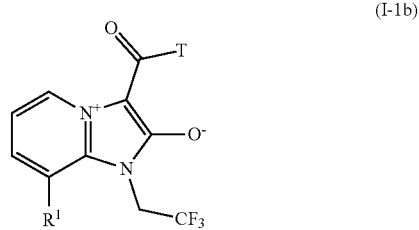

(I-1b)

Among these, particular preference is given to the configurations shown below:

| Compounds of the formula | Structural elements $R^1$ and T according to |
|---|---|
| I-1b | Configuration (1-1) |
| I-1b | Configuration (2-1) |
| I-1b | Configuration (3-1) |
| I-1b | Configuration (4-1) |
| I-1b | Configuration (5-1) |

Compounds according to the invention which are likewise preferred are the compounds of the general formula (I) shown in Table 1.

The general or preferred radical definitions or illustrations given above apply to all compounds of the formula (I) and correspondingly to the starting materials and intermediates. These radical definitions can be combined with one another as desired, i.e. including combinations between the respective preferred ranges.

Preference is given in accordance with the invention to compounds of the formula (I) in which a combination of the definitions given above as preferred is present, and every configuration described above as preferred constitutes an independent combination, in particular a combination as described in Configuration 2-1.

More preference is given in accordance with the invention to compounds of the formula (I) in which a combination of the definitions given above as more preferred is present, and every configuration described above as more preferred constitutes an independent combination, in particular a combination as described in Configuration 3-1.

Particular preference is given in accordance with the invention to compounds of the formula (I) in which a combination of the definitions given above as particularly preferred is present, and every configuration described above as particularly preferred constitutes an independent combination, in particular a combination as described in Configuration 4-1.

Very particular preference is given in accordance with the invention to compounds of the formula (I) in which a combination of the definitions given above as very particularly preferred is present, and every configuration described above as very particularly preferred constitutes an independent combination, in particular a combination as described in Configuration 5-1.

Unless defined otherwise at the appropriate place, optionally substituted radicals may be mono- or polysubstituted, where in the case of polysubstitutions the substituents may be identical or different. The maximum number of substituents at a structural element consequently results from the maximum number of positions available for substituents in this particular structural element.

The compounds of the formula (I) are mesoionic internal salts. Internal salts, also known as zwitterions, are electrically uncharged molecules which formally bear positive and negative charges on different atoms. The compounds of the formula (I) can be formally represented by various structures which bear the positive and negative charges on different atoms. The figure which follows shows 4 possible representation forms without excluding further possible representation forms. All structural representations are equivalent. For reasons of simplification, just one possible structural representation in each case is chosen here. This representation should be understood in each case as being representative of all valence bond structural representations.

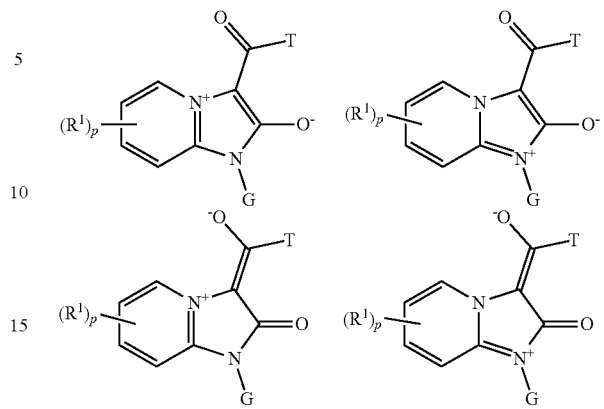

(I)

The compounds of the formula (I) may possibly also, depending on the nature of the substituents, be in the form of stereoisomers, i.e. in the form of geometric and/or optical isomers or isomer mixtures of varying composition. This invention provides both the pure stereoisomers and any desired mixtures of these isomers, even though it is generally only compounds of the formula (I) that are discussed here.

However, preference is given in accordance with the invention to using the optically active, stereoisomeric forms of the compounds of the formula (I) and salts thereof.

The invention therefore relates both to the pure enantiomers and diastereomers and to mixtures thereof for controlling animal pests, including arthropods and particularly insects.

If appropriate, the compounds of the formula (I) may be present in various polymorphic forms or as a mixture of various polymorphic forms. Both the pure polymorphs and the polymorph mixtures are provided by the invention and can be used in accordance with the invention.

In the context of the present invention, unless defined differently elsewhere, the term "alkyl", either on its own or else in combination with further terms, for example haloalkyl, is understood to mean a radical of a saturated aliphatic hydrocarbon group which has 1 to 12 carbon atoms and may be branched or unbranched. Examples of $C_1$-$C_{12}$-alkyl radicals are methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1-ethylpropyl, 1,2-dimethylpropyl, hexyl, n-heptyl, n-octyl, n-nonyl, n-decyl, n-undecyl and n-dodecyl. Among these alkyl radicals, particular preference is given to $C_1$-$C_6$-alkyl radicals. Particular preference is given to $C_1$-$C_4$-alkyl radicals.

According to the invention, unless defined differently elsewhere, the term "alkenyl", either on its own or else in combination with further terms, is understood to mean a straight-chain or branched $C_2$-$C_{12}$-alkenyl radical which has at least one double bond, for example vinyl, allyl, 1-propenyl, isopropenyl, 1-butenyl, 2-butenyl, 3-butenyl, 1,3-butadienyl, 1-pentenyl, 2-pentenyl, 3-pentenyl, 4-pentenyl, 1,3-pentadienyl, 1-hexenyl, 2-hexenyl, 3-hexenyl, 4-hexenyl, 5-hexenyl and 1,4-hexadienyl. Among these, preference is given to $C_2$-$C_6$-alkenyl radicals and particular preference to $C_2$-$C_4$-alkenyl radicals.

According to the invention, unless defined differently elsewhere, the term "alkynyl", either on its own or else in combination with further terms, is understood to mean a straight-chain or branched $C_2$-$C_{12}$-alkynyl radical which has at least one triple bond, for example ethynyl, 1-propynyl and propargyl. Among these, preference is given to $C_3$-$C_6$-alkynyl radicals and particular preference to $C_3$-$C_4$-alkynyl radicals. The alkynyl radical may also contain at least one double bond.

According to the invention, unless defined differently elsewhere, the term "cycloalkyl", either on its own or else in combination with further terms, is understood to mean a $C_3$-$C_8$-cycloalkyl radical, for example cyclopropyl, cyclobutyl, cyclopentyl, cyclohexyl, cycloheptyl and cyclooctyl. Among these, preference is given to $C_3$-$C_6$-cycloalkyl radicals.

According to the invention, unless defined differently elsewhere, the term "aryl" is understood to mean an aromatic radical having 6 to 14 carbon atoms, preferably phenyl, naphthyl, anthryl or phenanthrenyl, more preferably phenyl.

Unless defined differently elsewhere, the term "arylalkyl" is understood to mean a combination of the radicals "aryl" and "alkyl" defined according to the invention, where the radical is generally attached via the alkyl group. Examples of these are benzyl, phenylethyl or α-methylbenzyl, benzyl being particularly preferred.

Unless defined differently elsewhere, "hetaryl" denotes a mono-, bi- or tricyclic heterocyclic group of carbon atoms and at least one heteroatom, where at least one cycle is aromatic.

Preferably, the hetaryl group contains 3, 4, 5 or 6 carbon atoms selected from the group of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuranyl, benzisofuryl, benzothienyl, benzisothienyl, indolyl, isoindolyl, indazolyl, benzothiazolyl, benzisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl.

Unless defined differently elsewhere, "heterocyclyl" denotes a monocyclic, saturated or partially saturated 4-, 5-, 6- or 7-membered ring of carbon atoms and at least one heteroatom in the ring. Preferably, the heterocyclyl group contains 3, 4, 5 or 6 carbon atoms and 1 or 2 heteroatoms from the group consisting of oxygen, sulfur and nitrogen. Examples of heterocyclyl are azetidinyl, azolidinyl, azinanyl, oxetanyl, oxolanyl, oxanyl, dioxanyl, thietanyl, thiolanyl, thianyl and tetrahydrofuryl.

Unless defined differently elsewhere, "oxoheterocyclyl" and "dioxoheterocyclyl" denote a heterocyclyl which contains, in at least one position in the ring, a ring atom substituted, respectively, by one and two (=O) groups. Preferably, a heteroatom, for example sulfur, is substituted by one or two (=O) groups, resulting respectively in the —S(=O)— and —S(=O)$_2$— groups, where the sulfur atom is a constituent of the ring.

In the context of the present invention, halogen-substituted radicals, for example "haloalkyl", are understood to mean radicals which are mono- or polyhalogenated up to the maximum possible number of substituents. In the case of polyhalogenation, the halogen atoms may be identical or different. "Halogen" here is fluorine, chlorine, bromine or iodine, preferably fluorine or chlorine.

The term "alkoxy", either on its own or else in combination with further terms, for example haloalkoxy, is understood in the present case to mean an O-alkyl radical, where the term "alkyl" is as defined above.

Description of the Processes and Intermediates

The compounds of the formula (I) can be synthesized, for example, by the processes specified in Scheme 1. Here, the radicals $R^1$, p, T, G, $R^{7a}$ and $R^{7b}$ given in the formulae each have, unless indicated otherwise, the meaning given in Configurations (1-1) to (5-1).

Scheme 1

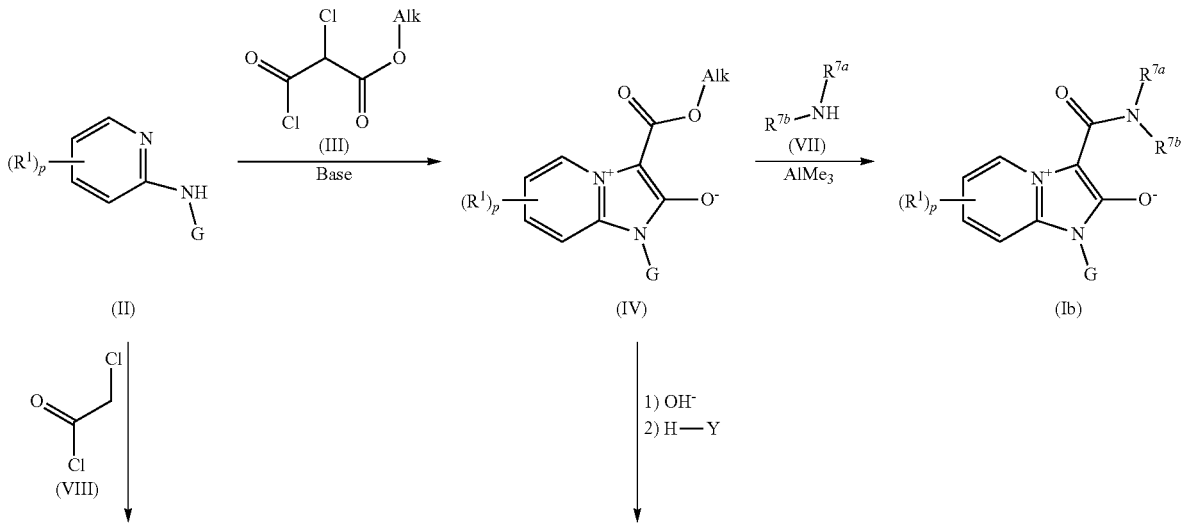

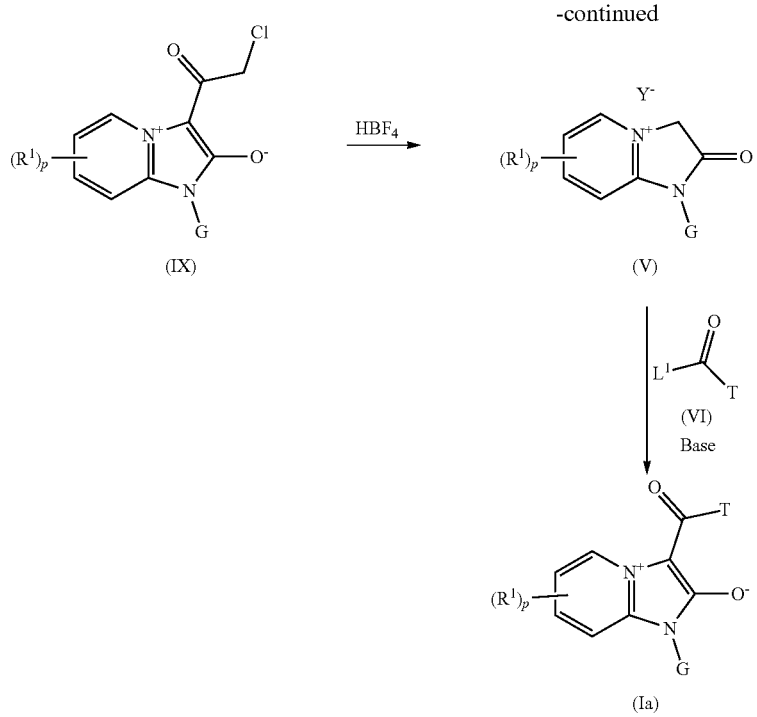

Compounds of the formula (Ia), in which T does not represent $NR^{7a}R^{7b}$, can be obtained as shown in Scheme 1. Here, initially amino compounds of the formula (II) are reacted with acid chlorides of the formula (III) in the presence of a base such as, for example, triethylamine, giving carboxylic esters of the formula (IV) in which Alk represents $C_1$-$C_4$-alkyl. Compounds of the formula (IV) are then hydrolysed with a base such as, for example, lithium hydroxide to give carboxylic acids and then decarboxylated to give compounds of the formula (V) by reaction with an acid H—Y, where $Y^-$ represents the anion of an inorganic acid such as, for example, $F^-$, $Cl^-$, $Br^-$, $I^-$, $NO_3^-$, $SO_4^-$, $ClO_4^-$ or $BF_4^-$. Compounds of the formula (V) are novel and, as important intermediates for the synthesis of compounds of the formula (I), also form part of the subject-matter of the invention. Alternatively, compounds of the formula (II) can be initially reacted with chloroacetyl chloride (VIII) to give chloromethyl ketones of the formula (IX), from which compounds of the formula (V, $Y=BF_4^-$) are then obtained analogously to known processes by reaction with tetrafluoroboric acid (cf. Tetrahedron 65 (2009), 7591-7596). Compounds of the formula (V) can then be reacted with a compound of the formula (VI) in which $L^1$ represents Cl, Br or —O(=O)T, (for example an acid chloride or an anhydride) in the presence of a base such as, for example, triethylamine, to give compounds of the formula (Ia).

Compounds of the formula (Ib), in which T represents $NR^{5a}R^{5b}$, can be obtained as shown in Scheme 1. Here, esters of the formula (IV) are reacted with amines of the formula (VII) analogously to generally known processes. For the reaction with certain amines, activation reagents, such as, for example, trimethylaluminium need to be used if appropriate.

Compounds of the formula (II) are known from the literature (cf., for example, WO 2016171053, WO 2009099929) or can be obtained analogously to methods known from the literature. Compounds of the formula (III) are known from the literature or can be prepared analogously to known processes (cf. Tetrahedron 1993, 49, 9447-9452). Compounds of the formula (VI) and (VII) are commercially available, known from the literature or can be synthesized analogously to known processes.

In general, compounds of the formula (I) can be prepared by the processes described above. If individual compounds cannot be prepared by the processes described above, synthesis is possible by derivatization of other compounds of the formula (I), or by individual modifications to the processes described. For example, it may have advantages to prepare certain compounds of the formula (I) from other compounds of the formula (I), for example by hydrolysis, esterification, amide formation, reduction, etherification, oxidation, olefination, halogenation, acylation, alkylation and the like.

The processes according to the invention for preparation of the novel compounds of the formula (I) are preferably performed using a diluent. Useful diluents for performance of the processes according to the invention are, as well as water, all inert solvents. Examples include: halohydrocarbons (e.g. chlorohydrocarbons such as tetraethylene, tetrachloroethane, dichloropropane, methylene chloride, dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, chlorotoluene, trichlorobenzene), alcohols (e.g. methanol, ethanol, isopropanol, butanol), ethers (e.g. ethyl propyl ether, methyl tert-butyl ether, anisole, phenetole, cyclohexyl methyl ether, dimethyl ether, diethyl ether, dipropyl ether, diisopropyl ether, di-n-butyl ether, diisobutyl ether, diisoamyl ether, ethylene glycol dimethyl ether, tetrahydrofuran, 1,4-dioxane, dichlorodiethyl ether and polyethers of ethylene oxide and/or propylene oxide), amines (e.g. trimethyl-, triethyl-, tripropyl-, tributylamine, N-methylmorpholine, pyridine and tetramethylenediamine), nitrohydrocarbons (e.g. nitromethane, nitroethane, nitropropane, nitrobenzene, chloronitrobenzene, o-nitrotoluene); nitriles (such as acetonitrile, propionitrile, butyronitrile, isobutyronitrile, benzonitrile, m-chlorobenzonitrile), tetrahydrothiophene dioxide, dimethyl sulfoxide, tetramethylene sulfoxide, dipropyl sulfoxide, benzyl methyl sulfoxide, diisobutyl sulfoxide, dibutyl sulfoxide, diisoamyl sulfoxide, sulfones (e.g. dimethyl, diethyl, dipropyl, dibutyl, diphenyl, dihexyl, methyl ethyl, ethyl propyl, ethyl isobutyl and pentamethylene sulfone), aliphatic, cycloaliphatic or aromatic hydrocarbons (e.g. pentane, hexane, heptane, octane, nonane and industrial hydrocarbons), also white spirits with components having boiling points in the range, for example, from 40° C. to 250° C., cymene, benzine fractions within a boiling point range from 70° C. to 190° C., cyclohexane, methylcyclohexane, petroleum ether, ligroin, octane, benzene, toluene, chlorobenzene, bromobenzene, nitrobenzene, xylene, esters (e.g. methyl acetate, ethyl acetate, butyl acetate and isobutyl acetate, dimethyl carbonate, dibutyl carbonate and ethylene carbonate); amides (e.g. hexamethylenephosphoric triamide, formamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine, N,N'-diformylpiperazine) and ketones (e.g. acetone, acetophenone, methyl ethyl ketone, methyl butyl ketone).

It is of course also possible to perform the process according to the invention in mixtures of the solvents and diluents mentioned.

When performing the processes according to the invention, the reaction temperatures can be varied within a relatively wide range. In general, the process is carried out at temperatures between −30° C. and +150° C., preferably between −10° C. and +100° C.

The processes according to the invention are generally carried out under standard pressure. However, it is also possible to perform the process according to the invention under elevated or reduced pressure—generally at absolute pressures between 0.1 bar and 15 bar.

For carrying out the process according to the invention, the starting materials are generally employed in approximately equimolar amounts. However, it is also possible to use one of the components in a relatively large excess. The reaction is generally performed in a suitable diluent in the presence of a reaction auxiliary, optionally also under a protective gas atmosphere (for example under nitrogen, argon or helium) and the reaction mixture is generally stirred at the temperature required for several hours. The workup is performed by customary methods (cf. the preparation examples).

The basic reaction auxiliaries used to perform the processes according to the invention may be all suitable acid binders. Examples include: alkaline earth metal or alkali metal compounds (e.g. hydroxides, hydrides, oxides and carbonates of lithium, sodium, potassium, magnesium, calcium and barium), amidine bases or guanidine bases (e.g. 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine) and amines, especially tertiary amines (e.g. triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, β-picoline, pyrimidine, acridine, N,N,N',N'-tetramethylenediamine, N,N,N',N'-tetraethylenediamine, quinoxaline, N-propyldiisopropylamine, N-ethyldiisopropylamine, N,N'-dimethylcyclohexylamine, 2,6-lutidine, 2,4-lutidine or triethyldiamine).

The acidic reaction auxiliaries which may be used to perform the processes according to the invention include all mineral acids (e.g. hydrohalic acids such as hydrofluoric acid, hydrochloric acid, hydrobromic acid or hydriodic acid, and also sulfuric acid, phosphoric acid, phosphorous acid, nitric acid), Lewis acids (e.g. aluminium(III) chloride, boron trifluoride or its etherate, titanium(IV) chloride, tin(IV) chloride) and organic acids (e.g. formic acid, acetic acid, propionic acid, malonic acid, lactic acid, oxalic acid, fumaric acid, adipic acid, stearic acid, tartaric acid, oleic acid, methanesulfonic acid, benzoic acid, benzenesulfonic acid or para-toluenesulfonic acid).

The invention furthermore provides intermediates of the formula (IV)

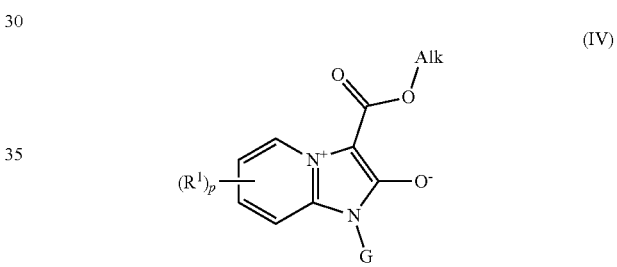

(IV)

in which the structural elements $R^1$, p and G have the meaning given in Configuration (1-1) or in Configuration (2-1) or in Configuration (3-1) or in Configuration (4-1) or in Configuration (5-1) and where Alk represents $C_1$-$C_4$-alkyl, preferably methyl and ethyl and particularly preferably methyl.

In a preferred embodiment, these are intermediates of the formula (IV-1)

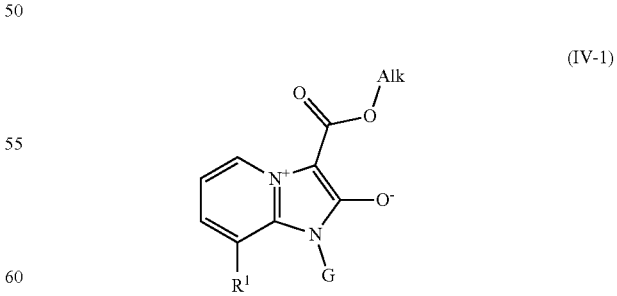

(IV-1)

in which the structural elements $R^1$ and G have the meaning given in Configuration (1-1) or in Configuration (2-1) or in Configuration (3-1) or in Configuration (4-1) or in Configuration (5-1) and where Alk represents $C_1$-$C_4$-alkyl, preferably methyl or ethyl.

The invention further provides intermediates of the formula (V)

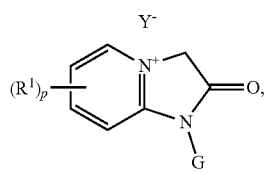

(V)

in which the structural elements $R^1$, p and G have the meaning given in Configuration (1-1) or in Configuration (2-1) or in Configuration (3-1) or in Configuration (4-1) or in Configuration (5-1) and where $Y^-$ represents $F^-$, $Cl^-$, $Br^-$, $I^-$, $NO_3^-$, $SO_4^-$, $BF_4^-$ or $ClO_4^-$, preferably $F^-$, $Cl^-$, $Br^-$, $I^-$ or $BF_4^-$ and particularly preferably $Br^-$, $Cl^-$ or $BF_4^-$.

In a preferred embodiment, these are intermediates of the formula (V-1)

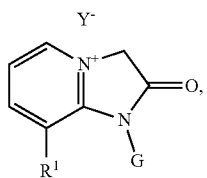

(V-1)

in which the structural elements $R^1$ and G have the meaning given in Configuration (1-1) or in Configuration (2-1) or in Configuration (3-1) or in Configuration (4-1) or in Configuration (5-1) and where $Y^-$ represents $F^-$, $Cl^-$, $Br^-$, $I^-$ or $BF_4^-$, preferably $Br^-$, $Cl^-$ or $BF_4^-$.

Isomers

Depending on the nature of the substituents, the compounds of the formula (I) may take the form of geometric and/or optically active isomers or corresponding isomer mixtures in different compositions. These stereoisomers are, for example, enantiomers, diastereomers, atropisomers or geometric isomers. The invention therefore encompasses both pure stereoisomers and any desired mixtures of these isomers.

Methods and Uses

The invention also relates to methods for controlling animal pests where compounds of the formula (I) are allowed to act on animal pests and/or their habitat. The control of the animal pests is preferably carried out in agriculture and forestry, and in material protection. This preferably excludes methods for surgical or therapeutic treatment of the human or animal body and diagnostic methods carried out on the human or animal body.

The invention further relates to the use of the compounds of the formula (I) as pesticides, especially crop protection compositions.

In the context of the present application, the term "pesticide" in each case also always encompasses the term "crop protection composition".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, especially nematodes and molluscs, which are encountered in agriculture, in horticulture, in animal husbandry, in aquatic cultures, in forests, in gardens and leisure facilities, in the protection of stored products and of materials, and in the hygiene sector.

In the context of the present patent application, the term "hygiene" should be understood to mean any and all measures, provisions and procedures which have the aim of preventing diseases, especially infection diseases, and which serve to protect the health of humans and animals and/or protect the environment and/or maintain cleanliness. According to the invention, this especially includes measures for cleaning, disinfection and sterilization, for example of textiles or hard surfaces, especially surfaces made of glass, wood, cement, porcelain, ceramic, plastic or else metal(s), in order to ensure that these are free of hygiene pests and/or their secretions. The scope of protection of the invention in this regard preferably excludes surgical or therapeutic treatment procedures to be applied to the human body or the bodies of animals, and diagnostic procedures which are carried out on the human body or the bodies of animals.

The term "hygiene sector" covers all areas, technical fields and industrial applications in which these hygiene measures, provisions and procedures are important, for example with regard to hygiene in kitchens, bakeries, airports, bathrooms, swimming pools, department stores, hotels, hospitals, stables, animal keeping, etc.

The term "hygiene pest" should therefore be understood to mean one or more animal pests whose presence in the hygiene sector is problematic, especially for reasons of health. A main aim is therefore that of avoiding, or limiting to a minimum, the presence of hygiene pests and/or the exposure to these in the hygiene sector. This can especially be achieved through the use of a pesticide which can be used both for prevention of infestation and for prevention of an existing infestation. It is also possible to use formulations which prevent or reduce exposure to pests. Hygiene pests include, for example, the organisms mentioned below.

The term "hygiene protection" thus covers all acts by which these hygiene measures, provisions and procedures are maintained and/or improved.

The compounds of the formula (I) can preferably be used as pesticides. They are active against normally sensitive and resistant species and also against all or specific stages of development.

The aforementioned pests include:

pests from the phylum of the Arthropoda, in particular from the class of the Arachnida, for example *Acarus* spp., for example *Acarus siro, Aceria kuko, Aceria sheldoni, Aculops* spp., *Aculus* spp., e.g. *Aculus fockeui, Aculus schlechtendali, Amblyomma* spp., *Amphitetranychus viennensis, Argas* spp., *Boophilus* spp., *Brevipalpus* spp., e.g. *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., e.g. *Eotetranychus hicoriae, Epitrimerus pyri, Eutetranychus* spp., e.g. *Eutetranychus banksi, Eriophyes* spp., e.g. *Eriophyes pyri, Glycyphagus domesticus, Halotydeus destructor, Hemitarsonemus* spp., e.g. *Hemitarsonemus latus* (=*Polyphagotarsonemus latus*), *Hyalomma* spp., *Ixodes* spp., *Latrodectus* spp., *Loxosceles* spp., *Neutrombicula autumnalis, Nuphersa* spp., *Oligonychus* spp., e.g. *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., e.g. *Panonychus citri* (=*Meta-

*tetranychus citri*), *Panonychus ulmi* (=*Metatetranychus ulmi*), *Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., e.g. *Tarsonemus confusus, Tarsonemus pallidus, Tetranychus* spp., e.g. *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea e.g. *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., e.g. *Periplaneta americana, Periplaneta australasiae, Pycnoscelus surinamensis, Supella longipalpa;* from the order of the Coleoptera, for example *Acalymma vittatum, Acanthoscelides obtectus, Adoretus* spp., *Aethina tumida, Agelastica alni, Agrilus* spp., e.g. *Agrilus planipennis, Agrilus coxalis, Agrilus bilineatus, Agrilus anxius, Agriotes* spp., e.g. *Agriotes linneatus, Agriotes mancus, Alphitobius diaperinus, Amphimallon solstitialis, Anobium punctatum, Anoplophora* spp., e.g. *Anoplophora glabripennis, Anthonomus* spp., e.g. *Anthonomus grandis, Anthrenus* spp., *Apion* spp., *Apogonia* spp., *Atomaria* spp., e.g. *Atomaria linearis, Attagenus* spp., *Baris caerulescens, Bruchidius obtectus, Bruchus* spp., e.g. *Bruchus pisorum, Bruchus rufimanus, Cassida* spp., *Cerotoma trifurcata, Ceutorrhynchus* spp., e.g. *Ceutorrhynchus assimilis, Ceutorrhynchus quadridens, Ceutorrhynchus rapae, Chaetocnema* spp., e.g. *Chaetocnema confinis, Chaetocnema denticulata, Chaetocnema ectypa, Cleonus mendicus, Conoderus* spp., *Cosmopolites* spp., e.g. *Cosmopolites sordidus, Costelytra zealandica, Ctenicera* spp., *Curculio* spp., e.g. *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus fumissi, Dendroctonus* spp., e.g. *Dendroctonus ponderosae, Dermestes* spp., *Diabrotica* spp., e.g. *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., e.g. *Epilachna borealis, Epilachna varivestis, Epitrix* spp., e.g. *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., e.g. *Hypothenemus hampei, Hypothenemus obscurus, Hypothenemus pubescens, Lachnostema consanguinea, Lasioderma serricome, Latheticus oryzae, Lathridius* spp., *Lema* spp., *Leptinotarsa decemlineata, Leucoptera* spp., e.g. *Leucoptera coffeella, Limonius ectypus, Lissorhoptrus oryzophilus, Listronotus* (=*Hyperodes*) spp., *Lixus* spp., *Luperodes* spp., *Luperomorpha xanthodera, Lyctus* spp., *Megacyllene* spp., e.g. *Megacyllene robiniae, Megascelis* spp., *Melanotus* spp., e.g. *Melanotus longulus oregonensis, Meligethes aeneus, Melolontha* spp., e.g. *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., e.g. *Otiorhynchus cribricollis, Otiorhynchus ligustici, Otiorhynchus ovatus, Otiorhynchus rugosostriarus, Otiorhynchus sulcatus, Oulema* spp., e.g. *Oulema melanopus, Oulema oryzae, Oxycetonia jucunda, Phaedon cochleariae, Phyllophaga* spp., *Phyllophaga helleri, Phyllotreta* spp., e.g. *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., e.g. *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Scolytus* spp., e.g. *Scolytus multistriatus, Sinoxylon perforans, Sitophilus* spp., e.g. *Sitophilus granarius, Sitophilus linearis, Sitophilus oryzae, Sitophilus zeamais, Sphenophorus* spp., *Stegobium paniceum, Sternechus* spp., e.g. *Sternechus paludatus, Symphyletes* spp., *Tanymecus* spp., e.g. *Tanymecus dilaticollis, Tanymecus indicus, Tanymecus palliatus, Tenebrio molitor, Tenebrioides mauretanicus, Tribolium* spp., e.g. *Tribolium audax, Tribolium castaneum, Tribolium confusum, Trogoderma* spp., *Tychius* spp., *Xylotrechus* spp., *Zabrus* spp., e.g. *Zabrus tenebrioides;* from the order of the Dermaptera, for example *Anisolabis maritime, Forficula auricularia, Labidura riparia;* from the order of the Diptera, for example *Aedes* spp., e.g. *Aedes aegypti, Aedes albopictus, Aedes sticticus, Aedes vexans, Agromyza* spp., e.g. *Agromyza frontella, Agromyza parvicomis, Anastrepha* spp., *Anopheles* spp., e.g. *Anopheles quadrimaculatus, Anopheles gambiae, Asphondylia* spp., *Bactrocera* spp., e.g. *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., e.g. *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., e.g. *Culex pipiens, Culex quinquefasciatus, Culicoides* spp., *Culiseta* spp., *Cuterebra* spp., *Dacus oleae, Dasineura* spp., e.g. *Dasineura brassicae, Delia* spp., e.g. *Delia antiqua, Delia coarctata, Delia florilega, Delia platura, Delia radicum, Dermatobia hominis, Drosophila* spp., e.g. *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., e.g. *Liriomyza brassicae, Liriomyza huidobrensis, Liriomyza sativae, Lucilia* spp., e.g. *Lucilia cuprina, Lutzomyia* spp., *Mansonia* spp., *Musca* spp., e.g. *Musca domestica, Musca domestica vicina, Oestrus* spp., *Oscinella frit, Paratanytarsus* spp., *Paralauterbomiella subcincta, Pegomya oder Pegomyia* spp., e.g. *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., e.g. *Rhagoletis cingulata, Rhagoletis completa, Rhagoletis fausta, Rhagoletis indifferens, Rhagoletis mendax, Rhagoletis pomonella, Sarcophaga* spp., *Simulium* spp., e.g. *Simulium meridionale, Stomoxys* spp., *Tabanus* spp., *Tetanops* spp., *Tipula* spp., e.g. *Tipula paludosa, Tipula simplex, Toxotrypana curvicauda;* from the order of the Hemiptera, for example *Acizzia acaciaebaileyanae*, *Acizzia dodonaeae*, *Acizzia uncatoides*, *Acrida turrita*, *Acyrthosipon* spp., e.g. *Acyrthosiphon pisum*, *Acrogonia* spp., *Aeneolamia* spp., *Agonoscena* spp., *Aleurocanthus* spp., *Aleyrodes proletella*, *Aleurolobus barodensis*, *Aleurothrixus floccosus*, *Allocaridara malayensis*, *Amrasca* spp., e.g. *Amrasca bigutulla*, *Amrasca devastans*, *Anuraphis cardui*, *Aonidiella* spp., e.g. *Aonidiella aurantii*, *Aonidiella citrina*, *Aonidiella inomata*, *Aphanostigma piri*, *Aphis* spp., e.g. *Aphis citricola*, *Aphis craccivora*, *Aphis fabae*, *Aphis forbesi*, *Aphis glycines*, *Aphis gossypii*, *Aphis hederae*, *Aphis illinoisensis*, *Aphis middletoni*, *Aphis nasturtii*, *Aphis nerii*, *Aphis pomi*, *Aphis spiraecola*, *Aphis vibumiphila*, *Arboridia apicalis*, *Arytainilla* spp., *Aspidiella* spp., *Aspidiotus* spp., e.g. *Aspidiotus nerii*, *Atanus* spp., *Aulacorthum solani*, *Bemisia tabaci*, *Blastopsylla occidentalis*, *Boreioglycaspis melaleucae*, *Brachycaudus helichrysi*, *Brachycolus* spp., *Brevicoryne brassicae*, *Cacopsylla* spp., e.g. *Cacopsylla pyricola*, *Calligypona marginata*, *Capulinia* spp., *Cameocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chondracris rosea*, *Chromaphis juglandicola*, *Chrysomphalus aonidum*, *Chrysomphalus ficus*, *Cicadulina mbila*, *Coccomytilus halli*, *Coccus* spp., e.g. *Coccus hesperidum*, *Coccus longulus*, *Coccus pseudomagnoliarum*, *Coccus viridis*, *Cryptomyzus ribis*, *Cryptoneossa* spp., *Ctenarytaina* spp., *Dalbulus* spp., *Dialeurodes chittendeni*, *Dialeurodes citri*, *Diaphorina citri*, *Diaspis* spp., *Diuraphis* spp., *Doralis* spp., *Drosicha* spp., *Dysaphis* spp., e.g. *Dysaphis apiifolia*, *Dysaphis plantaginea*, *Dysaphis tulipae*, *Dysmicoccus* spp., *Empoasca* spp., e.g. *Empoasca abrupta*, *Empoasca fabae*, *Empoasca maligna*, *Empoasca solana*, *Empoasca stevensi*, *Eriosoma* spp., e.g. *Eriosoma americanum*, *Eriosoma lanigerum*, *Eriosoma pyricola*, *Erythroneura* spp., *Eucalyptolyma* spp., *Euphyllura* spp., *Euscelis bilobatus*, *Ferrisia* spp., *Fiorinia* spp., *Furcaspis oceanica*, *Geococcus coffeae*, *Glycaspis* spp., *Heteropsylla cubana*, *Heteropsylla spinulosa*, *Homalodisca coagulata*, *Hyalopterus arundinis*, *Hyalopterus pruni*, *Icerya* spp., e.g. *Icerya purchasi*, *Idiocerus* spp., *Idioscopus* spp., *Laodelphax striatellus*, *Lecanium* spp., e.g. *Lecanium comi* (=*Parthenolecanium comi*), *Lepidosaphes* spp., e.g. *Lepidosaphes ulmi*, *Lipaphis erysimi*, *Lopholeucaspis japonica*, *Lycorma delicatula*, *Macrosiphum* spp., e.g. *Macrosiphum euphorbiae*, *Macrosiphum lilii*, *Macrosiphum rosae*, *Macrosteles facifrons*, *Mahanarva* spp., *Melanaphis sacchari*, *Metcalfiella* spp., *Metcalfa pruinosa*, *Metopolophium dirhodum*, *Monellia costalis*, *Monelliopsis pecanis*, *Myzus* spp., e.g. *Myzus ascalonicus*, *Myzus cerasi*, *Myzus ligustri*, *Myzus omatus*, *Myzus persicae*, *Myzus nicotianae*, *Nasonovia ribisnigri*, *Neomaskellia* spp., *Nephotettix* spp., e.g. *Nephotettix cincticeps*, *Nephotettix nigropictus*, *Nettigoniclla spectra*, *Nilaparvata lugens*, *Oncometopia* spp., *Orthezia praelonga*, *Oxya chinensis*, *Pachypsylla* spp., *Parabemisia myricae*, *Paratrioza* spp., e.g. *Paratrioza cockerelli*, *Parlatoria* spp., *Pemphigus* spp., e.g. *Pemphigus bursarius*, *Pemphigus populivenae*, *Peregrinus maidis*, *Perkinsiella* spp., *Phenacoccus* spp., e.g. *Phenacoccus madeirensis*, *Phloeomyzus passerinii*, *Phorodon humuli*, *Phylloxera* spp., e.g. *Phylloxera devastatrix*, *Phylloxera notabilis*, *Pinnaspis aspidistrae*, *Planococcus* spp., e.g. *Planococcus citri*, *Prosopidopsylla flava*, *Protopulvinaria pyriformis*, *Pseudaulacaspis pentagona*, *Pseudococcus* spp., e.g. *Pseudococcus calceolariae*, *Pseudococcus comstocki*, *Pseudococcus* longispinus, *Pseudococcus maritimus*, *Pseudococcus vibumi*, *Psyllopsis* spp., *Psylla* spp., e.g. *Psylla buxi*, *Psylla mali*, *Psylla pyri*, *Pteromalus* spp., *Pulvinaria* spp., *Pyrilla* spp., *Quadraspidiotus* spp., e.g. *Quadraspidiotus juglansregiae*, *Quadraspidiotus ostreaeformis*, *Quadraspidiotus pemiciosus*, *Quesada gigas*, *Rastrococcus* spp., *Rhopalosiphum* spp., e.g. *Rhopalosiphum maidis*, *Rhopalosiphum oxyacanthae*, *Rhopalosiphum padi*, *Rhopalosiphum rufiabdominale*, *Saissetia* spp., e.g. *Saissetia coffeae*, *Saissetia miranda*, *Saissetia neglecta*, *Saissetia oleae*, *Scaphoideus titanus*, *Schizaphis graminum*, *Selenaspidus articulatus*, *Sipha flava*, *Sitobion avenae*, *Sogata* spp., *Sogatella furcifera*, *Sogatodes* spp., *Stictocephala festina*, *Siphoninus phillyreae*, *Tenalaphara malayensis*, *Tetragonocephela* spp., *Tinocallis caryaefoliae*, *Tomaspis* spp., *Toxoptera* spp., e.g. *Toxoptera aurantii*, *Toxoptera citricidus*, *Trialeurodes vaporariorum*, *Trioza* spp., e.g. *Trioza diospyri*, *Typhlocyba* spp., *Unaspis* spp., *Viteus vitifolii*, *Zygina* spp.;

from the suborder of the Heteroptera, for example *Aelia* spp., *Anasa tristis*, *Antestiopsis* spp., *Boisea* spp., *Blissus* spp., *Calocoris* spp., *Campylomma livida*, *Cavelerius* spp., *Cimex* spp., e.g. *Cimex adjunctus*, *Cimex hemipterus*, *Cimex lectularius*, *Cimex pilosellus*, *Collaria* spp., *Creontiades dilutus*, *Dasynus piperis*, *Dichelops furcatus*, *Diconocoris hewetti*, *Dysdercus* spp., *Euschistus* spp., e.g. *Euschistus heros*, *Euschistus servus*, *Euschistus tristigmus*, *Euschistus variolarius*, *Eurydema* spp., *Eurygaster* spp., *Halyomorpha halys*, *Heliopeltis* spp., *Horcias nobilellus*, *Leptocorisa* spp., *Leptocorisa varicomis*, *Leptoglossus occidentalis*, *Leptoglossus phyllopus*, *Lygocoris* spp., e.g. *Lygocoris pabulinus*, *Lygus* spp., e.g. *Lygus elisus*, *Lygus hesperus*, *Lygus lineolaris*, *Macropes excavatus*, *Megacopta cribraria*, *Miridae*, *Monalonion atratum*, *Nezara* spp., e.g. *Nezara viridula*, *Nysius* spp., *Oebalus* spp., *Pentomidae*, *Piesma quadrata*, *Piezodorus* spp., e.g. *Piezodorus guildinii*, *Psallus* spp., *Pseudacysta persea*, *Rhodnius* spp., *Sahlbergella singularis*, *Scaptocoris castanea*, *Scotinophora* spp., *Stephanitis nashi*, *Tibraca* spp., *Triatoma* spp.;

from the order of the Hymenoptera, for example, *Acromyrmex* spp., *Athalia* spp., e.g. *Athalia rosae*, *Atta* spp., *Camponotus* spp., *Dolichovespula* spp., *Diprion* spp., e.g. *Diprion similis*, *Hoplocampa* spp., e.g. *Hoplocampa cookei*, *Hoplocampa testudinea*, *Lasius* spp., *Linepithema* (*Iridiomyrmex*) *humile*, *Monomorium pharaonis*, *Paratrechina* spp., *Paravespula* spp., *Plagiolepis* spp., *Sirex* spp., e.g. *Sirex noctilio*, *Solenopsis invicta*, *Tapinoma* spp., *Technomyrmex albipes*, *Urocerus* spp., *Vespa* spp., e.g. *Vespa crabro*, *Wasmannia auropunctata*, *Xeris* spp.; from the order of the Isopoda, for example *Armadillidium vulgare*, *Oniscus asellus*, *Porcellio scaber*;

from the order of the Isoptera, for example, *Coptotermes* spp., e.g. *Coptotermes formosanus*, *Cornitermes cumulans*, *Cryptotermes* spp., *Incisitermes* spp., *Kalotermes* spp., *Microtermes obesi*, *Nasutitermis* spp., *Odontotermes* spp., *Porotermes* spp., *Reticulitermes* spp., e.g. *Reticulitermes flavipes*, *Reticulitermes hesperus*;

from the order of the Lepidoptera, for example *Achroia grisella*, *Acronicta major*, *Adoxophyes* spp., e.g. *Adoxophyes orana*, *Aedia leucomelas*, *Agrotis* spp., e.g. *Agrotis segetum*, *Agrotis ipsilon*, *Alabama* spp., e.g. *Alabama argillacea*, *Amyelois transitella*, *Anarsia* spp., *Anticarsia* spp., e.g. *Anticarsia gemmatalis*, *Argyroploce* spp., *Autographa* spp., *Barathra brassicae*, *Blastodacna atra*, *Borbo cinnara*, *Bucculatrix thurberiella*, *Bupalus piniarius*, *Busseola* spp., *Cacoecia* spp., *Caloptilia theivora*, *Capua reticulana*, *Carpocapsa pomonella*, *Carposina niponensis*, *Cheimatobia brumata*, *Chilo* spp., e.g. *Chilo plejadellus*, *Chilo suppressalis*, *Choreutis pariana*, *Choristoneura* spp., *Chrysodeixis chalcites*, *Clysia ambiguella*, *Cnaphalocerus* spp., *Cnapha-* locrocis medinalis, Cnephasia spp., Conopomorpha spp., Conotrachelus spp., Copitarsia spp., Cydia spp., e.g. Cydia nigricana, Cydia pomonella, Dalaca noctuides, Diaphania spp., Diparopsis spp., Diatraea saccharalis, Dioryctria spp., e.g. Dioryctria zimmermani, Earias spp., Ecdytolopha aurantium, Elasmopalpus lignosellus, Eldana saccharina, Ephestia spp., e.g. Ephestia elutella, Ephestia kuehniella, Epinotia spp., Epiphyas postvittana, Erannis spp., Erschoviella musculana, Etiella spp., Eudocima spp., Eulia spp., Eupoecilia ambiguella, Euproctis spp., e.g. Euproctis chrysorrhoea, Euxoa spp., Feltia spp., Galleria mellonella, Gracillaria spp., Grapholitha spp., e.g. Grapholita molesta, Grapholita prunivora, Hedylepta spp., Helicoverpa spp., e.g. Helicoverpa armigera, Helicoverpa zea, Heliothis spp., e.g. Heliothis virescens, Hofmannophila pseudospretella, Homoeosoma spp., Homona spp., Hyponomeuta padella, Kakivoria flavofasciata, Lampides spp., Laphygma spp., Laspeyresia molesta, Leucinodes orbonalis, Leucoptera spp., e.g. Leucoptera coffeella, Lithocolletis spp., e.g. Lithocolletis blancardella, Lithophane antennata, Lobesia spp., e.g. Lobesia botrana, Loxagrotis albicosta, Lymantria spp., e.g. Lymantria dispar, Lyonetia spp., e.g. Lyonetia clerkella, Malacosoma neustria, Maruca testulalis, Mamestra brassicae, Melanitis leda, Mocis spp., Monopis obviella, Mythimna separata, Nemapogon cloacellus, Nymphula spp., Oiketicus spp., Omphisa spp., Operophtera spp., Oria spp., Orthaga spp., Ostrinia spp., e.g. Ostrinia nubilalis, Panolis flammea, Parnara spp., Pectinophora spp., e.g. Pectinophora gossypiella, Perileucoptera spp., Phthorimaea spp., e.g. Phthorimaea operculella, Phyllocnistis citrella, Phyllonorycter spp., e.g. Phyllonorycter blancardella, Phyllonorycter crataegella, Pieris spp., e.g. Pieris rapae, Platynota stultana, Plodia interpunctella, Plusia spp., Plutella xylostella (=Plutella maculipennis), Podesia spp., e.g. Podesia syringae, Prays spp., Prodenia spp., Protoparce spp., Pseudaletia spp., e.g. Pseudaletia unipuncta, Pseudoplusia includens, Pyrausta nubilalis, Rachiplusia nu, Schoenobius spp., e.g. Schoenobius bipunctifer, Scirpophaga spp., e.g. Scirpophaga innotata, Scotia segetum, Sesamia spp., e.g. Sesamia inferens, Sparganothis spp., Spodoptera spp., e.g. Spodoptera eradiana, Spodoptera exigua, Spodoptera frugiperda, Spodoptera praefica, Stathmopoda spp., Stenoma spp., Stomopteryx subsecivella, Synanthedon spp., Tecia solanivora, Thaumetopoea spp., Thermesia gemmatalis, Tinea cloacella, Tinea pellionella, Tineola bisselliella, Tortrix spp., Trichophaga tapetzella, Trichoplusia spp., e.g. Trichoplusia ni, Tryporyza incertulas, Tuta absoluta, Virachola spp.;

from the order of the Orthoptera or Saltatoria, for example Acheta domesticus, Dichroplus spp., Gryllotalpa spp., e.g. Gryllotalpa gryllotalpa, Hieroglyphus spp., Locusta spp., e.g. Locusta migratoria, Melanoplus spp., e.g. Melanoplus devastator, Paratlanticus ussuriensis, Schistocerca gregaria;

from the order of the Phthiraptera, for example Damalinia spp., Haematopinus spp., Linognathus spp., Pediculus spp., Phylloxera vastatrix, Phthirus pubis, Trichodectes spp.;

from the order of the Psocoptera, for example Lepinotus spp., Liposcelis spp.;

from the order of the Siphonaptera, for example Ceratophyllus spp., Ctenocephalides spp., e.g. Ctenocephalides canis, Ctenocephalides felis, Pulex irritans, Tunga penetrans, Xenopsylla cheopis;

from the order of the Thysanoptera, for example Anaphothrips obscurus, Baliothrips biformis, Chaetanaphothrips leeuweni, Drepanothrips reuteri, Enneothrips flavens, Frankliniella spp., e.g. Frankliniella fusca, Frankliniella occidentalis, Frankliniella schultzei, Frankliniella tritici, Frankliniella vaccinii, Frankliniella williamsi, Haplothrips spp., Heliothrips spp., Hercinothrips femoralis, Kakothrips spp., Rhipiphorothrips cruentatus, Scirtothrips spp., Taeniothrips cardamomi, Thrips spp., e.g. Thrips palmi, Thrips tabaci;

from the order of the Zygentoma (=Thysanura), for example Ctenolepisma spp., Lepisma saccharina, Lepismodes inquilinus, Thermobia domestica;

from the class of the Symphyla, for example Scutigerella spp., e.g. Scutigerella immaculata; pests from the phylum of the Mollusca, for example from the class of the Bivalvia, e.g. Dreissena spp.;

and from the class of the Gastropoda, for example Arion spp., e.g. Arion ater rufus, Biomphalaria spp., Bulinus spp., Deroceras spp., e.g. Deroceras laeve, Galba spp., Lymnaea spp., Oncomelania spp., Pomacea spp., Succinea spp.;

plant pests from the phylum of the Nematoda, i.e. phytoparasitic nematodes, in particular Aglenchus spp., for example Aglenchus agricola, Anguina spp., e.g. Anguina tritici, Aphelenchoides spp., e.g. Aphelenchoides arachidis, Aphelenchoides fragariae, Belonolaimus spp., e.g. Belonolaimus gracilis, Belonolaimus longicaudatus, Belonolaimus nortoni, Bursaphelenchus spp., e.g. Bursaphelenchus cocophilus, Bursaphelenchus eremus, Bursaphelenchus xylophilus, Cacopaurus spp., e.g. Cacopaurus pestis, Criconemella spp., e.g. Criconemella curvata, Criconemella onoensis, Criconemella ornata, Criconemella rusium, Criconemella xenoplax (=Mesocriconema xenoplax), Criconemoides spp., e.g. Criconemoides femiae, Criconemoides onoense, Criconemoides omatum, Ditylenchus spp., e.g. Ditylenchus dipsaci, Dolichodorus spp., Globodera spp., e.g. Globodera pallida, Globodera rostochiensis, Helicotylenchus spp., e.g. Helicotylenchus dihystera, Hemicriconemoides spp., Hemicycliophora spp., Heterodera spp., e.g. Heterodera avenae, Heterodera glycines, Heterodera schachtii, Hirschmaniella spp., Hoplolaimus spp., Longidorus spp., e.g. Longidorus africanus, Meloidogyne spp., e.g. Meloidogyne chitwoodi, Meloidogyne fallax, Meloidogyne hapla, Meloidogyne incognita, Meloinema spp., Nacobbus spp., Neotylenchus spp., Paralongidorus spp., Paraphelenchus spp., Paratrichodorus spp., e.g. Paratrichodorus minor, Paratylenchus spp., Pratylenchus spp., e.g. Pratylenchus penetrans, Pseudohalenchus spp., Psilenchus spp., Punctodera spp., Quinisulcius spp., Radopholus spp., e.g. Radopholus citrophilus, Radopholus similis, Rotylenchulus spp., Rotylenchus spp., Scutellonema spp., Subanguina spp., Trichodorus spp., e.g. Trichodorus obtusus, Trichodorus primitivus, Tylenchorhynchus spp., e.g. Tylenchorhynchus annulatus, Tylenchulus spp., e.g. Tylenchulus semipenetrans, Xiphinema spp., e.g. Xiphinema index.

The compounds of the formula (I) can, as the case may be, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (mycoplasma-like organisms) and RLO (rickettsia-like organisms). They can, as the case may be, also be used as intermediates or precursors for the synthesis of other active compounds.

Formulations

The present invention further relates to formulations and application forms prepared therefrom as pesticides, for example drench, drip and spray liquors, comprising at least one compound of the formula (I). Optionally, the application forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulfate or diammonium hydrogenphosphate and/or retention promoters, for example dioctyl sulfosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemical active compounds.

Preference is given to formulations or application forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are produced in a known manner, for example by mixing the compounds of the formula (I) with auxiliaries, for example extenders, solvents and/or solid carriers and/or other auxiliaries, for example surfactants. The formulations are produced either in suitable facilities or else before or during application.

The auxiliaries used may be substances suitable for imparting special properties, such as certain physical, technical and/or biological properties, to the formulation of the compounds of the formula (I), or to the application forms prepared from these formulations (for example ready-to-use pesticides such as spray liquors or seed-dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulfones and sulfoxides (such as dimethyl sulfoxide).

If the extender used is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

In principle, it is possible to use all suitable solvents. Examples of suitable solvents are aromatic hydrocarbons, for example xylene, toluene or alkylnaphthalenes, chlorinated aromatic or chlorinated aliphatic hydrocarbons, for example chlorobenzene, chloroethylene or methylene chloride, aliphatic hydrocarbons, for example cyclohexane, paraffins, petroleum fractions, mineral and vegetable oils, alcohols, for example methanol, ethanol, isopropanol, butanol or glycol and their ethers and esters, ketones, for example acetone, methyl ethyl ketone, methyl isobutyl ketone or cyclohexanone, strongly polar solvents, for example dimethyl sulfoxide, and water.

In principle, it is possible to use all suitable carriers. Suitable carriers include more particularly the following: e.g. ammonium salts and natural, finely ground rocks, such as kaolins, aluminas, talc, chalk, quartz, attapulgite, montmorillonite or diatomaceous earth, and synthetic, finely ground rocks, such as highly disperse silica, aluminium oxide and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable extenders or carriers are those which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulfonic acid, salts of phenolsulfonic acid or naphthalenesulfonic acid, polycondensates of ethylene oxide with fatty alcohols or with fatty acids or with fatty amines, with substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolysates, lignosulfite waste liquors and methylcellulose. The presence of a surfactant is advantageous if one of the compounds of the formula (I) and/or one of the inert carriers is insoluble in water and if the application takes place in water.

Further auxiliaries which may be present in the formulations and the application forms derived therefrom include dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and application forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, and natural phospholipids such as cephalins and lecithins and synthetic phospholipids. Further auxiliaries may be mineral and vegetable oils.

It is possible if appropriate for still further auxiliaries to be present in the formulations and the application forms derived therefrom. Examples of such additives are fragrances, protective colloids, binders, adhesives, thickeners, thixotropic agents, penetrants, retention promoters, stabilizers, sequestrants, complexing compositions, humectants, spreaders. In general, the compounds of the formula (I) can be combined with any solid or liquid additive commonly used for formulation purposes.

Useful retention promoters include all those substances which reduce dynamic surface tension, for example dioctyl sulfosuccinate, or increase viscoelasticity, for example hydroxypropylguar polymers.

Useful penetrants in the present context are all those substances which are typically used to improve the penetration of agrochemical active compounds into plants. Penetrants are defined in this context by their ability to penetrate from the (generally aqueous) application liquor and/or from the spray coating into the cuticle of the plant and hence to increase the mobility of the active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulfate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the application forms prepared from the formulations (in particular pesticides) may vary within wide ranges. The concentration of the compound of the formula (I) in the application forms may typically be between 0.00000001% and 95% by weight of the compound of the formula (I), preferably between 0.00001% and 1% by weight, based on the weight of the application form. Application is accomplished in a customary manner appropriate for the application forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active compound combinations of this kind can improve plant growth and/or tolerance to abiotic factors, for example high or low temperatures, to drought or to elevated levels of water or soil salinity. It is also possible to improve flowering and fruiting performance, optimize germination capacity and root development, facilitate harvesting and improve harvest yields, influence maturation, improve the quality and/or the nutritional value of the harvested products, prolong storage life and/or improve the processibility of the harvested products.

In addition, the compounds of the formula (I) may be present in a mixture with other active compounds or semiochemicals such as attractants and/or bird repellents and/or plant activators and/or growth regulators and/or fertilizers. Likewise, the compounds of the formula (I) can be used to improve plant properties, for example growth, yield and quality of the harvested material.

In a particular embodiment according to the invention, the compounds of the formula (I) are present in formulations or in the application forms prepared from these formulations in a mixture with further compounds, preferably those as described below.

If one of the compounds mentioned below can occur in different tautomeric forms, these forms are also included even if not explicitly mentioned in each case. All the mixing components mentioned, as the case may be, may also form salts with suitable bases or acids if they are capable of doing so on the basis of their functional groups.

Insecticides/Acaricides/Nematicides

The active compounds specified here by their common names are known and are described for example in "The Pesticide Manual" (16th ed., British Crop Protection Council 2012) or can be searched for on the Internet (e.g. http://www.alanwood.net/pesticides). The classification is based on the IRAC Mode of Action Classification Scheme applicable at the time of filing of this patent application.

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion.

(2) GABA-gated chloride channel blockers, for example cyclodiene-organochlorines, e.g. chlordane and endosulfan or phenylpyrazoles (fiproles), e.g. ethiprole and fipronil.

(3) Sodium channel modulators, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomer], deltamethrin, empenthrin [(EZ)-(1R) isomer], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomer], tralomethrin and transfluthrin or DDT or methoxychlor.

(4) Nicotinic acetylcholine receptor (nAChR) competitive modulators, for example neonicotinoids, e.g. acetamiprid, clothianidin, dinotefuran, imidacloprid, nitenpyram, thiacloprid and thiamethoxam or nicotine or sulfoxaflor or flupyradifurone.

(5) Nicotinic acetylcholine receptor (nAChR) allosteric modulators, for example spinosyns, e.g. spinetoram and spinosad.

(6) Glutamate-gated chloride channel (GluCl) allosteric modulators, for example avermectins/milbemycins, e.g. abamectin, emamectin benzoate, lepimectin and milbemectin.

(7) Juvenile hormone mimetics, for example juvenile hormone analogues, e.g. hydroprene, kinoprene and methoprene or fenoxycarb or pyriproxyfen.

(8) Miscellaneous non-specific (multisite) inhibitors, for example alkyl halides, e.g. methyl bromide and other alkyl halides; or chloropicrin or sulfuryl fluoride or borax or tartar emetic or methyl isocyanate generator, e.g. diazomet and metam.

(9) Chordotonal organ modulators, e.g. pymetrozine or flonicamide.

(10) Mite growth inhibitors, for example clofentezine, hexythiazox and diflovidazin or etoxazole.

(11) Microbial disruptors of the insect gut membrane, for example *Bacillus thuringiensis* subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis* and B.t. plant proteins: Cry1Ab, Cry1Ac, Cry1Fa, Cry1A.105, Cry2Ab, VIP3A, mCry3A, Cry3Ab, Cry3Bb, Cry34Abl/35Abl.

(12) Inhibitors of mitochondrial ATP synthase, such as ATP disruptors, for example diafenthiuron or organotin compounds, e.g. azocyclotin, cyhexatin and fenbutatin oxide or propargite or tetradifon.

(13) Uncouplers of oxidative phosphorylation via disruption of the proton gradient, for example chlorfenapyr, DNOC and sulfluramid.

(14) Nicotinic acetylcholine receptor channel blockers, for example bensultap, cartap hydrochloride, thiocyclam, and thiosultap-sodium.

(15) Inhibitors of chitin biosynthesis, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting disruptors (especially in the case of Diptera), for example cyromazine.

(18) Ecdysone receptor agonists, for example chromafenozide, halofenozide, methoxyfenozide and tebufenozide.

(19) Octopamine receptor agonists, for example amitraz.

(20) Mitochondrial complex III electron transport inhibitors, for example hydramethylnon or acequinocyl or fluacrypyrim.

(21) Mitochondrial complex I electron transport inhibitors, for example METI acaricides, e.g. fenazaquin, fenpyroximate, pyrimidifen, pyridaben, tebufenpyrad and tolfenpyrad or rotenone (Derris).

(22) Voltage-dependent sodium channel blockers, for example indoxacarb or metaflumizone.

(23) Inhibitors of acetyl CoA carboxylase, for example tetronic and tetramic acid derivatives, e.g. spirodiclofen, spiromesifen and spirotetramat.

(24) Mitochondrial complex IV electron transport inhibitors, for example phosphines, e.g. aluminium phosphide, calcium phosphide, phosphine and zinc phosphide, or cyanides, calcium cyanide, potassium cyanide and sodium cyanide.

(25) Mitochondrial complex II electron transport inhibitors, for example beta-keto nitrile derivatives, e.g. cyenopyrafen and cyflumetofen and carboxanilides, for example pyflubumide.

(28) Ryanodine receptor modulators, for example diamides, e.g. chlorantraniliprole, cyantraniliprole and flubendiamide, further active compounds, for example afidopyropen, afoxolaner, azadirachtin, benclothiaz, benzoximate, bifenazate, broflanilide, bromopropylate, chinomethionat, chloroprallethrin, cryolite, cyclaniliprole, cycloxaprid, cyhalodiamide, dicloromezotiaz, dicofol, epsilon metofluthrin, epsilon momfluthrin, flometoquin, fluazaindolizine, fluensulfone, flufenerim, flufenoxystrobin, flufiprole, fluhexafon, fluopyram, fluralaner, fluxametamide, fufenozide, guadipyr, heptafluthrin, imidaclothiz, iprodione, kappa bifenthrin, kappa tefluthrin, lotilaner, meperfluthrin, paichongding, pyridalyl, pyrifluquinazon, pyriminostrobin, spirobudiclofen, tetramethylfluthrin, tetraniliprole, tetrachlorantraniliprole, tioxazafen, thiofluoximate, triflumezopyrim and iodomethane; additionally preparations based on *Bacillus firmus* (I-1582, BioNeem, Votivo), and the following compounds: 1-{2-fluoro-4-methyl-5-[(2,2,2-trifluoroethyl)sulfinyl]phenyl}-3-(trifluoromethyl)-1H-1,2,4-triazole-5-amine (known from WO2006/043635) (CAS 885026-50-6), {1'-[(2E)-3-(4-chlorophenyl)prop-2-en-1-yl]-5-fluorospiro[indole-3,4'-piperidine]-1(2H)-yl}(2-chloropyridin-4-yl) methanone (known from WO2003/106457) (CAS 637360-23-7), 2-chloro-N-[2-{1-[(2E)-3-(4-chlorophenyl)prop-2-en-1-yl]piperidin-4-yl}-4-(trifluoromethyl)phenyl] isonicotinamide (known from WO2006/003494) (CAS 872999-66-1), 3-(4-chloro-2,6-dimethylphenyl)-4-hydroxy-8-methoxy-1,8-diazaspiro[4.5]dec-3-en-2-one (known from WO 2010052161) (CAS 1225292-17-0), 3-(4-chloro-2,6-dimethylphenyl)-8-methoxy-2-oxo-1,8-diazaspiro[4.5]dec-3-en-4-yl ethylcarbonate (known from EP 2647626) (CAS-1440516-42-6), 4-(but-2-yn-1-yloxy)-6-(3,5-dimethylpiperidin-1-yl)-5-fluoropyrimidine (known from WO2004/099160) (CAS 792914-58-0), PF1364 (known from JP2010/018586) (CAS Reg. No. 1204776-60-2), N-[(2E)-1-[(6-chloropyridin-3-yl)methyl]pyridin-2(1H)-ylidene]-2,2,2-trifluoroacetamide (known from WO2012/029672) (CAS 1363400-41-2), (3E)-3-[1-[(6-chloro-3-pyridyl)methyl]-2-pyridylidene]-1,1,1-trifluoropropan-2-one (known from WO2013/144213) (CAS 1461743-15-6), N-[3-(benzylcarbamoyl)-4-chlorophenyl]-1-methyl-3-(pentafluoroethyl)-4-(trifluoromethyl)-1H-pyrazole-5-carboxamide (known from WO2010/051926) (CAS 1226889-14-0), 5-bromo-4-chloro-N-[4-chloro-2-methyl-6-(methylcarbamoyl)phenyl]-2-(3-chloro-2-pyridyl)pyrazole-3-carboxamide (known from CN103232431) (CAS 1449220-44-3), 4-[5-(3,5-dichlorophenyl)-4,5-dihydro-5-(trifluoromethyl)-3-isoxazolyl]-2-methyl-N-(cis-1-oxido-3-thietanyl)benzamide, 4-[5-(3,5-dichlorophenyl)-4,5-dihydro-5-(trifluoromethyl)-3-isoxazolyl]-2-methyl-N-(trans-1-oxido-3-thietanyl)benzamide and 4-[(5 S)-5-(3,5-dichlorophenyl)-4,5-dihydro-5-(trifluoromethyl)-3-isoxazolyl]-2-methyl-N-(cis-1-oxido-3-thietanyl)benzamide (known from WO 2013/050317 A1) (CAS 1332628-83-7), N-[3-chloro-1-(3-pyridinyl)-1H-pyrazol-4-yl]-N-ethyl-3-[(3,3,3-trifluoropropyl)sulfinyl]propanamide, (+)—N-[3-chloro-1-(3-pyridinyl)-1H-pyrazol-4-yl]-N-ethyl-3-[(3,3,3- trifluoropropyl)sulfinyl]propanamide and (−)—N-[3-chloro-1-(3-pyridinyl)-1H-pyrazol-4-yl]-N-ethyl-3-[(3,3,3-trifluoropropyl)sulfinyl]propanamide (known from WO 2013/162715 A2, WO 2013/162716 A2, US 2014/0213448 A1) (CAS 1477923-37-7), 5-[[(2E)-3-chloro-2-propen-1-yl]amino]-1-[2,6-dichloro-4-(trifluoromethyl)phenyl]-4-[(trifluoromethyl)sulfinyl]-1H-pyrazole-3-carbonitrile (known from CN 101337937 A) (CAS 1105672-77-2), 3-bromo-N-[4-chloro-2-methyl-6-[(methylamino)thioxomethyl]phenyl]-1-(3-chloro-2-pyridinyl)-1H-pyrazole-5-carboxamide (Liudaibenjiaxuanan, known from CN 103109816 A) (CAS 1232543-85-9); N-[4-chloro-2-[[(1,1-dimethylethyl)amino]carbonyl]-6-methylphenyl]-1-(3-chloro-2-pyridinyl)-3-(fluoromethoxy)-1H-pyrazole-5-carboxamide (known from WO 2012/034403 A1) (CAS 1268277-22-0), N-[2-(5-amino-1,3,4-thiadiazol-2-yl)-4-chloro-6-methylphenyl]-3-bromo-1-(3-chloro-2-pyridinyl)-1H-pyrazole-5-carboxamide (known from WO 2011/085575 A1) (CAS 1233882-22-8), 4-[3-[2,6-dichloro-4-[(3,3-dichloro-2-propen-1-yl)oxy]phenoxy]propoxy]-2-methoxy-6-(trifluoromethyl)pyrimidine (known from CN 101337940 A) (CAS 1108184-52-6); (2E)- and 2(Z)-2-[2-(4-cyanophenyl)-1-[3-(trifluoromethyl)phenyl]ethylidene]-N-[4-(difluoromethoxy)phenyl]hydrazinecarboxamide (known from CN 101715774 A) (CAS 1232543-85-9); cyclopropanecarboxylic acid 3-(2,2-dichloroethenyl)-2,2-dimethyl-4-(1H-benzimidazol-2-yl)phenyl ester (known from CN 103524422 A) (CAS 1542271-46-4); (4aS)-7-chloro-2,5-dihydro-2-[[(methoxycarbonyl)[4-[(trifluoromethyl)thio]phenyl]amino]carbonyl]indeno[1,2-e][1,3,4]oxadiazine-4a (3H)-carboxylic acid methyl ester (known from CN 102391261 A) (CAS 1370358-69-2); 6-deoxy-3-O-ethyl-2,4-di-O-methyl-1-[N-[4-[1-[4-(1,1,2,2,2-pentafluoroethoxy)phenyl]-1H-1,2,4-triazol-3-yl]phenyl]carbamate]-α-L-mannopyranose (known from US 2014/0275503 A1) (CAS 1181213-14-8); 8-(2-cyclopropylmethoxy-4-trifluoromethylphenoxy)-3-(6-trifluoromethylpyridazin-3-yl)-3-azabicyclo[3.2.1]octane (CAS 1253850-56-4), (8-anti)-8-(2-cyclopropylmethoxy-4-trifluoromethylphenoxy)-3-(6-trifluoromethylpyridazin-3-yl)-3-azabicyclo[3.2.1]octane (CAS 933798-27-7), (8-syn)-8-(2-cyclopropylmethoxy-4-trifluoromethylphenoxy)-3-(6-trifluoromethylpyridazin-3-yl)-3-azabicyclo[3.2.1]octane (known from WO 2007040280 A1, WO 2007040282 A1) (CAS 934001-66-8), N-[3-chloro-1-(3-pyridinyl)-1H-pyrazol-4-yl]-N-ethyl-3-[(3,3,3-trifluoropropyl)thio]propanamide (known from WO 2015/058021 A1, WO 2015/058028 A1) (CAS 1477919-27-9) and N-[4-(aminothioxomethyl)-2-methyl-6-[(methylamino)carbonyl]phenyl]-3-bromo-1-(3-chloro-2-pyridinyl)-1H-pyrazole-5-carboxamide (known from CN 103265527 A) (CAS 1452877-50-7).

Fungicides

The active compounds specified hereby their common names are known and described, for example, in "Pesticide Manual" (16th Ed. British Crop Protection Council) or searchable on the Internet (for example: http://www.alanwood.net/pesticides).

All the mixing components mentioned in classes (1) to (15), as the case may be, may form salts with suitable bases or acids if they are capable of doing so on the basis of their functional groups. All the fungicidal mixing components mentioned in classes (1) to (15), as the case may be, may include tautomeric forms.

1) Inhibitors of ergosterol biosynthesis, for example (1.001) cyproconazole, (1.002) difenoconazole, (1.003) epoxiconazole, (1.004) fenhexamid, (1.005) fenpropidin, (1.006) fenpropimorph, (1.007) fenpyrazamine, (1.008) fluquinconazole, (1.009) flutriafol, (1.010) imazalil, (1.011) imazalil sulfate, (1.012) ipconazole, (1.013) metconazole, (1.014) myclobutanil, (1.015) paclobutrazol, (1.016) prochloraz, (1.017) propiconazole, (1.018) prothioconazole, (1.019) pyrisoxazole, (1.020) spiroxamine, (1.021) tebuconazole, (1.022) tetraconazole, (1.023) triadimenol, (1.024) tridemorph, (1.025) triticonazole, (1.026) (1R,2S,5S)-5-(4-chlorobenzyl)-2-(chloromethyl)-2-methyl-1-(1H-1,2,4-triazol-1-ylmethyl)cyclopentanol, (1.027) (1S,2R,5R)-5-(4-chlorobenzyl)-2-(chloromethyl)-2-methyl-1-(1H-1,2,4-triazol-1-ylmethyl)cyclopentanol, (1.028) (2R)-2-(1-chlorocyclopropyl)-4-[(1R)-2,2-dichlorocyclopropyl]-1-(1H-1,2,4-triazol-1-yl)butan-2-ol, (1.029) (2R)-2-(1-chlorocyclopropyl)-4-[(1S)-2,2-dichlorocyclopropyl]-1-(1H-1,2,4-triazol-1-yl)butan-2-ol, (1.030) (2R)-2-[4-(4-chlorophenoxy)-2-(trifluoromethyl)phenyl]-1-(1H-1,2,4-triazol-1-yl)propan-2-ol, (1.031) (2S)-2-(1-chlorocyclopropyl)-4-[(1R)-2,2-dichlorocyclopropyl]-1-(1H-1,2,4-triazol-1-yl)butan-2-ol, (1.032) (2S)-2-(1-chlorocyclopropyl)-4-[(1 S)-2,2-dichlorocyclopropyl]-1-(1H-1,2,4-triazol-1-yl)butan-2-ol, (1.033) (2S)-2-[4-(4-chlorophenoxy)-2-(trifluoromethyl)phenyl]-1-(1H-1,2,4-triazol-1-yl)propan-2-ol, (1.034) (R)-[3-(4-chloro-2-fluorophenyl)-5-(2,4-difluorophenyl)-1,2-oxazol-4-yl](pyridin-3-yl)methanol, (1.035) (S)-[3-(4-chloro-2-fluorophenyl)-5-(2,4-difluorophenyl)-1,2-oxazol-4-yl](pyridin-3-yl)methanol, (1.036) [3-(4-chloro-2-fluorophenyl)-5-(2,4-difluorophenyl)-1,2-oxazol-4-yl](pyridin-3-yl)methanol, (1.037) 1-({(2R,4S)-2-[2-chloro-4-(4-chlorophenoxy)phenyl]-4-methyl-1,3-dioxolan-2-yl}methyl)-1H-1,2,4-triazole, (1.038) 1-({(2S,4S)-2-[2-chloro-4-(4-chlorophenoxy)phenyl]-4-methyl-1,3-dioxolan-2-yl}methyl)-1H-1,2,4-triazole, (1.039) 1-{[3-(2-chlorophenyl)-2-(2,4-difluorophenyl)oxiran-2-yl]methyl}-1H-1,2,4-triazol-5-yl thiocyanate, (1.040) 1-{[rel(2R,3R)-3-(2-chlorophenyl)oxir-2-(2,4-difluorophenyl)oxiran-2-yl]methyl}-1H-1,2,4-triazol-5-yl thiocyanate, (1.041) 1-{[rel (2R,3S)-3-(2-chlorophenyl)-2-(2,4-difluorophenyl)oxiran-2-yl]methyl}-1H-1,2,4-triazol-5-yl thiocyanate, (1.042) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.043) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.044) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.045) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.046) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.047) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.048) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.049) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.050) 2-[1-(2,4-dichlorophenyl)-5-hydroxy-2,6,6-trimethylheptan-4-yl]-2,4-dihydro-3H-1,2,4-triazole-3-thione, (1.051) 2-[2-chloro-4-(2,4-dichlorophenoxy)phenyl]-1-(1H-1,2,4-triazol-1-yl)propan-2-ol, (1.052) 2-[2-chloro-4-(4-chlorophenoxy)phenyl]-1-(1H-1,2,4-triazol-1-yl)butan-2-ol, (1.053) 2-[4-(4-chlorophenoxy)-2-(trifluoromethyl)phenyl]-1-(1H-1,2,4-triazol-1-yl)butan-2-ol, (1.054) 2-[4-(4-chlorophenoxy)-2-(trifluoromethyl)phenyl]-1-(1H-1,2,4-triazol-1-yl)pentan-2-ol, (1.055) 2-[4-(4-chlorophenoxy)-2-(trifluoromethyl)

phenyl]-1-(1H-1,2,4-triazol-1-yl)propan-2-ol, (1.056) 2-{[3-(2-chlorophenyl)-2-(2,4-difluorophenyl)oxiran-2-yl]methyl}-2,4-dihydro-3H-1,2,4-triazole-3-thione, (1.057) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.058) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.059) 5-(4-chlorobenzyl)-2-(chloromethyl)-2-methyl-1-(1H-1,2,4-triazol-1-ylmethyl)cyclopentanol, (1.060) 5-(allylsulfanyl)-1-{[3-(2-chlorophenyl)-2-(2,4-difluorophenyl)oxiran-2-yl]methyl}-1H-1,2,4-triazole, (1.061) 5-(allylsulfanyl)-1-{[rel(2R,3R)-3-(2-chlorophenyl)-2-(2,4-difluorophenyl)oxiran-2-yl]methyl}-H-1,2,4-triazole, (1.062) 5-(allylsulfanyl)-1-{[rel(2R,3S)-3-(2-chlorophenyl)-2-(2,4-difluorophenyl)oxiran-2-yl]methyl})-1H-1,2,4-triazole, (1.063) N'-(2,5-dimethyl-4-{[3-(1,1,2,2-tetrafluoroethoxy)phenyl]sulfanyl}phenyl)-N-ethyl-N-methylimidoformamide, (1.064) N'-(2,5-dimethyl-4-{[3-(2,2,2-trifluoroethoxy)phenyl]sulfanyl}phenyl)-N-ethyl-N-methylimidoformamide, (1.065) N'-(2,5-dimethyl-4-{[3-(2,2,3,3-tetrafluoropropoxy)phenyl]sulfanyl}phenyl)-N-ethyl-N-methylimidoformamide, (1.066) N'-(2,5-dimethyl-4-{[3-(pentafluoroethoxy)phenyl]sulfanyl}phenyl)-N-ethyl-N-methylimidoformamide, (1.067) N'-(2,5-dimethyl-4-{3-[(1,1,2,2-tetrafluoroethyl)sulfanyl]phenoxy}phenyl)-N-ethyl-N-methylimidoformamide, (1.068) N'-(2,5-dimethyl-4-{3-[(2,2,2-trifluoroethyl)sulfanyl]phenoxy}phenyl)-N-ethyl-N-methylimidoformamide, (1.069) N'-(2,5-dimethyl-4-{3-[(2,2,3,3-tetrafluoropropyl)sulfanyl]phenoxy}phenyl)-N-ethyl-N-methylimidoformamide, (1.070) N'-(2,5-dimethyl-4-{3-[(pentafluoroethyl)sulfanyl]phenoxy}phenyl)-N-ethyl-N-methylimidoformamide, (1.071) N'-(2,5-dimethyl-4-phenoxyphenyl)-N-ethyl-N-methylimidoformamide, (1.072) N'-(4-{[3-(difluoromethoxy)phenyl]sulfanyl}-2,5-dimethylphenyl)-N-ethyl-N-methylimidoformamide, (1.073) N'-(4-{3-[(difluoromethyl)sulfanyl]phenoxy}-2,5-dimethylphenyl)-N-ethyl-N-methylimidoformamide, (1.074) N'-[5-bromo-6-(2,3-dihydro-1H-inden-2-yloxy)-2-methylpyridin-3-yl]-N-ethyl-N-methylimidoformamide, (1.075) N'-{4-[(4,5-dichloro-1,3-thiazol-2-yl)oxy]-2,5-dimethylphenyl}-N-ethyl-N-methylimidoformamide, (1.076) N'-{5-bromo-6-[(1R)-1-(3,5-difluorophenyl)ethoxy]-2-methylpyridin-3-yl}-N-ethyl-N-methylimidoformamide, (1.077) N'-{5-bromo-6-[(1S)-1-(3,5-difluorophenyl)ethoxy]-2-methylpyridin-3-yl}-N-ethyl-N-methylimidoformamide, (1.078) N'-{5-bromo-6-[(cis-4-isopropylcyclohexyl)oxy]-2-methylpyridin-3-yl}-N-ethyl-N-methylimidoformamide, (1.079) N'-{5-bromo-6-[(trans-4-isopropylcyclohexyl)oxy]-2-methylpyridin-3-yl}-N-ethyl-N-methylimidoformamide, (1.080) N'-{5-bromo-6-[1-(3,5-difluorophenyl)ethoxy]-2-methylpyridin-3-yl}-N-ethyl-N-methylimidoformamide, (1.081) mefentrifluconazole, (1.082) ipfentrifluconazole.

2) Inhibitors of the respiratory chain in complex I or II, for example (2.001) benzovindiflupyr, (2.002) bixafen, (2.003) boscalid, (2.004) carboxin, (2.005) fluopyram, (2.006) flutolanil, (2.007) fluxapyroxad, (2.008) furametpyr, (2.009) isofetamid, (2.010) isopyrazam (anti-epimeric enantiomer 1R,4S,9S), (2.011) isopyrazam (anti-epimeric enantiomer 1S,4R,9R), (2.012) isopyrazam (anti-epimeric racemate 1RS,4SR,9SR), (2.013) isopyrazam (mixture of the syn-epimeric racemate 1RS,4SR,9RS and the anti-epimeric racemate 1RS,4SR,9SR), (2.014) isopyrazam (syn-epimeric enantiomer 1R,4S,9R), (2.015) isopyrazam (syn-epimeric enantiomer 1S,4R,9S), (2.016) isopyrazam (syn-epimeric racemate 1RS,4SR,9RS), (2.017) penflufen, (2.018) penthiopyrad, (2.019) pydiflumetofen, (2.020) pyraziflumid, (2.021) sedaxane, (2.022) 1,3-dimethyl-N-(1,1,3-trimethyl-2,3-dihydro-1H-inden-4-yl)-1H-pyrazole-4-carboxamide, (2.023) 1,3-dimethyl-N-[(3R)-1,1,3-trimethyl-2,3-dihydro-1H-inden-4-yl]-1H-pyrazole-4-carboxamide, (2.024) 1,3-dimethyl-N-[(3S)-1,1,3-trimethyl-2,3-dihydro-1H-inden-4-yl]-1H-pyrazole-4-carboxamide, (2.025) 1-methyl-3-(trifluoromethyl)-N-[2'-(trifluoromethyl)biphenyl-2-yl]-1H-pyrazole-4-carboxamide, (2.026) 2-fluoro-6-(trifluoromethyl)-N-(1,1,3-trimethyl-2,3-dihydro-1H-inden-4-yl)benzamide, (2.027) 3-(difluoromethyl)-1-methyl-N-(1,1,3-trimethyl-2,3-dihydro-1H-inden-4-yl)-1H-pyrazole-4-carboxamide, (2.028) 3-(difluoromethyl)-1-methyl-N-[(3R)-1,1,3-trimethyl-2,3-dihydro-1H-inden-4-yl]-1H-pyrazole-4-carboxamide, (2.029) 3-(difluoromethyl)-1-methyl-N-[(3S)-1,1,3-trimethyl-2,3-dihydro-1H-inden-4-yl]-1H-pyrazole-4-carboxamide, (2.030) 3-(difluoromethyl)-N-(7-fluoro-1,1,3-trimethyl-2,3-dihydro-1H-inden-4-yl)-1-methyl-1H-pyrazole-4-carboxamide, (2.031) 3-(difluoromethyl)-N-[(3R)-7-fluoro-1,1,3-trimethyl-2,3-dihydro-1H-inden-4-yl]-1-methyl-1H-pyrazole-4-carboxamide, (2.032) 3-(difluoromethyl)-N-[(3S)-7-fluoro-1,1,3-trimethyl-2,3-dihydro-1H-inden-4-yl]-1-methyl-1H-pyrazole-4-carboxamide, (2.033) 5,8-difluoro-N-[2-(2-fluoro-4-{[4-(trifluoromethyl)pyridin-2-yl]oxy}phenyl)ethyl]quinazolin-4-amine, (2.034) N-(2-cyclopentyl-5-fluorobenzyl)-N-cyclopropyl-3-(difluoromethyl)-5-fluoro-1-methyl-1H-pyrazole-4-carboxamide, (2.035) N-(2-tert-butyl-5-methylbenzyl)-N-cyclopropyl-3-(difluoromethyl)-5-fluoro-1-methyl-H-pyrrazole-4-carboxamide, (2.036) N-(2-tert-butylbenzyl)-N-cyclopropyl-3-(difluoromethyl)-5-fluoro-1-methyl-1H-pyrazole-4-carboxamide, (2.037) N-(5-chloro-2-ethylbenzyl)-N-cyclopropyl-3-(difluoromethyl)-5-fluoro-1-methyl-1H-pyrazole-4-carboxamide, (2.038) N-(5-chloro-2-isopropylbenzyl)-N-cyclopropyl-3-(difluoromethyl)-5-fluoro-1-methyl-1H-pyrazole-4-carboxamide, (2.039) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.040) N-[(1 S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.041) N-[1-(2,4-dichlorophenyl)-1-methoxypropan-2-yl]-3-(difluoromethyl)-1-methyl-1H-pyrazole-4-carboxamide, (2.042) N-[2-chloro-6-(trifluoromethyl)benzyl]-N-cyclopropyl-3-(difluoromethyl)-5-fluoro-1-methyl-1H-pyrazole-4-carboxamide, (2.043) N-[3-chloro-2-fluoro-6-(trifluoromethyl)benzyl]-N-cyclopropyl-3-(difluoromethyl)-5-fluoro-1-methyl-1H-pyrazole-4-carboxamide, (2.044) N-[5-chloro-2-(trifluoromethyl)benzyl]-N-cyclopropyl-3-(difluoromethyl)-5-fluoro-1-methyl-1H-pyrazole-4-carboxamide, (2.045) N-cyclopropyl-3-(difluoromethyl)-5-fluoro-1-methyl-N-[5-methyl-2-(trifluoromethyl)benzyl]-1H-pyrazole-4-carboxamide, (2.046) N-cyclopropyl-3-(difluoromethyl)-5-fluoro-N-(2-fluoro-6-isopropylbenzyl)-1-methyl-1H-pyrazole-4-carboxamide, (2.047) N-cyclopropyl-3-(difluoromethyl)-5-fluoro-N-(2-isopropyl-5-methylbenzyl)-1-methyl-1H-pyrazole-4-carboxamide, (2.048) N-cyclopropyl-3-(difluoromethyl)-5-fluoro-N-(2-isopropylbenzyl)-1-methyl-1H-pyrazole-4-carbothioamide, (2.049) N-cyclopropyl-3-(difluoromethyl)-5-fluoro-N-(2-isopropylbenzyl)-1-methyl-1H-pyrazole-4-carboxamide, (2.050) N-cyclopropyl-3-(difluoromethyl)-5-fluoro-N-(5-fluoro-2-isopropylbenzyl)-1-methyl-1H-pyrazole-4-carboxamide, (2.051) N-cyclopropyl-3-(difluoromethyl)-N-(2-ethyl-4,5-dimethylbenzyl)-5-fluoro-1-methyl-1H-pyrazole-4-carboxamide, (2.052) N-cyclopropyl-3-(difluoromethyl)-N-(2-ethyl-5-fluorobenzyl)-5-fluoro-1-methyl-1H-pyrazole-4-carboxamide, (2.053) N-cyclopropyl-3-(difluoromethyl)-N-(2-ethyl-5-methylbenzyl)-5-fluoro-1-methyl-1H-pyrazole-4-carboxamide, (2.054) N-cyclopropyl-N-(2-cyclopropyl-5-fluorobenzyl)-3-(difluoromethyl)-5-fluoro-1-methyl-1H-pyrazole-4-carboxamide, (2.055) N-cyclopropyl-N-(2-cyclopropyl-5-methylbenzyl)-3-(difluoromethyl)-5-fluoro-1-methyl-1H-pyrazole-4-carboxamide, (2.056) N-cyclopropyl-N-(2-cyclopropylbenzyl)-3-(difluoromethyl)-5-fluoro-1-methyl-1H-pyrazole-4-carboxamide.

3) Inhibitors of the respiratory chain in complex III, for example (3.001) ametoctradin, (3.002) amisulbrom, (3.003) azoxystrobin, (3.004) coumethoxystrobin, (3.005) coumoxystrobin, (3.006) cyazofamid, (3.007) dimoxystrobin, (3.008) enoxastrobin, (3.009) famoxadon, (3.010) fenamidon, (3.011) flufenoxystrobin, (3.012) fluoxastrobin, (3.013) kresoxim-methyl, (3.014) metominostrobin, (3.015) orysastrobin, (3.016) picoxystrobin, (3.017) pyraclostrobin, (3.018) pyrametostrobin, (3.019) pyraoxystrobin, (3.020) trifloxystrobin, (3.021) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.022) (2E,3Z)-5-{[1-(4-chlorophenyl)-1H-pyrazol-3-yl]oxy}-2-(methoxyimino)-N,3-dimethylpent-3-enamide, (3.023) (2R)-2-{2-[(2,5-dimethylphenoxy)methyl]phenyl}-2-methoxy-N-methylacetamide, (3.024) (2S)-2-{2-[(2,5-dimethylphenoxy)methyl]phenyl}-2-methoxy-N-methylacetamide, (3.025) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (3.026) 2-{2-[(2,5-dimethylphenoxy)methyl]phenyl}-2-methoxy-N-methylacetamide, (3.027) N-(3-ethyl-3,5,5-trimethylcyclohexyl)-3-formamido-2-hydroxybenzamide, (3.028) (2E,3Z)-5-{[1-(4-chloro-2-fluorophenyl)-1H-pyrazol-3-yl]oxy}-2-(methoxyimino)-N,3-dimethylpent-3-enamide, (3.029) methyl {5-[3-(2,4-dimethylphenyl)-1H-pyrazol-1-yl]-2-methylbenzyl}carbamate.

4) Mitosis and cell division inhibitors, for example (4.001) carbendazim, (4.002) diethofencarb, (4.003) ethaboxam, (4.004) fluopicolid, (4.005) pencycuron, (4.006) thiabendazole, (4.007) thiophanate-methyl, (4.008) zoxamide, (4.009) 3-chloro-4-(2,6-difluorophenyl)-6-methyl-5-phenylpyridazine, (4.010) 3-chloro-5-(4-chlorophenyl)-4-(2,6-difluorophenyl)-6-methylpyridazine, (4.011) 3-chloro-5-(6-chloropyridin-3-yl)-6-methyl-4-(2,4,6-trifluorophenyl)pyridazine, (4.012) 4-(2-bromo-4-fluorophenyl)-N-(2,6-difluorophenyl)-1,3-dimethyl-1H-pyrazol-5-amine, (4.013) 4-(2-bromo-4-fluorophenyl)-N-(2-bromo-6-fluorophenyl)-1,3-dimethyl-1H-pyrazol-5-amine, (4.014) 4-(2-bromo-4-fluorophenyl)-N-(2-bromophenyl)-1,3-dimethyl-1H-pyrazol-5-amine, (4.015) 4-(2-bromo-4-fluorophenyl)-N-(2-chloro-6-fluorophenyl)-1,3-dimethyl-1H-pyrazol-5-amine, (4.016) 4-(2-bromo-4-fluorophenyl)-N-(2-chlorophenyl)-1,3-dimethyl-1H-pyrazol-5-amine, (4.017) 4-(2-bromo-4-fluorophenyl)-N-(2-fluorophenyl)-1,3-dimethyl-1H-pyrazol-5-amine, (4.018) 4-(2-chloro-4-fluorophenyl)-N-(2,6-difluorophenyl)-1,3-dimethyl-1H-pyrazol-5-amine, (4.019) 4-(2-chloro-4-fluorophenyl)-N-(2-chloro-6-fluorophenyl)-1,3-dimethyl-1H-pyrazol-5-amine, (4.020) 4-(2-chloro-4-fluorophenyl)-N-(2-chlorophenyl)-1,3-dimethyl-1H-pyrazol-5-amine, (4.021) 4-(2-chloro-4-fluorophenyl)-N-(2-fluorophenyl)-1,3-dimethyl-1H-pyrazol-5-amine, (4.022) 4-(4-chlorophenyl)-5-(2,6-difluorophenyl)-3,6-dimethylpyridazine, (4.023) N-(2-bromo-6-fluorophenyl)-4-(2-chloro-4-fluorophenyl)-1,3-dimethyl-1H-pyrazol-5-amine, (4.024) N-(2-bromophenyl)-4-(2-chloro-4-fluorophenyl)-1,3-dimethyl-1H-pyrazol-5-amine, (4.025) N-(4-chloro-2,6-difluorophenyl)-4-(2-chloro-4-fluorophenyl)-1,3-dimethyl-1H-pyrazol-5-amine.

5) Compounds having capacity for multisite activity, for example (5.001) Bordeaux mixture, (5.002) captafol, (5.003) captan, (5.004) chlorthalonil, (5.005) copper hydroxide, (5.006) copper naphthenate, (5.007) copper oxide, (5.008) copper oxychloride, (5.009) copper(2+) sulfate, (5.010) dithianon, (5.011) dodin, (5.012) folpet, (5.013) mancozeb, (5.014) maneb, (5.015) metiram, (5.016) zinc metiram, (5.017) copper oxine, (5.018) propineb, (5.019) sulfur and sulfur preparations including calcium polysulfide, (5.020) thiram, (5.021) zineb, (5.022) ziram, (5.023) 6-ethyl-5,7-dioxo-6,7-dihydro-5H-pyrrolo[3',4':5,6][1,4]dithiino[2,3-c][1,2]thiazole-3-carbonitrile.

6) Compounds capable of triggering host defence, for example (6.001) acibenzolar-S-methyl, (6.002) isotianil, (6.003) probenazole, (6.004) tiadinil.

7) Amino acid and/or protein biosynthesis inhibitors, for example (7.001) cyprodinil, (7.002) kasugamycin, (7.003) kasugamycin hydrochloride hydrate, (7.004) oxytetracycline, (7.005) pyrimethanil, (7.006) 3-(5-fluoro-3,3,4,4-tetramethyl-3,4-dihydroisoquinolin-1-yl)quinoline.

(8) ATP production inhibitors, for example (8.001) silthiofam.

9) Cell wall synthesis inhibitors, for example (9.001) benthiavalicarb, (9.002) dimethomorph, (9.003) flumorph, (9.004) iprovalicarb, (9.005) mandipropamid, (9.006) pyrimorph, (9.007) valifenalate, (9.008) (2E)-3-(4-tert-butylphenyl)-3-(2-chloropyridin-4-yl)-1-(morpholin-4-yl)prop-2-en-1-one, (9.009) (2Z)-3-(4-tert-butylphenyl)-3-(2-chloropyridin-4-yl)-1-(morpholin-4-yl)prop-2-en-1-one.

10) Lipid and membrane synthesis inhibitors, for example (10.001) propamocarb, (10.002) propamocarb hydrochloride, (10.003) tolclofos-methyl.

11) Melanin biosynthesis inhibitors, for example (11.001) tricyclazole, (11.002) 2,2,2-trifluoroethyl {3-methyl-1-[(4-methylbenzoyl)amino]butan-2-yl}carbamate.

12) Nucleic acid synthesis inhibitors, for example (12.001) benalaxyl, (12.002) benalaxyl-M (kiralaxyl), (12.003) metalaxyl, (12.004) metalaxyl-M (mefenoxam).

13) Signal transduction inhibitors, for example (13.001) fludioxonil, (13.002) iprodione, (13.003) procymidone, (13.004) proquinazid, (13.005) quinoxyfen, (13.006) vinclozolin.

14) Compounds that can act as uncouplers, for example (14.001) fluazinam, (14.002) meptyldinocap.

15) Further compounds, for example (15.001) abscisic acid, (15.002) benthiazole, (15.003) bethoxazin, (15.004) capsimycin, (15.005) carvone, (15.006) chinomethionat, (15.007) cufraneb, (15.008) cyflufenamid, (15.009) cymoxanil, (15.010) cyprosulfamide, (15.011) flutianil, (15.012) fosetyl-aluminium, (15.013) fosetyl-calcium, (15.014) fosetyl-sodium, (15.015) methyl isothiocyanate, (15.016) metrafenon, (15.017) mildiomycin, (15.018) natamycin, (15.019) nickel dimethyldithiocarbamate, (15.020) nitrothal-isopropyl, (15.021) oxamocarb, (15.022) oxathiapiprolin, (15.023) oxyfenthiin, (15.024) pentachlorophenol and salts, (15.025) phosphonic acid and salts thereof, (15.026) propamocarb-fosetylate, (15.027) pyriofenone (chlazafenone) (15.028) tebufloquin, (15.029) tecloftalam, (15.030) tolnifanide, (15.031) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.032) 1-(4-{4-[(5S)-5-(2,6- difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.033) 2-(6-benzylpyridin-2-yl)quinazoline, (15.034) 2,6-dimethyl-1H,5H-[1,4]dithiino[2,3-c:5,6-c']dipyrrole-1,3,5,7(2H,6H)-tetrone, (15.035) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.036) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.037) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.038) 2-[6-(3-fluoro-4-methoxyphenyl)-5-methylpyridin-2-yl]quinazoline, (15.039) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.040) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-,2-oxazol-5-yl}-3-chlorophenyl methanesulfonate, (15.041) 2-{2-[(7,8-difluoro-2-methylquinolin-3-yl)oxy]-6-fluorophenyl}propan-2-ol, (15.042) 2-{2-fluoro-6-[(8-fluoro-2-methylquinolin-3-yl)oxy]phenyl}propan-2-ol, (15.043) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl methanesulfonate, (15.044) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenyl methanesulfonate, (15.045) 2-phenylphenol and salts thereof, (15.046) 3-(4,4,5-trifluoro-3,3-dimethyl-3,4-dihydroisoquinolin-1-yl)quinoline, (15.047) 3-(4,4-difluoro-3,3-dimethyl-3,4-dihydroisoquinolin-1-yl)quinoline, (15.048) 4-amino-5-fluoropyrimidin-2-ol (tautomeric form: 4-amino-5-fluoropyrimidin-2(1H)-one), (15.049) 4-oxo-4-[(2-phenylethyl)amino]butyric acid, (15.050) 5-amino-1,3,4-thiadiazole-2-thiol, (15.051) 5-chloro-N'-phenyl-N'-(prop-2-yn-1-yl)thiophene 2-sulfonohydrazide, (15.052) 5-fluoro-2-[(4-fluorobenzyl)oxy]pyrimidin-4-amine, (15.053) 5-fluoro-2-[(4-methylbenzyl)oxy]pyrimidin-4-amine, (15.054) 9-fluoro-2,2-dimethyl-5-(quinolin-3-yl)-2,3-dihydro-1,4-benzoxazepine, (15.055) but-3-yn-1-yl {6-[({[(Z)-(1-methyl-1H-tetrazol-5-yl)(phenyl)methylene]amino}oxy)methyl]pyridin-2-yl}carbamate, (15.056) ethyl (2Z)-3-amino-2-cyano-3-phenylacrylate, (15.057) phenazine-1-carboxylic acid, (15.058) propyl 3,4,5-trihydroxybenzoate, (15.059) quinolin-8-ol, (15.060) quinolin-8-ol sulfate (2:1), (15.061) tert-butyl {6-[({[(1-methyl-1H-tetrazol-5-yl)(phenyl)methylene]amino}oxy)methyl]pyridin-2-yl}carbamate, (15.062) 5-fluoro-4-imino-3-methyl-1-[(4-methylphenyl)sulfonyl]-3,4-dihydropyrimidin-2(1H)-one.

Biological Pesticides as Mixing Components

The compounds of the formula (I) can be combined with biological pesticides.

Biological pesticides especially include bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are: *Bacillus amyloliquefaciens*, strain FZB42 (DSM 231179), or *Bacillus cereus*, especially *B. cereus* strain CNCM I-1562, or *Bacillus firmus*, strain I-1582 (Accession number CNCM I-1582), or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421), *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii* (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum rifai* T39 (Accession number CNCM I-952).

Examples of viruses which are used or can be used as biological pesticides are:

*Adoxophyes orana* (summer fruit tortrix) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans, Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum, Glomus* spp., *Laccaria* spp., *Lactobacillus buchneri, Paraglomus* spp., *Pisolithus tinctorus, Pseudomonas* spp., *Rhizobium* spp., especially *Rhizobium trifolii, Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are: Allium sativum, Artemisia absinthium, azadirachtin, Biokeeper WP, Cassia nigricans, Celastrus angulatus, Chenopodium anthelminticum, chitin, Armour-Zen, Dryopteris filixmas, Equisetum arvense, Fortune Aza, Fungastop, Heads Up (Chenopodium quinoa saponin extract), pyrethrum/pyrethrins, Quassia amara, Quercus, Quillaja, Regalia, "Requiem™ Insecticide", rotenone, ryania/ryanodine, Symphytum officinale, Tanacetum vulgare, thymol, Triact 70, TriCon, Tropaeulum majus, Urtica dioica, Veratrin, Viscum album, Brassicaceae extract, especially oilseed rape powder or mustard powder.

Safener as Mixing Components

The compounds of the formula (I) can be combined with safeners, for example benoxacor, cloquintocet (-mexyl), cyometrinil, cyprosulfamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulfonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya beans, potatoes, sugar beet, sugar cane, tomatoes, bell peppers, cucumbers, melons, carrots, water melons, onions, lettuce, spinach, leeks, beans, *Brassica oleracea* (e.g. cabbage) and other vegetable species, cotton, tobacco, oilseed rape, and also fruit plants (the fruits being apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all development stages such as seed, seedlings, young (immature) plants, up to and including mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested plants or harvested plant parts and vegetative and generative propagation material, for example cuttings, tubers, rhizomes, slips and seeds.

The inventive treatment of the plants and parts of plants with the compounds of the formula (I) is effected directly or by allowing the compounds to act on the surroundings, the habitat or the storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and their parts in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having novel properties ("traits") and which have been obtained by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better capability for storage and/or processability of the harvested products. Further and particularly emphasized examples of such properties are increased resistance of the plants to animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants to phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidal active compounds, for example imidazolinones, sulfonylureas, glyphosate or phosphinothricin (for example the "PAT" gene). The genes which impart the desired properties ("traits") in question may also be present in combinations with one another in the transgenic plants. Examples of transgenic plants mentioned include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (the fruits being apples, pears, citrus fruits and grapevines), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, meaning that the compounds of the formula (I) are applied to the foliage, in which case the treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) according to the invention are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active compound used so as to provide optimum protection for the seed and the germinating plant from attack by animal pests, but without damage to the plant itself by the active compound used. In particular, methods for the treatment of seed should also take account of the intrinsic insecticidal or nematicidal properties of pest-resistant or -tolerant transgenic plants in order to achieve optimal protection of the seed and also the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) according to the invention for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and mixing components may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages that occur when a compound of the formula (I) acts systemically is that the treatment of the seed protects not only the seed itself but also the plants resulting therefrom, after emergence, from animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Compounds of the formula (I) can also be used in combination with signalling technology compositions, leading to better colonization by symbionts, for example rhizobia, mycorrhizae and/or endophytic bacteria or fungi, and/or to optimized nitrogen fixation.

The compounds of the formula (I) are suitable for the protection of seed of any plant variety which is used in agriculture, in greenhouses, in forests or in horticulture. More particularly, this is the seed of cereals (for example wheat, barley, rye, millet and oats), maize, cotton, soya beans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape, vegetables and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate from microorganisms such as *Bacillus, Rhizobium, Pseudomonas, Serratia, Trichoderma, Clavibacter, Glomus* or *Gliocladium*. The present invention is particularly suitable for treatment of transgenic seed which comprises at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been soaked, for example in water, until it reaches a certain stage of the rice embryo ("pigeon breast stage") which results in stimulation of germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing the compounds of the formula (I) with customary additives, for example customary extenders and solvents or diluents, dyes, wetting agents, dispersants, emulsifiers, antifoams, preservatives, secondary thickeners, adhesives, gibberellins, and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting compositions which may be present in the seed-dressing formulations usable in accordance with the invention are all substances which promote wetting and which are customary for the formulation of agrochemically active compounds. Usable with preference are alkyl naphthalenesulfonates, such as diisopropyl or diisobutyl naphthalenesulfonates.

Suitable dispersants and/or emulsifiers which may be present in the seed-dressing formulations usable in accordance with the invention are all nonionic, anionic and cationic dispersants customary for the formulation of agrochemically active compounds. Nonionic or anionic dispersants or mixtures of nonionic or anionic dispersants can be used with preference. Suitable nonionic dispersants especially include ethylene oxide/propylene oxide block polymers, alkylphenol polyglycol ethers and tristyrylphenol polyglycol ethers, and the phosphated or sulfated derivatives thereof. Suitable anionic dispersants are especially lignosulfonates, polyacrylic acid salts and arylsulfonate-formaldehyde condensates.

Antifoams which may be present in the seed-dressing formulations usable in accordance with the invention are all foam-inhibiting substances customary for the formulation of agrochemically active compounds. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Useful secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Useful gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schadlingsbekampfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute application forms thereof, can also be used to dress seed of transgenic plants.

For the treatment of seed with the seed-dressing formulations usable in accordance with the invention, or the application forms prepared therefrom through the addition of water, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed-dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasite" includes especially helminths and protozoa, such as coccidia. Ectoparasites are typically and preferably arthropods, especially insects or acarids.

In the field of veterinary medicine, the compounds of the formula (I) having favourable endotherm toxicity are suitable for controlling parasites which occur in animal husbandry and animal keeping in livestock, breeding animals, zoo animals, laboratory animals, experimental animals and domestic animals. They are active against all or specific stages of development of the parasites.

Agricultural livestock include, for example, mammals, such as sheep, goats, horses, donkeys, camels, buffalo, rabbits, reindeer, fallow deer and especially cattle and pigs; or poultry such as turkeys, ducks, geese and especially chickens; or fish or crustaceans, for example in aquaculture; or, as the case may be, insects such as bees.

Domestic animals include, for example, mammals, such as hamsters, guinea pigs, rats, mice, chinchillas, ferrets, and particularly dogs, cats, caged birds; reptiles, amphibians or aquarium fish.

In a specific embodiment, the compounds of the formula (I) are administered to mammals.

In another specific embodiment, the compounds of the formula (I) are administered to birds, namely caged birds or particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal keeping is enabled and better animal well-being is achievable.

In relation to the field of animal health, the term "control" or "controlling" in the present context means that the compounds of the formula (I) are effective in reducing the incidence of the particular parasite in an animal infected with such parasites to an innocuous degree. More specifically, "controlling" in the present context means that the compounds of the formula (I) kill the respective parasite, inhibit its growth, or inhibit its proliferation.

The arthropods include, for example, but are not limited to, from the order of Anoplurida, for example, *Haematopinus* spp., *Linognathus* spp., *Pediculus* spp., *Phtirus* spp. and *Solenopotes* spp.;

from the order of Mallophagida and the suborders Amblycerina and Ischnocerina, for example *Bovicola* spp., *Damalina* spp., *Felicola* spp.; *Lepikentron* spp., *Menopon* spp., *Trichodectes* spp., *Trimenopon* spp., *Trinoton* spp., *Wemeckiella* spp;

from the order of Diptera and the suborders Nematocerina and Brachycerina, for example *Aedes* spp., *Anopheles* spp., *Atylotus* spp., *Braula* spp., *Calliphora* spp., *Chrysomyia* spp., *Chrysops* spp., *Culex* spp., *Culicoides* spp., *Eusimulium* spp., *Fannia* spp., *Gasterophilus* spp., *Glossina* spp., *Haematobia* spp., *Haematopota* spp., *Hippobosca* spp., *Hybomitra* spp., *Hydrotaea* spp., *Hypoderma* spp., *Lipoptena* spp., *Lucilia* spp., *Lutzomyia* spp., *Melophagus* spp., *Morellia* spp., *Musca* spp., *Odagmia* spp., *Oestrus* spp., *Philipomyia* spp., *Phlebotomus* spp., *Rhinoestrus* spp., *Sarcophaga* spp., *Simulium* spp., *Stomoxys* spp., *Tabanus* spp., *Tipula* spp., *Wilhelmia* spp., *Wohlfahrtia* spp.;

from the order of Siphonapterida, for example *Ceratophyllus* spp., *Ctenocephalides* spp., *Pulex* spp., *Tunga* spp., *Xenopsylla* spp.;

from the order of Heteropterida, for example *Cimex* spp., *Panstrongylus* spp., *Rhodnius* spp., *Triatoma* spp.; and also nuisance and hygiene pests from the order Blattarida.

In addition, in the case of the arthropods, mention should be made by way of example, without limitation, of the following Acari:

from the sub-class of Acari (Acarina) and the order of Metastigmata, for example of the family Argasidae, such as *Argas* spp., *Omithodorus* spp., *Otobius* spp., from the family of Ixodidae, such as *Amblyomma* spp., *Dermacentor* spp., *Haemaphysalis* spp., *Hyalomma* spp., *Ixodes* spp., *Rhipicephalus* (*Boophilus*) spp., *Rhipicephalus* spp. (the original genus of multi-host ticks); from the order of Mesostigmata, such as *Dermanyssus* spp., *Omithonyssus* spp., *Pneumonyssus* spp., *Raillietia* spp., *Sternostoma* spp., *Tropilaelaps* spp., *Varroa* spp.; from the order of the Actinedida (Prostigmata), for example *Acarapis* spp., *Cheyletiella* spp., *Demodex* spp., *Listrophorus* spp., *Myobia* spp., *Neotrombicula* spp., *Ornithocheyletia* spp., *Psorergates* spp., *Trombicula* spp.; and from the order of Acaridida (Astigmata), zum *Beispiel acarus* spp., *Caloglyphus* spp., *Chorioptes* spp., *Cytodites* spp., *Hypodectes* spp., *Knemidocoptes* spp., *Laminosioptes* spp., *Notoedres* spp., *Otodectes* spp., *Psoroptes* spp., *Pterolichus* spp., *Sarcoptes* spp., *Trixacarus* spp., *Tyrophagus* spp.

Examples of parasitic protozoa include, but are not limited to:

Mastigophora (*Flagellata*), such as:

Metamonada: from the order of Diplomonadida, for example, *Giardia* spp., *Spironucleus* spp.

Parabasala: from the order of Trichomonadida, for example, *Histomonas* spp., *Pentatrichomonas* spp., *Tetratrichomonas* spp., *Trichomonas* spp., *Tritrichomonas* spp.

Euglenozoa: from the order of Trypanosomatida, for example, *Leishmania* spp., *Trypanosoma* spp.

Sarcomastigophora (Rhizopoda) such as Entamoebidae, for example *Entamoeba* spp., Centramoebidae, for example *Acanthamoeba* sp., Euamoebidae, e.g. *Hartmanella* sp.

Alveolata such as Apicomplexa (Sporozoa): e.g. *Cryptosporidium* spp.; from the order of Eimeriida, for example, *Besnoitia* spp., *Cystoisospora* spp., *Eimeria* spp., *Hammondia* spp., *Isospora* spp., *Neospora* spp., *Sarcocystis* spp., *Toxoplasma* spp.; from the order of Adeleida, for example, *Hepatozoon* spp., *Klossiella* spp.; from the order of Haemosporida, for example, *Leucocytozoon* spp., *Plasmodium* spp.; from the order of Piroplasmida, for example, *Babesia* spp., *Ciliophora* spp., *Echinozoon* spp., *Theileria* spp.; from the order of Vesibuliferida, for example, *Balantidium* spp., *Buxtonella* spp.

Microspora such as *Encephalitozoon* spp., *Enterocytozoon* spp., *Globidium* spp., *Nosema* spp., and also, for example, *Myxozoa* spp.

The helminths that are pathogenic to humans or animals include, for example, Acanthocephala, nematodes, Pentastoma and Platyhelminthes (e.g. Monogenea, cestodes and trematodes).

Exemplary helminths include, but are not limited to:

Monogenea: e.g. *Dactylogyrus* spp., *Gyrodactylus* spp., *Microbothrium* spp., *Polystoma* spp., *Troglecephalus* spp.;

Cestodes: from the order of Pseudophyllidea, for example: *Bothridium* spp., *Diphyllobothrium* spp., *Diplogonoporus* spp., *Ichthyobothrium* spp., *Ligula* spp., *Schistocephalus* spp., *Spirometra* spp.

From the order of Cyclophyllida, for example: *Andyra* spp., *Anoplocephala* spp., *Avitellina* spp., *Bertiella* spp., *Cittotaenia* spp., *Davainea* spp., *Diorchis* spp., *Diplopylidium* spp., *Dipylidium* spp., *Echinococcus* spp., *Echinocotyle* spp., *Echinolepis* spp., *Hydatigera* spp., *Hymenolepis* spp., *Joyeuxiella* spp., *Mesocestoides* spp., *Moniezia* spp., *Paranoplocephala* spp., *Raillietina* spp., *Stilesia* spp., *Taenia* spp., *Thysaniezia* spp., *Thysanosoma* spp.

Trematodes: from the class of Digenea, for example: *Austrobilharzia* spp., *Brachylaima* spp., *Calicophoron* spp., *Catatropis* spp., *Clonorchis* spp. *Collyriclum* spp., *Cotylophoron* spp., *Cyclocoelum* spp., *Dicrocoelium* spp., *Diplostomum* spp., *Echinochasmus* spp., *Echinoparyphium* spp., *Echinostoma* spp., *Eurytrema* spp., *Fasciola* spp., *Fasciolides* spp., *Fasciolopsis* spp., *Fischoederius* spp., *Gastrothylacus* spp., *Gigantobilharzia* spp., *Gigantocotyle* spp., *Heterophyes* spp., *Hypoderaeum* spp., *Leucochloridium* spp., *Metagonimus* spp., *Metorchis* spp., *Nanophyetus* spp., *Notocotylus* spp., *Opisthorchis* spp., *Ornithobilharzia* spp., *Paragonimus* spp., *Paramphistomum* spp., *Plagiorchis* spp., *Posthodiplostomum* spp., *Prosthogonimus* spp., *Schistosoma* spp., *Trichobilharzia* spp., *Troglotrema* spp., *Typhlocoelum* spp.

Nematodes: from the order of Trichinellida, for example: *Capillaria* spp., *Trichinella* spp., *Trichomosoides* spp., *Trichuris* spp.

From the order of Tylenchida, for example: *Micronema* spp., *Parastrangyloides* spp., *Strongyloides* spp.

From the order of Rhabditina, for example: *Aelurostrongylus* spp., *Amidostomum* spp., *Ancylostoma* spp., *Angiostrongylus* spp., *Bronchonema* spp., *Bunostomum* spp., *Chabertia* spp., *Cooperia* spp., *Cooperioides* spp., *Creno-* soma spp., *Cyathostomum* spp., *Cyclococercus* spp., *Cyclodontostomum* spp., *Cylicocyclus* spp., *Cylicostephanus* spp., *Cylindropharynx* spp., *Cystocaulus* spp., *Dictyocaulus* spp., *Elaphostrongylus* spp., *Filaroides* spp., *Globocephalus* spp., *Graphidium* spp., *Gyalocephalus* spp., *Haemonchus* spp., *Heligmosomoides* spp., *Hyostrongylus* spp., *Marshallagia* spp., *Metastrongylus* spp., *Muellerius* spp., *Necator* spp., *Nematodirus* spp., *Neostrongylus* spp., *Nippostrongylus* spp., *Obeliscoides* spp., *Oesophagodontus* spp., *Oesophagostomum* spp., *Ollulanus* spp.; *Ornithostrongylus* spp., *Oslerus* spp., *Ostertagia* spp., *Paracooperia* spp., *Paracrenosoma* spp., *Parafilaroides* spp., *Parelaphostrongylus* spp., *Pneumocaulus* spp., *Pneumostrongylus* spp., *Poteriostomum* spp., *Protostrongylus* spp., *Spicocaulus* spp., *Stephanurus* spp., *Strongylus* spp., *Syngamus* spp., *Teladorsagia* spp., *Trichonema* spp., *Trichostrongylus* spp., *Triodontophorus* spp., *Troglostrongylus* spp., *Uncinaria* spp.

From the order of Spirurida, for example: *Acanthocheilonema* spp., *Anisakis* spp., *Ascaridia* spp.; *Ascaris* spp., *Ascarops* spp., *Aspiculuris* spp., *Baylisascaris* spp., *Brugia* spp., *Cercopithifilaria* spp., *Crassicauda* spp., *Dipetalonema* spp., *Dirofilaria* spp., *Dracunculus* spp.; *Draschia* spp., *Enterobius* spp., *Filaria* spp., *Gnathostoma* spp., *Gongylonema* spp., *Habronema* spp., *Heterakis* spp.; *Litomosoides* spp., *Loa* spp., *Onchocerca* spp., *Oxyuris* spp., *Parabronema* spp., *Parafilaria* spp., *Parascaris* spp., *Passalurus* spp., *Physaloptera* spp., *Probstmayria* spp., *Pseudofilaria* spp., *Setaria* spp., *Skjrabinema* spp., *Spirocerca* spp., *Stephanofilaria* spp., *Strongyluris* spp., *Syphacia* spp., *Thelazia* spp., *Toxascaris* spp., *Toxocara* spp., *Wuchereria* spp.

Acanthocephala: from the order of Oligacanthorhynchida, for example: *Macracanthorhynchus* spp., *Prosthenorchis* spp.; from the order of Moniliformida, for example: *Moniliformis* spp.

From the order of Polymorphida, for example: *Filicollis* spp.; from the order of Echinorhynchida, for example *Acanthocephalus* spp., *Echinorhynchus* spp., *Leptorhynchoides* spp.

Pentastoma: from the order of Porocephalida, for example, *Linguatula* spp.

In the veterinary field and in animal keeping, the compounds of the formula (I) are administered by methods generally known in the art, such as via the enteral, parenteral, dermal or nasal route in the form of suitable preparations. Administration may be prophylactic, metaphylactic or therapeutic.

Thus, one embodiment of the present invention relates to the compounds of the formula (I) for use as a medicament.

A further aspect relates to the compounds of the formula (I) for use as an antiendoparasitic agent.

A further specific aspect of the invention relates to the compounds of the formula (I) for use as an antihelminthic agent, especially for use as a nematicide, platyhelminthicide, acanthocephalicide or pentastomicide.

A further specific aspect of the invention relates to the compounds of the formula (I) for use as an antiprotozoic agent.

A further aspect relates to the compounds of the formula (I) for use as an antiectoparasitic agent, especially an arthropodicide, very particularly an insecticide or an acaricide.

Further aspects of the invention are veterinary medicine formulations comprising an effective amount of at least one compound of the formula (I) and at least one of the following: a pharmaceutically acceptable excipient (e.g. solid or liquid diluents), a pharmaceutically acceptable auxiliary (e.g. surfactants), especially a pharmaceutically acceptable excipient used conventionally in veterinary medicine formulations and/or a pharmaceutically acceptable auxiliary conventionally used in veterinary medicine formulations.

A related aspect of the invention is a method for production of a veterinary medicine formulation as described here, which comprises the step of mixing at least one compound of the formula (I) with pharmaceutically acceptable excipients and/or auxiliaries, especially with pharmaceutically acceptable excipients used conventionally in veterinary medicine formulations and/or auxiliaries used conventionally in veterinary medicine formulations.

Another specific aspect of the invention is veterinary medicine formulations selected from the group of ectoparasiticidal and endoparasiticidal formulations, especially selected from the group of anthelmintic, antiprotozoic and arthropodicidal formulations, very particularly selected from the group of nematicidal, platyhelminthicidal, acanthocephalicidal, pentastomicidal, insecticidal and acaricidal formulations, according to the aspects mentioned, and methods for production thereof.

Another aspect relates to a method for treatment of a parasitic infection, especially an infection caused by a parasite selected from the group of the ectoparasites and endoparasites mentioned here, by use of an effective amount of a compound of the formula (I) in an animal, especially a nonhuman animal, having a need therefor.

Another aspect relates to a method for treatment of a parasitic infection, especially an infection caused by a parasite selected from the group of the ectoparasites and endoparasites mentioned here, by use of a veterinary medicine formulation as defined here in an animal, especially a nonhuman animal, having a need therefor.

Another aspect relates to the use of the compounds of the formula (I) in the treatment of a parasite infection, especially an infection caused by a parasite selected from the group of the ectoparasites and endoparasites mentioned here, in an animal, especially a nonhuman animal.

In the present context of animal health or veterinary medicine, the term "treatment" includes prophylactic, metaphylactic and therapeutic treatment.

In a particular embodiment, in this way, mixtures of at least one compound of the formula (I) with other active compounds, especially with endo- and ectoparasiticides, are provided for the field of veterinary medicine.

In the field of animal health, "mixture" means not just that two (or more) different active compounds are formulated in a common formulation and are correspondingly employed together, but also relates to products comprising formulations separated for each active compound.

Accordingly, when more than two active compounds are to be employed, all active compounds can be formulated in a common formulation or all active compounds can be formulated in separate formulations; likewise conceivable are mixed forms in which some of the active compounds are formulated together and some of the active compounds are formulated separately. Separate formulations allow the separate or successive application of the active compounds in question.

The active compounds specified here by their common names are known and are described, for example, in the "Pesticide Manual" (see above) or can be searched for on the Internet (e.g.: http://www.alanwood.net/pesticides).

Illustrative active compounds from the group of the ectoparasiticides as mixing components include, without any intention that this should constitute a restriction, the insecticides and acaricides listed in detail above. Further usable active compounds are listed below in accordance with the abovementioned classification based on the current IRAC Mode of Action Classification Scheme: (1) acetylcholinesterase (AChE) inhibitors; (2) GABA-gated chloride channel blockers; (3) sodium channel modulators; (4) nicotinic acetylcholine receptor (nAChR) competitive modulators; (5) nicotinic acetylcholine receptor (nAChR) allosteric modulators; (6) glutamate-gated chloride channel (GluCl) allosteric modulators; (7) juvenile hormone mimetics; (8) miscellaneous non-specific (multi-site) inhibitors; (9) chordotonal organ modulators; (10) mite growth inhibitors; (12) inhibitors of mitochondrial ATP synthase, such as ATP disruptors; (13) uncouplers of oxidative phosphorylation via disruption of the proton gradient; (14) nicotinic acetylcholine receptor channel blockers; (15) inhibitors of chitin biosynthesis, type 0; (16) inhibitors of chitin biosynthesis, type 1; (17) moulting disruptors (especially in Diptera); (18) ecdysone receptor agonists; (19) octopamine receptor agonists; (21) mitochondrial complex I electron transport inhibitors; (25) mitochondrial complex II electron transport inhibitors; (20) mitochondrial complex III electron transport inhibitors; (22) voltage-dependent sodium channel blockers; (23) inhibitors of acetyl CoA carboxylase; (28) ryanodine receptor modulators; active compounds having unknown or non-specific mechanisms of action, e.g. fentrifanil, fenoxacrim, cycloprene, chlorobenzilate, chlordimeform, flubenzimin, dicyclanil, amidoflumet, quinomethionat, triarathene, clothiazoben, tetrasul, potassium oleate, petroleum, metoxadiazone, gossyplur, flutenzine, brompropylate, cryolite;

compounds from other classes, for example butacarb, dimetilan, cloethocarb, phosphocarb, pirimiphos(-ethyl), parathion(-ethyl), methacrifos, isopropyl o-salicylate, trichlorfon, sulprofos, propaphos, sebufos, pyridathion, prothoate, dichlofenthion, demeton-S-methyl sulfone, isazofos, cyanofenphos, dialifos, carbophenothion, autathiofos, aromfenvinfos(-methyl), azinphos(-ethyl), chlorpyrifos(-ethyl), fosmethilan, iodofenphos, dioxabenzofos, formothion, fonofos, flupyrazofos, fensulfothion, etrimfos;

organochlorine compounds, for example camphechlor, lindane, heptachlor; or phenylpyrazoles, e.g. acetoprole, pyrafluprole, pyriprole, vaniliprole, sisapronil; or isoxazolines, e.g. sarolaner, afoxolaner, lotilaner, fluralaner;

pyrethroids, e.g. (cis-, trans-)metofluthrin, profluthrin, flufenprox, flubrocythrinate, fubfenprox, fenfluthrin, protrifenbut, pyresmethrin, RU15525, terallethrin, cis-resmethrin, heptafluthrin, bioethanomethrin, biopermethrin, fenpyrithrin, cis-cypermethrin, cis-permethrin, clocythrin, cyhalothrin (lambda-), chlovaporthrin, or halogenated hydrocarbon compounds (HCHs), neonicotinoids, e.g. nithiazine dicloromezotiaz, triflumezopyrim macrocyclic lactones, e.g. nemadectin, ivermectin, latidectin, moxidectin, selamectin, eprinomectin, doramectin, emamectin benzoate; milbemycin oxime triprene, epofenonane, diofenolan;

biologicals, hormones or pheromones, for example natural products, e.g. thuringiensin, codlemone or neem components dinitrophenols, e.g. dinocap, dinobuton, binapacryl;

benzoylureas, e.g. fluazuron, penfluron, amidine derivatives, e.g. chlormebuform, cymiazole, demiditraz beehive varroa acaricides, for example organic acids, e.g. formic acid, oxalic acid.

Illustrative active compounds from the group of the endoparasiticides, as mixing components, include, but are not limited to, anthelmintically active compounds and antiprotozoic active compounds.

The anthelmintically active compounds include but are not limited to the following nematicidally, trematicidally and/or cestocidally active compounds:

from the class of the macrocyclic lactones, for example: eprinomectin, abamectin, nemadectin, moxidectin, doramectin, selamectin, lepimectin, latidectin, milbemectin, ivermectin, emamectin, milbemycin;

from the class of the benzimidazoles and probenzimidazoles, for example: oxibendazole, mebendazole, triclabendazole, thiophanate, parbendazole, oxfendazole, netobimin, fenbendazole, febantel, thiabendazole, cyclobendazole, cambendazole, albendazole sulfoxide, albendazole, flubendazole;

from the class of the depsipeptides, preferably cyclic depsipeptides, especially 24-membered cyclic depsipeptides, for example: emodepside, PF1022A;

from the class of the tetrahydropyrimidines, for example: morantel, pyrantel, oxantel;

from the class of the imidazothiazoles, for example: butamisole, levamisole, tetramisole;

from the class of the aminophenylamidines, for example: amidantel, deacylated amidantel (dAMD), tribendimidine;

from the class of the aminoacetonitriles, for example: monepantel;

from the class of the paraherquamides, for example: paraherquamide, derquantel;

from the class of the salicylanilides, for example: tribromsalan, bromoxanide, brotianide, clioxanide, closantel, niclosamide, oxyclozanide, rafoxanide;

from the class of the substituted phenols, for example: nitroxynil, bithionol, disophenol, hexachlorophene, niclofolan, meniclopholan;

from the class of the organophosphates, for example: trichlorfon, naphthalofos, dichlorvos/DDVP, crufomate, coumaphos, haloxon;

from the class of the piperazinones/quinolines, for example: praziquantel, epsiprantel;

from the class of the piperazines, for example: piperazine, hydroxyzine;

from the class of the tetracyclines, for example: tetracycline, chlorotetracycline, doxycycline, oxytetracycline, rolitetracycline;

from various other classes, for example: bunamidine, niridazole, resorantel, omphalotin, oltipraz, nitroscanate, nitroxynil, oxamniquin, mirasan, miracil, lucanthon, hycanthon, hetolin, emetin, diethylcarbamazine, dichlorophen, diamfenetide, clonazepam, bephenium, amoscanate, clorsulon.

Antiprotozoic active compounds include, but are not limited to, the following active compounds:

from the class of the triazines, for example: diclazuril, ponazuril, letrazuril, toltrazuril;

from the class of polyether ionophores, for example: monensin, salinomycin, maduramicin, narasin;

from the class of the macrocyclic lactones, for example: milbemycin, erythromycin;

from the class of the quinolones, for example: enrofloxacin, pradofloxacin;

from the class of the quinines, for example: chloroquine;

from the class of the pyrimidines, for example: pyrimethamine;

from the class of the sulfonamides, for example: sulfaquinoxaline, trimethoprim, sulfaclozin;

from the class of the thiamines, for example: amprolium;

from the class of the lincosamides, for example: clindamycin;

from the class of the carbanilides, for example: imidocarb;

from the class of the nitrofurans, for example: nifurtimox;
from the class of the quinazolinone alkaloids, for example: halofuginone;
from various other classes, for example: oxamniquin, paromomycin;
from the class of the vaccines or antigens from microorganisms, for example: *Babesia canis rossi, Eimeria tenella, Eimeria praecox, Eimeria necatrix, Eimeria mitis, Eimeria maxima, Eimeria brunetti, Eimeria acervulina, Babesia canis vogeli, Leishmania infantum, Babesia canis canis, Dictyocaulus viviparus.*

All the mixing components mentioned, as the case may be, may also form salts with suitable bases or acids if they are capable of doing so on the basis of their functional groups.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) onto a host or after injection into a host (for example malaria parasites by mosquitoes).

Examples of vectors and the diseases or pathogens they transmit are:

1) Mosquitoes
*Anopheles*: malaria, filariasis;
*Culex*: Japanese encephalitis, filariasis, other viral diseases, transmission of other worms;
*Aedes*: yellow fever, dengue fever, other viral diseases, filariasis;
Simuliidae: transmission of worms, especially *Onchocerca volvulus;*
Psychodidae: transmission of leishmaniasis
2) Lice: skin infections, epidemic typhus;
3) Fleas: plague, endemic typhus, tapeworms;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borelliosis such as *Borrelia bungdorferi* sensu lato., *Borrelia duttoni*, tick-borne encephalitis, Q fever (*Coxiella burnetii*), babesia (*Babesia canis canis*), ehrlichiosis.

Examples of vectors in the context of the present invention are insects, for example aphids, flies, leafhoppers or *thrips*, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, Psychodidae such as *Phlebotomus, Lutzomyia*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders of Coleoptera, Hymenoptera, Isoptera, Lepidoptera, Psocoptera and Zygentoma.

Industrial materials in the present context are understood to mean inanimate materials, such as preferably plastics, adhesives, glues, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) take the form of a ready-to-use pesticide, meaning that they can be applied to the material in question without further modifications. Useful further insecticides or fungicides especially include those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active compounds, as antifouling compositions.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids, ticks and mites encountered in enclosed spaces, for example dwellings, factory halls, offices, vehicle cabins, animal breeding facilities. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

The preparation and use examples which follow illustrate the invention without limiting it.

PREPARATION EXAMPLES

Synthesis Example No. 1

1-(2-Cyanoethyl)-3-[(2,6-dichlorophenyl)carbamoyl]imidazo[1,2-a]pyridin-4-ium-2-olate (compound No. I-016)

1. Synthesis of 1-(2-cyanoethyl)-3-methoxycarbonylimidazo[1,2-a]pyridin-4-ium-2-olate

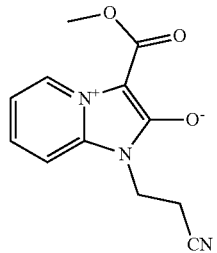 [SMILES: COC(=O)c1c([O-])n(CCC#N)c2cccc[n+]12]

Methyl 2,3-dichloro-3-oxopropanoate (known from Tetrahedron 1993, 49, 9447-9452) (2.85 g, 16.6 mmol), dissolved in 5 ml of dioxane, was added slowly dropwise to a solution of 3-(2-pyridylamino)propanenitrile (known from WO2016171053) (650 mg, 4.41 mmol) and triethylamine (536 mg, 5.30 mmol) in dioxane (15 ml), and the mixture was then stirred at room temperature for 3 hours. The reaction mixture was diluted with dichloromethane and washed with water and the organic phase was separated off and dried over magnesium sulfate. Following removal of the solvent by distillation under reduced pressure, the residue was adsorbed on silica gel and chromatographed using the mobile phase dichloromethane/2-propanol (92:8). This gave 264 mg (24% of theory) of 1-(2-cyanoethyl)-3-methoxycarbonylimidazo[1,2-a]pyridin-4-ium-2-olate. HPLC-MS: log P=0.39; mass (m/z): 246.1; $^1$H NMR (D$_6$-DMSO): δ 2.96 (m, 2H), 3.73 (s, 3H), 4.27 (m, 2H), 7.34 (m, 1H), 7.76 (m, 2H), 9.46 (d, 1H).

2. Synthesis of 1-(2-cyanoethyl)-3-[(2,6-dichlorophenyl)carbamoyl]imidazo[1,2-a]pyridin-4-ium-2-olate

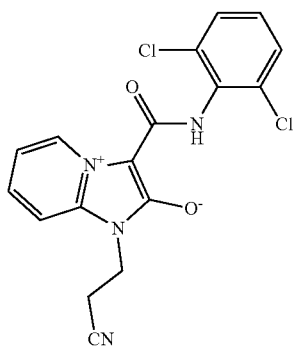 [SMILES: N#CCCn1c([O-])c(C(=O)Nc2c(Cl)cccc2Cl)[n+]2ccccc12]

2,6-Dichlorophenylamine (297 mg, 1.83 mmol) was initially charged in toluene, a 2M solution of trimethylaluminium in toluene (132 mg, 1.83 mmol) was added dropwise at 0° C. and the mixture was then stirred for 20 minutes. Subsequently, a solution of 1-(2-cyanoethyl)-3-methoxycarbonylimidazo[1,2-a]pyridin-4-ium-2-olate (150 mg, 0.36 mmol) in dichloromethane (5 ml) was added and the mixture was stirred at 75° C. for 16 hours. For work-up, the reaction mixture was initially stirred with 15 ml of 15% strength potassium sodium tartrate solution and then extracted repeatedly with dichloromethane. The organic phase was washed with water and dried over magnesium sulfate. After removal of the solvent by distillation under reduced pressure, the residue was adsorbed on silica gel and chromatographed using the mobile phase dichloromethane/2-propanol (92:8). This gave 39 mg (26% of theory) of 1-(2-cyanoethyl)-3-[(2,6-dichlorophenyl)carbamoyl]imidazo[1,2-a]pyridin-4-ium-2-olate. HPLC-MS: log P=1.81; mass (m/z): 375.0; $^1$H NMR (D$_6$-DMSO): δ 3.06 (m, 2H), 4.40 (m, 2H), 7.37 (m, 2H), 7.56 (m, 2H), 7.78 (m, 1H), 7.90 (m, 1H), 9.55 (d, 1H), 9.73 (s, 1H).

Synthesis Example No. 2

3-(2,2,2-trifluoroacetyl)-1-(2,2,2-trifluoroethyl)imidazo[1,2-a]pyridin-4-ium-2-olate (compound No. I-047)

1. Synthesis of 3-methoxycarbonyl-1-(2,2,2-trifluoroethyl)imidazo[1,2-a]pyridin-4-ium-2-olate

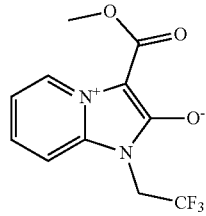 [SMILES: COC(=O)c1c([O-])n(CC(F)(F)F)c2cccc[n+]12]

Methyl 2,3-dichloro-3-oxopropanoate (known from Tetrahedron 1993, 49, 9447-9452) (233 mg, 1.36 mmol), dissolved in 2 ml of dioxane, was added slowly dropwise to a solution of N-(2,2,2-trifluoroethyl)pyridine-2-amine (200 mg, 1.13 mmol) and triethylamine (138 mg, 1.36 mmol) in dioxane (5 ml), and the mixture was then stirred at 50° C. for 3 hours. The reaction mixture was diluted with dichloromethane and washed with water and the organic phase was separated off and dried over magnesium sulfate. After removal of the solvent by distillation under reduced pressure, the residue was adsorbed on silica gel and chromatographed using the mobile phase cyclohexane/ethyl acetate. This gave 13 mg (4% of theory) of 3-methoxycarbonyl-1-(2,2,2-trifluoroethyl)imidazo[1,2-a]pyridin-4-ium-2-olate. HPLC-MS: log P=1.01; mass (m/z): 275.0; $^1$H-NMR (D$_6$-DMSO): δ 3.74 (s, 3H) 4.93 (q, 2H) 7.32-7.47 (m, 1H) 7.69-7.77 (m, 1H) 7.78-7.86 (m, 1H) 9.52 (d, 1H).

2. Synthesis of lithium 2-oxido-1-(2,2,2-trifluoroethyl)imidazo[1,2-a]pyridin-4-ium-3-carboxylate

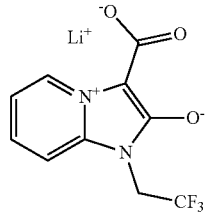

3-Methoxycarbonyl-1-(2,2,2-trifluoroethyl)imidazo[1,2-a]pyridin-4-ium-2-olate (680 mg, 2.48 mmol) was initially charged in a mixture of THF (50 ml) and water (10 ml), lithium hydroxide (119 mg, 4.96 mmol) was added and the mixture was then stirred at 40° C. for 16 hours. The precipitated solid was filtered off from the reaction solution and dried. This gave 400 mg (60% of theory) of lithium 2-oxido-1-(2,2,2-trifluoroethyl)imidazo[1,2-a]pyridin-4-ium-3-carboxylate; $^1$H NMR (D$_6$-DMSO): δ 5.01 (q, 2H) 7.21-7.35 (m, 1H) 7.58 (ddd, 1H) 7.68 (d, 1H) 10.05 (d, 1H).

3. Synthesis of 2-oxo-1-(2,2,2-trifluoroethyl)-2,3-dihydro-1H-imidazo[1,2-a]pyridin-4-ium chloride

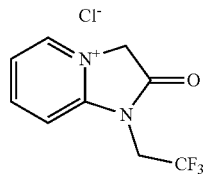 [SMILES: [Cl-] ; O=C1C[n+]2ccccc2N1CC(F)(F)F]

Lithium 2-oxido-1-(2,2,2-trifluoroethyl)imidazo[1,2-a]pyridin-4-ium-3-carboxylate (400 mg, 1.53 mmol) was suspended in dioxane (1 ml). After careful addition of 4N hydrochloric acid (0.77 ml, 3.07 mmol), the mixed was stirred at room temperature for another 4 hours. The resulting precipitate was filtered off with suction and dried. This gave 370 mg (87% of theory) of 2-oxo-1-(2,2,2-trifluoroethyl)-2,3-dihydro-1H-imidazo[1,2-a]pyridin-4-ium chloride; $^1$H NMR (D$_6$-DMSO): δ 4.98 (q, 2H) 5.51 (s, 2H) 7.75 (t, 1H) 8.05 (d, 1H) 8.62 (t, 1H) 8.93 (d, 1H).

4. Synthesis of 3-(2,2,2-trifluoroacetyl)-1-(2,2,2-trifluoroethyl)imidazo[1,2-a]pyridin-4-ium-2-olate

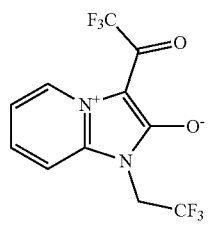 [SMILES: O=C(c1c([O-])n(CC(F)(F)F)c2cccc[n+]12)C(F)(F)F]

2-Oxo-1-(2,2,2-trifluoroethyl)-2,3-dihydro-1H-imidazo[1,2-a]pyridin-4-ium chloride (100 mg, 0.39 mmol) was initially charged in dioxane (2.0 ml), and triethylamine (48 mg, 0.47 mmol) was added. Trifluoroacetic anhydride (100 mg, 0.47 mmol) was then added dropwise as a solution in dioxane (2 ml) and the mixture was stirred at room temperature for 16 hours. The solvent was distilled off and the residue was taken up in dichloromethane. The solution was washed with water and the organic phase was separated off and dried over magnesium sulfate. After removal of the solvent by distillation under reduced pressure, the residue was adsorbed on silica gel and chromatographed using the mobile phase cyclohexane/ethyl acetate. This gave 31.0 mg (25% of theory) of 3-(2,2,2-trifluoroacetyl)-1-(2,2,2-trifluoroethyl)imidazo[1,2-a]pyridin-4-ium-2-olate. HPLC-MS: log P=1.79; mass (m/z): 313.1; $^1$H NMR (D$_6$-DMSO): δ 4.96 (q, 2H) 7.53 (dd, 1H) 7.87 (d, 1H) 8.02-8.18 (m, 1H) 9.82 (d, 1H).

Synthesis Example No. 3

3-(2-Methoxy-2-oxoacetyl)-1-(2,2,2-trifluoroethyl)imidazo[1,2-a]pyridin-4-ium-2-olate (compound No. I-051)

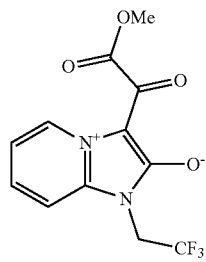 [SMILES: COC(=O)C(=O)c1c([O-])n(CC(F)(F)F)c2cccc[n+]12]

2-Oxo-1-(2,2,2-trifluoroethyl)-2,3-dihydro-1H-imidazo[1,2-a]pyridin-4-ium chloride (100 mg, 0.39 mmol) was initially charged in dioxane (2.0 ml), and triethylamine (201 mg, 1.98 mmol) was added. Methyl 2-chloro-2-oxoacetate (58 mg, 0.47 mmol) was then added dropwise as a solution in dioxane (2 ml) and the mixture was stirred at room temperature for 16 hours. The reaction mixture was distilled off and the residue was taken up in dichloromethane. The solution was washed with water and the organic phase was separated off and dried over magnesium sulfate. After removal of the solvent by distillation under reduced pressure, the residue was adsorbed on silica gel and chromatographed using the mobile phase cyclohexane/ethyl acetate. This gave 35.0 mg (29% of theory) of 3-(2-methoxy-2-oxoacetyl)-1-(2,2,2-trifluoroethyl)imidazo[1,2-a]pyridin-4-ium-2-olate. HPLC-MS: log P=1.18; mass (m/z): 303.0; $^1$H NMR (D$_6$-DMSO): δ 3.79 (s, 3H) 4.92 (q, 2H) 7.41-7.56 (m, 1H) 7.86 (d, 1H) 8.04 (td, 1H) 9.62 (d, 1H).

Synthesis Example No. 4

3-(2-Chloroacetyl)-1-(2-cyanoethyl)imidazo[1,2-a]pyridin-4-ium-2-olate (compound No. I-084)

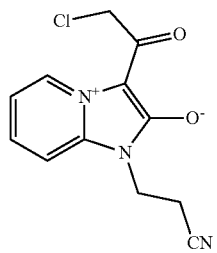 [SMILES: N#CCCn1c([O-])c(C(=O)CCl)[n+]2ccccc12]

Chloroacetyl chloride (5824 mg, 51.5 mmol) was added dropwise over 5 minutes to a solution of 3-(2-pyridylamino)propanenitrile (known from WO2016171053) (3300 mg, 22.4 mmol) in toluene (18 mL) and dimethylacetamide (4.8 ml), and the mixture was stirred first at 50° C. for 1 hour and then at room temperature for 18 hours. The reaction mixture was evaporated to dryness and the residue was adsorbed on silica gel and chromatographed using the mobile phase dichloromethane/2-propanol (92:8). This gave 2480 mg (41% of theory) of 3-(2-chloroacetyl)-1-(2-cyanoethyl)imidazo[1,2-a]pyridin-4-ium-2-olate. HPLC-MS: log P=0.80; mass (m/z): 264.1; $^1$H NMR (D$_6$-DMSO): δ 2.99 (m, 2H), 4.30 (m, 2H), 4.79 (s, 2H), 7.41 (m, 1H), 7.88 (m, 1H), 7.93 (d, 1H), 9.85 (m, 1H).

Synthesis Example No. 5

1-(2-Cyanoethyl)-3-[2-(1-methylcyclopropoxy)-2-oxo-acetyl]imidazo[1,2-a]pyridin-4-ium-2-olate (compound No. I-089)

1. Synthesis of 3-(2-oxo-3H-imidazo[1,2-a]pyridin-4-ium-1-yl)propanenitrile tetrafluoroborate

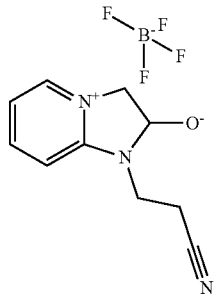

3-(2-Chloroacetyl)-1-(2-Cyanoethyl)imidazo[1,2-a]pyridin-4-ium-2-olate from Synthesis example 4 (150 mg, 0.56 mmol) was suspended in chloroform (5 mL), and 50% strength tetrafluoroboric acid (124.8 mg, 0.71 mmol) was added. The mixture was then stirred at room temperature for 16 hours. At 50° C., 4 mbar the reaction mixture was evaporated to dryness, giving 3-(2-oxo-3H-imidazo[1,2-a]pyridin-4-ium-1-yl)propanenitrile tetrafluoroborate as a viscous oil which was used in the next reaction step without further purification.

2. Synthesis of 1-(2-cyanoethyl)-3-[2-(1-methylcyclopropoxy)-2-oxoacetyl]imidazo[1,2-a]pyridin-4-ium-2-olate

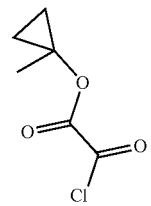

1-Methylcyclopropan-1-ol (500 mg, 6.93 mmol) was initially charged in dichloromethane (10.4 mL), oxalic chloride (924.1 mg, 7.28 mmol) was added and the mixture was stirred at room temperature for 3 hours. One equivalent of the reaction solution was directly employed in reaction step 3.

3. Synthesis of 1-(2-cyanoethyl)-3-[2-(1-methylcyclopropoxy)-2-oxoacetyl]imidazo[1,2-a]pyridin-4-ium-2-olate

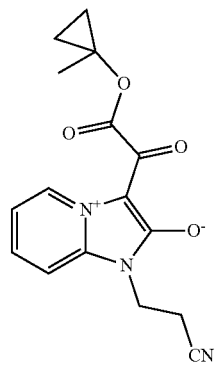 [SMILES: CC1(OC(=O)C(=O)c2c([O-])n(CCC#N)c3cccc[n+]23)CC1]

Dichloromethane (2 ml) was added to 3-(2-oxo-3H-imidazo[1,2-a]pyridin-4-ium-1-yl)propanenitrile tetrafluoroborate from reaction step 1, and subsequently, at 5° C., the reaction solution of 1-methylcyclopropyl 2-chloro-2-oxo-acetate (138.7 mg, 0.85 mmol) from reaction step 2 and then triethylamine (287.8 mg, 2.84 mmol) were added. The reaction mixture was stirred for 3 hours and then taken up in water/dichloromethane and the organic phase was separated off and evaporated to dryness. The residue was adsorbed on silica gel and chromatographed using the mobile phase dichloromethane/2-propanol (92:8). This gave 60 mg (28% of theory) of 1-(2-cyanoethyl)-3-[2-(1-methylcyclopropoxy)-2-oxo-acetyl]imidazo[1,2-a]pyridin-4-ium-2-olate. HPLC-MS: log P=1.33; mass (m/z): 313.1; $^1$H NMR (D$_6$-DMSO): δ 0.88 (m, 2H), 1.03 (m, 2H), 1.59 (s, 3H), 2.95 (m, 2H), 4.26 (m, 2H), 7.42 (m, 1H), 7.89 (m, 1H), 7.97 (d, 1H), 9.55 (m, 1H).

Synthesis Example No. 6

3-(2-Chloroacetyl)-1-(2-cyanoethyl)-8-methyl-imidazo[1,2-a]pyridin-4-ium-2-olate (compound No. I-095)

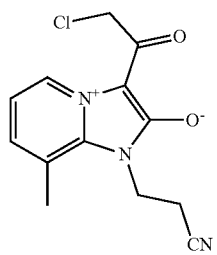 [SMILES: Cc1ccc[n+]2c(C(=O)CCl)c([O-])n(CCC#N)c12]

Analogously to Synthesis example No. 4,3-[(3-methyl-2-pyridyl)amino]propanenitrile (obtained by the process for 3-(2-pyridylamino)propanenitrile from Synthesis example No. 4) (950 mg, 5.89 mmol) was reacted with chloroacetyl chloride (1530 mg, 13.5 mmol), giving 350 mg (36% of theory) of 3-(2-chloroacetyl)-1-(2-cyanoethyl)-8-methyl-imidazo[1,2-a]pyridin-4-ium-2-olate. HPLC-MS: log P=0.80; mass (m/z): 277.1; 1H NMR (D$_6$-DMSO): δ 2.05 (s, 3H), 2.78 (m, 2H), 3.58 (m, 2H), 6.30 (s, 2H), 6.50 (m, 1H), 7.26 (m, 1H), 7.89 (m, 1H).

Synthesis Example No. 7

1-(2-Cyanoethyl)-8-methyl-3-(2,2,2-trifluoroacetyl)imidazo[1,2-a]pyridin-4-ium-2-olate (compound No. I-027)

1. Synthesis of 3-(8-methyl-2-oxo-3H-imidazo[1,2-a]pyridin-4-ium-1-yl)propanenitrile tetrafluoroborate

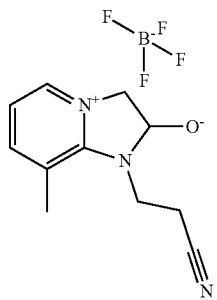

3-(2-Chloroacetyl)-1-(2-cyanoethyl)imidazo[1,2-a]pyridin-4-ium-2-olate from Synthesis example 6 (150 mg, 0.54 mmol) was suspended in chloroform (5 mL), and 50% strength tetrafluoroboric acid (118.5 mg, 0.67 mmol) was added. The mixture was then stirred at room temperature for 16 hours. At 50° C., 4 mbar the reaction mixture was evaporated to dryness, giving 3-(8-methyl-2-oxo-3H-imidazo[1,2-a]pyridin-4-ium-1-yl)propanenitrile tetrafluoroborate as a viscous oil which was used without further purification in the next reaction step.

2. Synthesis of 1-(2-cyanoethyl)-8-methyl-3-(2,2,2-trifluoroacetyl)imidazo[1,2-a]pyridin-4-ium-2-olate

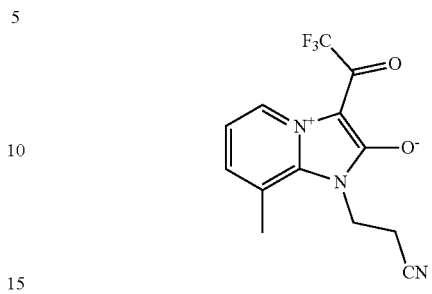

Dichloromethane (5 ml) was added to 3-(8-methyl-2-oxo-3H-imidazo[1,2-a]pyridin-4-ium-1-yl)propanenitrile tetrafluoroborate (156 mg, 0.54 mmol) from reaction step 1, and subsequently, at 5° C., trifluoroacetic anhydride (170.1 mg, 0.81 mmol) and then triethylamine (273.2 mg, 2.70 mmol) were added. The reaction mixture was stirred for 3 hours and then taken up in water/dichloromethane and the organic phase was separated off and evaporated to dryness. The residue was adsorbed on silica gel and chromatographed using the mobile phase dichloromethane/2-propanol (92:8). This gave 66 mg (40.7% of theory) of 1-(2-cyanoethyl)-8-methyl-3-(2,2,2-trifluoroacetyl)imidazo[1,2-a]pyridin-4-ium-2-olate. HPLC-MS: log P=1.35; mass (m/z): 297.1; $^1$H NMR (D$_6$-DMSO): δ 2.70 (s, 3H), 3.02 (m, 2H), 4.42 (m, 2H), 7.38 (m, 1H), 7.83 (m, 1H), 9.78 (m, 1H).

Synthesis Example No. 8

1-(2-Cyanoethyl)-3-[3-(trifluoromethyl)benzoyl]imidazo[1,2-a]pyridin-4-ium-2-olate (compound No. I-004)

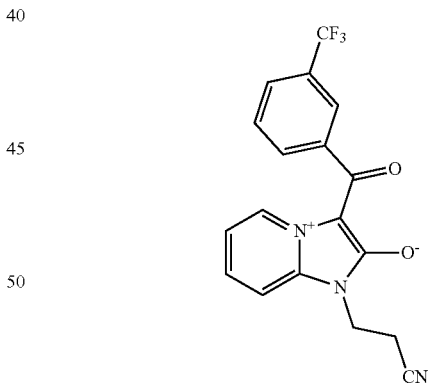

Dichloromethane (5 ml) was added to 3-(2-oxo-3H-imidazo[1,2-a]pyridin-4-ium-1-yl)propanenitrile tetrafluoroborate (150 mg, 0.54 mmol) from Synthesis example 5, reaction step 1, and 3-(trifluoromethyl)benzoyl chloride (170.6 mg, 0.81 mmol) and then triethylamine (275.9 mg, 2.72 mmol) were added. The reaction mixture was stirred for 16 hours and then taken up in water/dichloromethane and the organic phase was separated off and evaporated to dryness. The residue was adsorbed on silica gel and chromatographed using the mobile phase dichloromethane/2-propanol (92:8). This gave 100 mg (50% of theory) of 1-(2-cyanoethyl)-3-[3-(trifluoromethyl)benzoyl]imidazo[1,2-a]pyridin-4-ium- 2-olate. HPLC-MS: log P=1.35; mass (m/z): 359.1; ¹H NMR (D₆-DMSO): δ 2.95 (m, 2H), 4.27 (m, 2H), 7.43 (m, 1H), 7.67 (m, 1H), 7.6-8.2 (m, 5H), 10.03 (m, 1H).

Synthesis Example No. 9

1-(2-Cyanoethyl)-3-[(2E)-2-methoxyiminoacetyl]imidazo[1,2-a]pyridin-4-ium-2-olate (compound No. I-094)

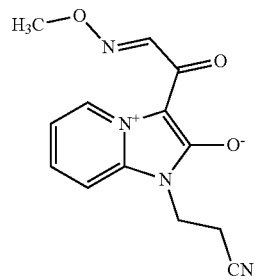 [SMILES: CO/N=C/C(=O)c1c([O-])n(CCC#N)c2cccc[n+]12]

Dichloromethane (5 ml) was added to 3-(2-oxo-3H-imidazo[1,2-a]pyridin-4-ium-1-yl)propanenitrile tetrafluoroborate (150 mg, 0.54 mmol) from Synthesis example 5, reaction step 1, and (2E)-2-methoxyiminoacetyl chloride (known from DE3208330) (103.7 mg, 0.85 mmol) and then triethylamine (275.9 mg, 2.84 mmol) were added. The reaction mixture was stirred for 16 hours and then taken up in water/dichloromethane and the organic phase was separated off and evaporated to dryness. The residue was adsorbed on silica gel and chromatographed using the mobile phase dichloromethane/2-propanol (92:8). This gave 40 mg (22% of theory) of 1-(2-cyanoethyl)-3-[(2E)-2-methoxyiminoacetyl]imidazo[1,2-a]pyridin-4-ium-2-olate. HPLC-MS: log P=0.73; mass (m/z): 273.1; ¹H NMR (D₆-DMSO): δ 2.97 (m, 2H), 3.96 (s, 3H), 4.29 (m, 2H), 7.43 (m, 1H), 7.8-8.0 (m, 2H), 8.9 (s, 1H), 9.95 (m, 1H).

The compounds according to the invention described in Table 1 below are likewise preferred compounds of the formula (I) according to the invention which are obtained according to or analogously to the Synthesis examples described above. They are based on the substructure of the formula (I-1).

TABLE 1

| No. | R¹ | G | T |
|---|---|---|---|
| I-001 | H | –CH₂CH₂C≡N | –CH₃ |
| I-002 | H | –CH₂CH₂C≡N | cyclopropyl |
| I-003 | H | –CH₂CH₂C≡N | phenyl |
| I-004 | H | –CH₂CH₂C≡N | 3-(trifluoromethyl)phenyl |
| I-005 | H | –CH₂CH₂C≡N | 1-methyl-1H-pyrazol-4-yl |
| I-006 | H | –CH₂CH₂C≡N | oxazol-2-yl |
| I-007 | H | –CH₂CH₂C≡N | –CF₃ |
| I-008 | H | –CH₂CH₂C≡N | –CH₂–O–CH₃ |
| I-009 | H | –CH₂CH₂C≡N | –CH₂–N(4-chloropyrazol-1-yl) |
| I-010 | H | –CH₂CH₂C≡N | –C(=O)CH₃ |
| I-011 | H | –CH₂CH₂C≡N | –C(=O)OCH₃ |
| I-012 | H | –CH₂CH₂C≡N | –C(=O)OCH₂CH₃ |

TABLE 1-continued (I-1)

| No. | R¹ | G | T |
|---|---|---|---|
| I-013 | H | –CH₂CH₂C≡N | –CH₂OCH₂CF₃ (ester, 2,2,2-trifluoroethyl ester) |
| I-014 | H | –CH₂CH₂C≡N | cyclobutyl ester |
| I-015 | H | –CH₂CH₂C≡N | –NH-cyclopropyl |
| I-016 | H | –CH₂CH₂C≡N | –NH-(2,6-dichlorophenyl) |
| I-017 | H | –CH₂CH₂C≡N | –NH-(3-fluoropyridin-2-yl) |
| I-018 | H | –CH₂CH₂C≡N | –NH-(3-trifluoromethylpyridin-2-yl) |
| I-019 | H | –CH₂CH₂C≡N | –NH-(2,4-dichloropyridin-3-yl) |
| I-020 | H | –CH₂CH₂C≡N | –NH-(1-methyl-1H-pyrazol-5-yl) |
| I-021 | CH₃ | –CH₂CH₂C≡N | –CH₃ |
| I-022 | CH₃ | –CH₂CH₂C≡N | cyclopropyl |
| I-023 | CH₃ | –CH₂CH₂C≡N | phenyl |
| I-024 | CH₃ | –CH₂CH₂C≡N | 3-trifluoromethylphenyl |
| I-025 | CH₃ | –CH₂CH₂C≡N | 1-methyl-1H-pyrazol-4-yl |
| I-026 | CH₃ | –CH₂CH₂C≡N | oxazol-2-yl |
| I-027 | CH₃ | –CH₂CH₂C≡N | –CF₃ |
| I-028 | CH₃ | –CH₂CH₂C≡N | –CH₂OCH₃ |
| I-029 | CH₃ | –CH₂CH₂C≡N | –CH₂-(4-chloro-1H-pyrazol-1-yl) |
| I-030 | CH₃ | –CH₂CH₂C≡N | –C(O)CH₃ |
| I-031 | CH₃ | –CH₂CH₂C≡N | –C(O)OCH₃ |

TABLE 1-continued (I-1)

| No. | R¹ | G | T |
|---|---|---|---|
| I-032 | CH₃ | -CH₂CH₂C≡N | -CH₂C(O)OCH₂CH₃ |
| I-033 | CH₃ | -CH₂CH₂C≡N | -CH₂C(O)OCH₂CF₃ |
| I-034 | CH₃ | -CH₂CH₂C≡N | -CH₂C(O)O-cyclobutyl |
| I-035 | CH₃ | -CH₂CH₂C≡N | -NH-cyclopropyl |
| I-036 | CH₃ | -CH₂CH₂C≡N | -NH-(2,6-dichlorophenyl) |
| I-037 | CH₃ | -CH₂CH₂C≡N | -NH-(3-fluoropyridin-2-yl) |
| I-038 | CH₃ | -CH₂CH₂C≡N | -NH-(3-trifluoromethylpyridin-2-yl) |
| I-039 | CH₃ | -CH₂CH₂C≡N | -NH-(2,4-dichloropyridin-3-yl) |
| I-040 | CH₃ | -CH₂CH₂C≡N | -NH-(1-methyl-1H-pyrazol-5-yl) |
| I-041 | H | -CH₂CH₂CF₃ | -CH₃ |
| I-042 | H | -CH₂CH₂CF₃ | -cyclopropyl |
| I-043 | H | -CH₂CH₂CF₃ | -phenyl |
| I-044 | H | -CH₂CH₂CF₃ | -(3-trifluoromethylphenyl) |
| I-045 | H | -CH₂CH₂CF₃ | -(1-methyl-1H-pyrazol-4-yl) |
| I-046 | H | -CH₂CH₂CF₃ | -(oxazol-2-yl) |
| I-047 | H | -CH₂CH₂CF₃ | -CF₃ |
| I-048 | H | -CH₂CH₂CF₃ | -CH₂OCH₃ |

TABLE 1-continued (I-1)

| No. | R¹ | G | T |
|---|---|---|---|
| I-049 | H | CH₂CF₃ | -CH₂-(4-Cl-pyrazol-1-yl) |
| I-050 | H | CH₂CF₃ | -C(O)CH₃ |
| I-051 | H | CH₂CF₃ | -C(O)OCH₃ |
| I-052 | H | CH₂CF₃ | -C(O)OCH₂CH₃ |
| I-053 | H | CH₂CF₃ | -C(O)OCH₂CF₃ |
| I-054 | H | CH₂CF₃ | -C(O)O-cyclobutyl |
| I-055 | H | CH₂CF₃ | -NH-cyclopropyl |
| I-056 | H | CH₂CF₃ | -NH-(2,6-dichlorophenyl) |
| I-057 | H | CH₂CF₃ | -NH-(3-F-pyridin-2-yl) |
| I-058 | H | CH₂CF₃ | -NH-(3-CF₃-pyridin-2-yl) |
| I-059 | H | CH₂CF₃ | -NH-(2,4-dichloropyridin-3-yl) |
| I-060 | H | CH₂CF₃ | -NH-(1-methylpyrazol-5-yl) |
| I-061 | CH₃ | CH₂CF₃ | -CH₃ |
| I-062 | CH₃ | CH₂CF₃ | -cyclopropyl |
| I-063 | CH₃ | CH₂CF₃ | -phenyl |
| I-064 | CH₃ | CH₂CF₃ | -(3-CF₃-phenyl) |

TABLE 1-continued (I-1)

| No. | R¹ | G | T |
|---|---|---|---|
| I-065 | CH₃ | -CH₂CF₃ | 1-methyl-pyrazol-4-yl |
| I-066 | CH₃ | -CH₂CF₃ | oxazol-2-yl |
| I-067 | CH₃ | -CH₂CF₃ | -CF₃ |
| I-068 | CH₃ | -CH₂CF₃ | -CH₂-O-CH₃ |
| I-069 | CH₃ | -CH₂CF₃ | -CH₂-(4-chloro-pyrazol-1-yl) |
| I-070 | CH₃ | -CH₂CF₃ | -C(O)CH₃ |
| I-071 | CH₃ | -CH₂CF₃ | -C(O)OCH₃ |
| I-072 | CH₃ | -CH₂CF₃ | -C(O)OCH₂CH₃ |
| I-073 | CH₃ | -CH₂CF₃ | -C(O)OCH₂CF₃ |
| I-074 | CH₃ | -CH₂CF₃ | -C(O)O-cyclobutyl |
| I-075 | CH₃ | -CH₂CF₃ | -NH-cyclopropyl |
| I-076 | CH₃ | -CH₂CF₃ | -NH-(2,6-dichlorophenyl) |
| I-077 | CH₃ | -CH₂CF₃ | -NH-(3-fluoropyridin-2-yl) |
| I-078 | CH₃ | -CH₂CF₃ | -NH-(3-trifluoromethylpyridin-2-yl) |
| I-079 | CH₃ | -CH₂CF₃ | -NH-(2,4-dichloropyridin-3-yl) |
| I-080 | CH₃ | -CH₂CF₃ | -NH-(1-methylpyrazol-5-yl) |

TABLE 1-continued (I-1)

| No. | R¹ | G | T |
|---|---|---|---|
| I-081 | H | -CH₂CH₂CN | -NH-(2,6-difluorophenyl) |
| I-082 | H | -CH₂CH₂CN | -NH-(2,6-dimethylphenyl) |
| I-083 | H | -CH₂CH₂CN | -NH-(2-chloro-6-cyanophenyl) |
| I-084 | H | -CH₂CH₂CN | -CH₂Cl |
| I-085 | H | -CH₂CH₂CN | thiazol-2-yl |
| I-086 | H | -CH₂CH₂CN | -CF(CF₃)₂ (pentafluoroethyl-type) |
| I-087 | H | -CH₂CH₂CN | -CHF₂ |
| I-088 | H | -CH₂CH₂CN | -O-C(=O)-CH₂-cyclobutyl |
| I-089 | H | -CH₂CH₂CN | -O-C(=O)-cyclopropyl |
| I-090 | H | -CH₂CH₂CN | 1-methyl-1H-pyrazol-3-yl |
| I-091 | H | -CH₂CH₂CN | isoxazol-3-yl |
| I-092 | H | -CH₂CH₂CN | 5-(trifluoromethyl)furan-2-yl |
| I-093 | H | -CH₂CH₂CN | 3-phenyl-1,2,4-oxadiazol-5-yl |
| I-094 | H | -CH₂CH₂CN | -CH=N-OCH₃ |
| I-095 | CH₃ | -CH₂CH₂CN | -CH₂Cl |
| I-096 | CH₃ | -CH₂CH₂CN | 1-methyl-1H-pyrazol-3-yl |

$^1$H NMR data of compounds as per Table 1, unless already given in the Synthesis Examples 1 to 9:

I-001: $^1$H NMR (400.2 MHz, CD3CN):

δ=10.0397 (1.2); 10.0230 (1.5); 7.7420 (0.7); 7.7388 (0.7); 7.7234 (0.9); 7.7202 (1.5); 7.7171 (0.9); 7.7016 (0.9); 7.6984 (0.9); 7.4608 (1.4); 7.4390 (1.2); 7.2418 (0.7); 7.2391 (0.6); 7.2229 (1.2); 7.2065 (0.6); 7.2038 (0.6); 4.2653 (2.4); 4.2487 (4.9); 4.2321 (2.4); 2.8877 (2.5); 2.8711 (5.0); 2.8545 (2.4); 2.4678 (16.0); 2.1497 (25.0); 1.9638 (0.5); 1.9519 (10.3); 1.9457 (19.6); 1.9396 (27.6); 1.9334 (19.0); 1.9272 (9.8); −0.0002 (1.6)

I-002: $^1$H NMR (600.1 MHz, d$_6$-DMSO):

δ=9.9812 (0.5); 9.9701 (0.5); 7.8332 (0.9); 7.8267 (1.0); 4.7891 (0.4); 4.3275 (0.5); 4.3164 (1.1); 4.3053 (0.6); 3.3260 (16.0); 3.0196 (0.5); 3.0085 (1.2); 2.9974 (0.6); 2.5055 (7.0); 2.5027 (9.1); 2.4999 (7.1); 0.9214 (0.4); 0.9161 (0.7); 0.9090 (0.5); 0.8265 (0.5); 0.8205 (0.4); 0.8134 (0.5); 0.8075 (0.4); −0.0001 (0.9)

I-003: $^1$H NMR (400.2 MHz, d$_6$-DMSO):

δ=12.8908 (0.5); 10.0546 (5.4); 10.0380 (5.5); 9.8618 (1.5); 9.8452 (1.6); 8.1348 (3.0); 7.9567 (4.6); 7.9392 (5.3); 7.9357 (4.7); 7.9228 (1.8); 7.9140 (1.6); 7.9113 (1.6); 7.9011 (4.8); 7.8981 (5.0); 7.8835 (5.0); 7.8811 (4.6); 7.8702 (7.1); 7.8494 (2.3); 7.7001 (9.0); 7.6826 (10.6); 7.6790 (8.0); 7.6428 (1.0); 7.6244 (2.6); 7.6058 (1.8); 7.5207 (3.7); 7.5012 (5.8); 7.4940 (2.1); 7.4821 (3.7); 7.4757 (5.5); 7.4703 (1.7); 7.4572 (4.2); 7.4349 (1.0); 7.4313 (1.1); 7.4195 (10.6); 7.4011 (16.0); 7.3835 (6.3); 7.3805 (4.8); 4.7903 (10.4); 4.7772 (0.4); 4.3206 (1.8); 4.3039 (3.7); 4.2867 (2.6); 4.2804 (5.5); 4.2637 (11.3); 4.2471 (5.5); 3.3300 (24.9); 3.3034 (1.0); 3.2854 (0.6); 3.0084 (2.0); 2.9918 (4.6); 2.9819 (6.5); 2.9755 (3.2); 2.9653 (13.5); 2.9487 (5.9); 2.6964 (2.0); 2.6767 (0.4); 2.6724 (0.5); 2.5078 (67.3); 2.5035 (84.3); 2.4992 (62.4); 2.3349 (0.4); 2.3305 (0.5); 2.3261 (0.4); 2.1783 (0.5); 2.1585 (0.4); 1.9023 (0.4); 0.1460 (0.4); 0.0077 (3.8); −0.0002 (89.6); −0.1494 (0.5)

I-005: $^1$H NMR (601.6 MHz, d$_6$-DMSO):

δ=10.2217 (1.8); 10.2105 (2.0); 8.7841 (4.7); 8.1573 (5.0); 8.1566 (5.0); 7.8719 (0.4); 7.8699 (0.4); 7.8574 (1.4); 7.8554 (1.5); 7.8444 (3.5); 7.8420 (2.2); 7.8296 (0.5); 7.3728 (0.8); 7.3694 (0.8); 7.3617 (1.7); 7.3582 (1.6); 7.3507 (0.8); 7.3471 (0.8); 4.3427 (1.8); 4.3316 (3.9); 4.3204 (1.9); 3.8952 (16.0); 3.8577 (0.8); 3.3124 (40.0); 3.0201 (2.1); 3.0090 (4.8); 2.9979 (2.1); 2.5229 (0.4); 2.5198 (0.5); 2.5167 (0.4); 2.5079 (12.1); 2.5049 (26.1); 2.5019 (36.1); 2.4989 (25.8); 2.4959 (11.7); −0.0002 (1.3)

I-006: $^1$H NMR (400.2 MHz, d$_6$-DMSO):

δ=9.8163 (1.9); 9.8000 (1.9); 8.1786 (5.0); 8.1770 (4.9); 8.0151 (0.8); 8.0120 (0.8); 7.9965 (1.0); 7.9933 (1.9); 7.9902 (1.3); 7.9748 (1.4); 7.9717 (1.3); 7.9107 (2.3); 7.8889 (1.4); 7.4698 (1.1); 7.4667 (1.1); 7.4509 (1.9); 7.4348 (1.0); 7.4317 (1.0); 7.3521 (5.1); 7.3505 (4.9); 4.2393 (1.9); 4.2225 (4.3); 4.2057 (2.0); 3.3848 (0.5); 3.3259 (28.2); 3.1339 (1.1); 3.1218 (1.3); 3.1156 (3.5); 3.1036 (3.6); 3.0974 (3.6); 3.0854 (3.6); 3.0794 (1.3); 3.0673 (1.1); 2.9654 (2.3); 2.9487 (5.3); 2.9318 (2.2); 2.5249 (1.0); 2.5200 (1.5); 2.5114 (17.5); 2.5070 (34.4); 2.5024 (44.6); 2.4978 (32.2); 2.4934 (15.6); 1.2354 (1.0); 1.1951 (7.9); 1.1769 (16.0); 1.1587 (7.6); 0.0079 (1.3); −0.0002 (36.4); −0.0085 (1.2)

I-007: $^1$H NMR (601.6 MHz, d$_6$-DMSO):

δ=9.7947 (5.0); 9.7837 (5.0); 8.0526 (2.5); 8.0505 (2.5); 8.0402 (3.0); 8.0381 (5.5); 8.0360 (3.3); 8.0258 (3.4); 8.0236 (3.2); 7.9211 (5.6); 7.9065 (4.5); 7.4755 (1.0); 7.4735 (2.9); 7.4629 (5.0); 7.4521 (2.9); 7.4501 (2.7); 6.5214 (0.4); 4.7875 (0.4); 4.2878 (6.2); 4.2765 (13.7); 4.2653 (6.4); 3.4976 (0.4); 3.4873 (0.4); 3.3097 (18.8); 3.1768 (1.1); 3.1681 (1.1); 2.9909 (7.0); 2.9797 (16.0); 2.9685 (6.9); 2.7438 (0.6); 2.5243 (0.6); 2.5211 (0.8); 2.5181 (0.7); 2.5093 (17.1); 2.5062 (37.1); 2.5032 (51.7); 2.5002 (36.3); 2.4971 (16.4); −0.0002 (6.0)

I-008: $^1$H NMR (601.6 MHz, d$_6$-DMSO):

δ=9.9017 (2.4); 9.9002 (1.5); 9.8925 (1.6); 9.8908 (2.5); 9.8891 (1.5); 7.8792 (0.7); 7.8772 (0.7); 7.8677 (0.6); 7.8648 (2.0); 7.8626 (2.0); 7.8532 (2.3); 7.8512 (2.4); 7.8479 (2.1); 7.8466 (2.4); 7.8452 (2.6); 7.8437 (2.3); 7.8322 (0.8); 7.3900 (1.2); 7.3870 (1.2); 7.3787 (2.2); 7.3758 (2.2); 7.3676 (1.2); 7.3646 (1.2); 4.5218 (16.0); 4.2935 (2.7); 4.2824 (5.9); 4.2713 (2.8); 3.9286 (1.5); 3.3682 (0.5); 3.3604 (35.8); 3.3495 (0.3); 3.3073 (32.6); 3.2919 (2.8); 2.9932 (3.0); 2.9821 (7.0); 2.9710 (3.0); 2.6133 (0.3); 2.5226 (0.7); 2.5195 (0.9); 2.5164 (0.8); 2.5076 (19.8); 2.5046 (43.8); 2.5015 (61.7); 2.4985 (43.5); 2.4954 (19.5); 2.3856 (0.3); −0.0002 (3.0)

I-012: $^1$H NMR (601.6 MHz, d$_6$-DMSO):

δ=9.5920 (2.3); 9.5828 (1.7); 9.5812 (2.3); 9.5795 (1.6); 7.9874 (1.1); 7.9852 (1.1); 7.9750 (1.3); 7.9728 (2.5); 7.9707 (1.7); 7.9605 (1.7); 7.9583 (1.6); 7.9015 (2.7); 7.8870 (1.9); 7.4428 (1.3); 7.4408 (1.3); 7.4302 (2.4); 7.4196 (1.3); 7.4176 (1.3); 4.7866 (0.5); 4.2814 (2.1); 4.2695 (7.0); 4.2602 (3.1); 4.2577 (7.5); 4.2491 (5.8); 4.2459 (3.0); 4.2379 (2.7); 3.3079 (42.1); 2.9782 (3.0); 2.9670 (6.9); 2.9557 (3.0); 2.9448 (0.4); 2.6130 (0.3); 2.5221 (0.7); 2.5191 (0.9); 2.5159 (0.8); 2.5072 (19.8); 2.5042 (43.7); 2.5011 (61.2); 2.4980 (43.3); 2.4950 (19.6); 2.3855 (0.4); 1.2922 (7.4); 1.2804 (16.0); 1.2685 (7.2); 1.0434 (1.3); 1.0333 (1.2); −0.0002 (6.1)

I-018: $^1$H NMR (400.0 MHz, d$_6$-DMSO):

δ=10.6577 (0.8); 10.5424 (11.5); 9.6064 (6.6); 9.5900 (6.8); 9.5598 (0.5); 9.5435 (0.5); 8.6914 (5.4); 8.6822 (5.6); 8.2067 (5.2); 8.1901 (5.5); 8.1871 (5.4); 7.9285 (5.1); 7.9066 (7.8); 7.8382 (4.1); 7.8194 (6.0); 7.8002 (3.0); 7.7979 (3.0); 7.7761 (0.5); 7.7577 (0.4); 7.7073 (0.6); 7.6855 (0.4); 7.4333 (3.5); 7.4169 (6.7); 7.4080 (4.5); 7.3973 (6.2); 7.3886 (4.5); 7.3758 (4.0); 7.3547 (0.3); 4.4123 (6.1); 4.3956 (13.2); 4.3789 (6.5); 3.7506 (0.5); 3.5209 (4.2); 3.3250 (310.5); 3.0610 (7.3); 3.0443 (16.0); 3.0277 (7.0); 2.6757 (1.2); 2.6714 (1.6); 2.5067 (208.5); 2.5025 (269.0); 2.4983 (200.7); 2.3293 (1.6); 0.1458 (0.3); 0.0076 (3.1); −0.0002 (68.9)

I-023: $^1$H NMR (400.2 MHz, d$_6$-DMSO):

δ=10.0430 (2.3); 10.0271 (2.4); 7.7019 (2.2); 7.6829 (2.7); 7.6761 (3.7); 7.6731 (4.9); 7.6696 (2.3); 7.6610 (1.4); 7.6559 (6.2); 7.6521 (4.7); 7.5003 (0.4); 7.4909 (0.5); 7.4875 (1.0); 7.4840 (0.6); 7.4754 (0.7); 7.4693 (2.9); 7.4636 (1.0); 7.4544 (1.5); 7.4509 (2.6); 7.4474 (1.4); 7.4123 (4.3); 7.4091 (1.8); 7.3969 (3.1); 7.3934 (5.9); 7.3797 (0.9); 7.3758 (2.4); 7.3729 (1.4); 7.3338 (2.5); 7.3165 (3.1); 7.2982 (2.2); 4.8155 (1.1); 4.4416 (0.4); 4.4165 (2.6); 4.3997 (5.7); 4.3830 (2.7); 4.0378 (0.4); 4.0200 (0.4); 3.3225 (19.1); 3.0323 (0.4); 3.0100 (3.1); 2.9934 (7.4); 2.9765 (3.0); 2.7186 (16.0); 2.7040 (1.1); 2.6705 (0.4); 2.5241 (1.2); 2.5193 (1.8); 2.5106 (23.4); 2.5062 (47.8); 2.5016 (62.6); 2.4970 (44.6); 2.4924 (21.3); 2.3283 (0.4); 1.9887 (1.6); 1.1928 (0.5); 1.1749 (0.9); 1.1572 (0.4); 0.0080 (1.3); −0.0002 (40.6); −0.0085 (1.2)

I-028: $^1$H NMR (400.2 MHz, d$_6$-DMSO):

δ=9.9311 (2.0); 9.9147 (2.0); 7.6692 (1.9); 7.6503 (2.1); 7.3141 (2.1); 7.2972 (2.6); 7.2786 (1.9); 4.5380 (16.0); 4.4410 (2.6); 4.4242 (5.6); 4.4075 (2.6); 3.3659 (0.6); 3.3567 (34.1); 3.3225 (51.0); 3.0369 (3.0); 3.0203 (6.9); 3.0034 (2.8); 2.6956 (14.4); 2.6804 (0.4); 2.6755 (0.4); 2.6709 (0.6); 2.6665 (0.4); 2.5245 (1.4); 2.5198 (2.1);

2.5111 (29.7); 2.5066 (60.9); 2.5020 (80.0); 2.4974 (56.9); 2.4929 (27.1); 2.3333 (0.3); 2.3289 (0.5); 2.3241 (0.4); 1.0450 (0.4); 1.0298 (0.3); 0.0079 (1.6); −0.0002 (48.9); −0.0086 (1.5)

I-032: $^1$H NMR (400.2 MHz, d$_6$-DMSO):

δ=9.5885 (2.2); 9.5724 (2.2); 7.7802 (2.1); 7.7611 (2.3); 7.3736 (2.2); 7.3569 (2.6); 7.3550 (2.6); 7.3382 (2.0); 4.4007 (2.5); 4.3838 (5.5); 4.3669 (2.6); 4.2869 (2.2); 4.2691 (7.1); 4.2513 (7.2); 4.2335 (2.2); 3.3211 (25.5); 3.0244 (3.0); 3.0077 (7.0); 2.9907 (2.8); 2.6933 (15.4); 2.6752 (0.4); 2.6706 (0.5); 2.6659 (0.4); 2.5241 (1.4); 2.5194 (2.0); 2.5106 (26.2); 2.5062 (53.1); 2.5016 (69.5); 2.4970 (49.6); 2.4925 (23.7); 2.3283 (0.4); 1.9886 (1.4); 1.2958 (7.6); 1.2780 (16.0); 1.2601 (7.4); 1.1927 (0.4); 1.1750 (0.8); 1.1571 (0.4); 0.0080 (1.5); −0.0002 (48.6); −0.0085 (1.6)

I-038: $^1$H NMR (400.2 MHz, d$_6$-DMSO):

δ=10.6968 (4.9); 9.6375 (2.8); 9.6212 (2.8); 8.6931 (2.7); 8.6833 (2.7); 8.2083 (2.5); 8.1897 (2.6); 7.6208 (2.5); 7.6021 (2.8); 7.4096 (1.8); 7.3969 (2.1); 7.3915 (2.1); 7.3789 (1.7); 7.3466 (2.0); 7.3289 (3.1); 7.3112 (1.7); 4.5483 (2.8); 4.5318 (5.3); 4.5153 (2.8); 3.7800 (0.8); 3.3247 (37.1); 3.1001 (3.2); 3.0836 (6.2); 3.0671 (3.0); 2.7284 (16.0); 2.6724 (0.7); 2.5032 (82.9); 2.3300 (0.6); 1.0457 (0.6); 1.0307 (0.6); −0.0001 (2.6)

I-081: $^1$H NMR (400.0 MHz, d$_6$-DMSO):

δ=9.5631 (6.4); 9.5466 (6.7); 9.5307 (11.1); 7.9152 (5.1); 7.8932 (7.3); 7.8095 (3.6); 7.8068 (3.7); 7.7909 (4.4); 7.7881 (5.8); 7.7692 (2.9); 7.7665 (2.8); 7.4015 (3.3); 7.3990 (3.4); 7.3824 (6.9); 7.3658 (4.8); 7.3442 (4.1); 7.3391 (2.0); 7.3232 (3.0); 7.3075 (1.4); 7.2208 (0.8); 7.2158 (1.4); 7.2074 (8.5); 7.1872 (12.9); 7.1742 (1.3); 7.1667 (5.5); 7.1578 (1.1); 5.7551 (5.1); 4.4114 (5.9); 4.3948 (12.9); 4.3782 (6.3); 3.5238 (1.2); 3.3253 (79.6); 3.0734 (7.1); 3.0569 (16.0); 3.0402 (6.8); 2.6770 (0.4); 2.6725 (0.6); 2.6680 (0.4); 2.5258 (1.7); 2.5120 (36.6); 2.5079 (72.4); 2.5035 (93.7); 2.4991 (67.6); 2.4949 (33.4); 2.3404 (0.5); 2.3347 (0.4); 2.3302 (0.6); 2.3258 (0.4); 1.0467 (1.4); 1.0315 (1.4); 0.0076 (1.8); −0.0002 (50.6); −0.0083 (2.0)

I-082: $^1$H NMR (400.0 MHz, d$_6$-DMSO):

δ=9.6315 (1.0); 9.6148 (1.3); 9.5830 (0.4); 9.5663 (0.4); 9.5199 (1.6); 7.8940 (0.9); 7.8721 (1.2); 7.7605 (0.6); 7.7576 (0.6); 7.7420 (0.7); 7.7390 (1.0); 7.7200 (0.6); 7.7171 (0.6); 7.6803 (0.4); 7.6775 (0.4); 7.6680 (0.5); 7.3722 (0.6); 7.3697 (0.6); 7.3536 (0.4); 7.3373 (0.5); 7.3346 (0.5); 7.3093 (0.4); 7.3052 (0.4); 7.1257 (0.3); 7.1111 (0.8); 7.1013 (4.6); 7.0973 (4.3); 7.0874 (1.0); 7.0727 (0.4); 5.7543 (6.6); 4.4201 (1.0); 4.4033 (2.1); 4.3866 (1.0); 3.5336 (4.0); 3.3220 (65.6); 3.0759 (1.2); 3.0593 (2.6); 3.0425 (1.1); 2.6758 (0.3); 2.6710 (0.5); 2.6667 (0.3); 2.5244 (1.3); 2.5195 (2.0); 2.5109 (29.7); 2.5065 (60.1); 2.5021 (78.4); 2.4975 (56.2); 2.4932 (27.4); 2.3333 (0.4); 2.3288 (0.5); 2.3241 (0.4); 2.2205 (16.0); 2.2157 (8.0); 2.0936 (1.1); 1.8757 (1.1); 1.3358 (0.5); 1.2588 (0.4); 1.2497 (0.8); 1.2354 (0.7); 0.0079 (1.5); −0.0002 (47.6); −0.0085 (1.8)

I-083: $^1$H NMR (601.6 MHz, d$_6$-DMSO):

δ=10.2124 (3.7); 9.5591 (2.0); 9.5482 (2.1); 7.9315 (1.8); 7.9285 (2.6); 7.9262 (2.6); 7.9169 (2.6); 7.9150 (3.7); 7.9126 (2.8); 7.8784 (2.0); 7.8762 (2.0); 7.8654 (2.2); 7.8632 (2.0); 7.8382 (1.2); 7.8362 (1.3); 7.8259 (1.4); 7.8238 (2.0); 7.8216 (1.1); 7.8114 (1.0); 7.8094 (1.0); 7.4530 (2.1); 7.4397 (3.6); 7.4265 (3.0); 7.4137 (2.8); 7.4033 (1.1); 7.4012 (1.5); 5.7502 (0.5); 4.4169 (2.0); 4.4057 (4.3); 4.3945 (2.0); 3.3131 (2.1); 3.1715 (16.0); 3.0722 (2.4); 3.0611 (5.4); 3.0499 (2.4); 2.5230 (0.6);

2.5200 (0.7); 2.5168 (0.7); 2.5080 (15.8); 2.5050 (34.9); 2.5020 (49.0); 2.4990 (35.3); 2.4960 (16.5); 0.0053 (1.3); −0.0002 (43.5); −0.0057 (1.5)

I-085: $^1$H NMR (601.6 MHz, d$_6$-DMSO):

δ=19.9786 (0.4); 9.9058 (5.0); 9.8948 (5.1); 7.9819 (2.6); 7.9799 (2.8); 7.9675 (7.6); 7.9654 (6.7); 7.9603 (5.4); 7.9551 (9.6); 7.9532 (8.0); 7.8945 (6.1); 7.8803 (4.2); 7.4502 (2.9); 7.4481 (3.0); 7.4377 (5.0); 7.4269 (3.0); 7.4248 (2.8); 4.2661 (1.4); 4.2601 (5.8); 4.2490 (13.0); 4.2379 (6.2); 3.9746 (0.7); 3.7944 (0.7); 3.7842 (1.3); 3.7741 (1.6); 3.7640 (1.3); 3.7539 (0.7); 3.1709 (7.6); 3.1120 (0.4); 3.1042 (0.3); 2.9721 (6.9); 2.9610 (16.0); 2.9498 (7.0); 2.6133 (0.6); 2.5226 (1.4); 2.5195 (1.7); 2.5164 (1.5); 2.5076 (36.8); 2.5046 (81.5); 2.5016 (114.2); 2.4985 (82.1); 2.4955 (37.3); 2.3858 (0.6); 1.1896 (0.6); 1.1775 (1.2); 1.1654 (0.6); 1.0439 (12.9); 1.0337 (13.2); −0.0002 (12.8)

I-086: $^1$H NMR (601.6 MHz, d$_6$-DMSO):

δ=9.8310 (6.0); 9.8201 (6.1); 8.0605 (2.7); 8.0461 (5.8); 8.0336 (3.6); 8.0318 (3.4); 7.9177 (6.6); 7.9033 (5.3); 7.4609 (3.2); 7.4593 (3.2); 7.4485 (6.1); 7.4375 (3.1); 4.2878 (6.7); 4.2766 (14.1); 4.2663 (9.0); 3.5286 (0.3); 3.3171 (13.9); 3.1732 (0.6); 2.9873 (7.4); 2.9761 (16.0); 2.9649 (7.3); 2.9470 (1.0); 2.7870 (0.9); 2.7737 (0.4); 2.6155 (0.4); 2.5068 (50.5); 2.5039 (66.7); 2.5010 (49.6); 2.3875 (0.4); 1.9587 (0.7); −0.0002 (2.0)

I-087: $^1$H NMR (400.2 MHz, d$_6$-DMSO):

δ=9.7837 (5.4); 9.7674 (5.5); 8.0387 (2.2); 8.0356 (2.3); 8.0200 (2.8); 8.0169 (5.5); 8.0138 (3.8); 7.9983 (3.8); 7.9952 (3.8); 7.9338 (6.8); 7.9121 (4.3); 7.4834 (3.0); 7.4805 (3.0); 7.4644 (5.4); 7.4486 (2.9); 7.4455 (2.8); 7.2169 (3.6); 7.0809 (8.4); 6.9448 (4.0); 4.7896 (0.8); 4.3084 (6.4); 4.2917 (13.9); 4.2750 (6.7); 4.0382 (0.3); 4.0204 (0.3); 3.3438 (2.5); 3.0025 (7.2); 2.9859 (16.0); 2.9692 (6.9); 2.9444 (2.4); 2.7841 (1.8); 2.6758 (0.4); 2.6713 (0.5); 2.6667 (0.4); 2.5246 (1.8); 2.5111 (33.4); 2.5068 (64.7); 2.5022 (83.6); 2.4977 (61.9); 2.4933 (31.0); 2.3337 (0.4); 2.3291 (0.5); 2.3246 (0.4); 1.9892 (1.5); 1.9572 (1.9); 1.2499 (0.4); 1.1929 (0.4); 1.1751 (0.8); 1.1573 (0.4); 0.0080 (0.6); −0.0002 (16.6); −0.0084 (0.6)

I-088: $^1$H NMR (400.2 MHz, d$_6$-DMSO):

δ=9.5895 (3.2); 9.5734 (3.3); 7.9969 (1.3); 7.9752 (3.1); 7.9720 (2.2); 7.9566 (2.4); 7.9026 (3.9); 7.8808 (2.3); 7.4456 (1.7); 7.4299 (3.2); 7.4139 (1.7: 4.3869 (3.2); 4.3736 (1.7); 4.2623 (3.1); 4.2455 (6.8); 4.2288 (3.3); 4.2018 (10.6); 4.1847 (9.5); 3.3580 (3.0); 3.3444 (3.5); 3.3420 (3.6); 3.3283 (3.6); 3.3185 (40.6); 2.9774 (3.7); 2.9607 (8.6); 2.9437 (16.0); 2.7836 (9.6); 2.6749 (2.2); 2.6701 (2.1); 2.6604 (1.7); 2.5235 (5.1); 2.5100 (102.6); 2.5056 (199.5); 2.5011 (258.0); 2.4965 (190.2); 2.4921 (95.3); 2.3911 (0.5); 2.3731 (0.8); 2.3548 (1.0); 2.3368 (1.3); 2.3327 (1.6); 2.3279 (1.8); 2.3233 (1.4); 2.0278 (2.4); 2.0207 (2.0); 2.0160 (2.5); 2.0068 (2.4); 1.9987 (2.1); 1.9566 (10.6); 1.9369 (1.0); 1.9326 (0.8); 1.9243 (1.1); 1.9135 (1.2); 1.9025 (1.5); 1.8919 (1.1); 1.8826 (2.0); 1.8634 (2.2); 1.8601 (2.1); 1.8501 (2.0); 1.8407 (2.5); 1.8317 (4.5); 1.8269 (4.0); 1.8224 (3.9); 1.8184 (3.1); 1.8087 (3.91.7925 (2.7); 1.7859 (2.8); 1.7703 (2.0); 1.7604 (1.0); 1.7387 (0.6); 1.6889 (1.3); 1.6698 (1.1); 1.6647 (1.5); 1.6442 (1.0); 1.2352 (0.7); 1.2305 (0.7); 1.1923 (0.8); 1.1745 (1.2); 1.1566 (0.6); 0.0079 (1.8); −0.0002 (52.5); −0.0084 (2.2)

I-090: $^1$H NMR (400.2 MHz, d$_6$-DMSO):

δ=10.0762 (1.9); 10.0597 (1.9); 7.8926 (0.6); 7.8733 (1.6); 7.8710 (1.5); 7.8553 (1.8); 7.8534 (1.8); 7.8414 (2.4); 7.8215 (0.8); 7.6768 (3.1); 7.6713 (3.2); 7.3921 (0.9); 7.3885 (0.9); 7.3752 (1.7); 7.3715 (1.7); 7.3583 (1.0);

7.3545 (0.9); 6.9273 (3.2); 6.9219 (3.2); 4.7849 (1.0); 4.2900 (1.9); 4.2733 (3.9); 4.2568 (1.9); 4.1529 (0.4); 3.8955 (16.0); 3.3276 (13.8); 3.1693 (2.9); 3.1148 (0.4); 3.1030 (0.5); 3.0969 (0.5); 3.0848 (0.4); 2.9876 (2.2); 2.9711 (4.6); 2.9544 (2.1); 2.6712 (0.4); 2.5522 (0.4); 2.5353 (1.0); 2.5064 (49.2); 2.5023 (61.8); 2.4982 (48.5); 2.3287 (0.4); 1.1950 (0.8); 1.1767 (1.6); 1.1586 (0.8); 0.1461 (0.4); −0.0002 (67.9); −0.1494 (0.4)

I-091: $^1$H NMR (400.2 MHz, d$_6$-DMSO):
δ=10.0717 (5.7); 10.0551 (5.8); 8.7350 (13.3); 8.7303 (13.3); 8.0201 (2.3); 8.0170 (2.3); 8.0017 (2.8); 7.9985 (5.6); 7.9953 (4.0); 7.9800 (4.2); 7.9769 (4.0); 7.9262 (6.7); 7.9047 (4.0); 7.5654 (13.0); 7.5607 (13.0); 7.4718 (3.1); 7.4686 (3.1); 7.4534 (5.3); 7.4517 (5.2); 7.4368 (3.0); 7.4335 (2.8); 5.7554 (0.4); 4.3245 (6.0); 4.3078 (13.1); 4.2912 (6.3); 3.3256 (31.3); 3.0053 (7.0); 2.9887 (16.0); 2.9720 (6.7); 2.6770 (0.3); 2.6724 (0.5); 2.6678 (0.3); 2.5258 (1.6); 2.5209 (2.5); 2.5124 (29.9); 2.5080 (59.3); 2.5034 (77.9); 2.4988 (57.5); 2.4944 (28.7); 2.3348 (0.4); 2.3302 (0.5); 2.3257 (0.4); 0.1460 (0.6); 0.0160 (0.5); 0.0079 (5.1); −0.0002 (125.5); −0.0085 (5.3); −0.1495 (0.6)

I-092: $^1$H NMR (400.2 MHz, d$_6$-DMSO):
δ=10.0983 (5.9); 10.0817 (6.2); 8.1338 (5.8); 8.1319 (5.6); 8.1246 (6.0); 8.1228 (5.6); 7.9862 (2.1); 7.9832 (2.1); 7.9680 (2.6); 7.9646 (5.4); 7.9614 (4.2); 7.9463 (4.7); 7.9433 (4.5); 7.9139 (7.1); 7.8926 (3.5); 7.4598 (3.2); 7.4563 (3.1); 7.4422 (5.5); 7.4391 (5.4); 7.4250 (3.1); 7.4214 (2.9); 7.4057 (5.6); 7.4029 (5.6); 7.3998 (3.9); 7.3964 (5.6); 7.3937 (5.1); 4.3497 (5.7); 4.3331 (12.6); 4.3165 (6.0); 4.0563 (0.8); 4.0385 (2.5); 4.0207 (2.6); 4.0029 (0.8); 3.3229 (90.2); 3.0178 (6.9); 3.0013 (16.0); 2.9846 (6.7); 2.6806 (0.4); 2.6762 (0.8); 2.6716 (1.1); 2.6671 (0.8); 2.5251 (3.5); 2.5202 (5.3); 2.5117 (66.9); 2.5072 (131.7); 2.5027 (171.4); 2.4981 (124.9); 2.4938 (61.4); 2.3385 (0.4); 2.3341 (0.8); 2.3295 (1.1); 2.3250 (0.8); 1.9891 (11.0); 1.1934 (3.0); 1.1756 (5.9); 1.1578 (3.0); 0.1460 (1.3); 0.0189 (0.4); 0.0182 (0.4); 0.0079 (10.5); −0.0002 (267.8); −0.0085 (10.9); −0.0254 (0.4); −0.1495 (1.3)

I-093: $^1$H NMR (400.2 MHz, d$_6$-DMSO):
δ=9.7394 (2.2); 9.7233 (2.3); 8.1035 (1.0); 8.1004 (1.0); 8.0903 (0.4); 8.0836 (4.2); 8.0800 (5.0); 8.0696 (1.3); 8.0641 (4.0); 8.0598 (5.0); 7.9720 (2.6); 7.9502 (1.9); 7.6623 (0.3); 7.6449 (1.2); 7.6425 (1.3); 7.6356 (1.0); 7.6322 (2.2); 7.6272 (6.0); 7.6227 (3.3); 7.6157 (1.2); 7.6076 (3.7); 7.5967 (0.6); 7.5927 (1.1); 7.5855 (0.8); 7.5388 (1.3); 7.5360 (1.2); 7.5200 (2.4); 7.5038 (1.2); 7.5010 (1.2); 5.7554 (1.6); 4.7907 (0.5); 4.3456 (0.6); 4.3373 (0.6); 4.2369 (2.0); 4.2200 (4.2); 4.2032 (2.1); 3.7770 (0.4); 3.3269 (10.9); 2.9604 (2.5); 2.9437 (5.8); 2.9268 (2.4); 2.5257 (0.6); 2.5209 (0.9); 2.5124 (11.8); 2.5079 (23.5); 2.5033 (30.8); 2.4987 (22.6); 2.4943 (11.2); 1.0466 (16.0); 1.0314 (15.6); 0.0080 (2.2); −0.0002 (55.7); −0.0085 (2.2)

I-096: $^1$H NMR (400.2 MHz, d$_6$-DMSO):
δ=10.0488 (1.2); 10.0331 (1.3); 7.6712 (1.4); 7.6674 (3.2); 7.6616 (2.9); 7.6527 (1.3); 7.3038 (1.3); 7.2864 (1.7); 7.2682 (1.2); 6.8399 (3.4); 6.8342 (3.3); 4.4290 (1.3); 4.4123 (2.9); 4.3956 (1.4); 4.3453 (1.2); 4.3350 (1.2); 3.8908 (15.4); 3.7930 (0.4); 3.7828 (0.4); 3.7778 (0.5); 3.7676 (0.5); 3.7626 (0.4); 3.7523 (0.4); 3.3235 (14.5); 3.0188 (1.6); 3.0022 (3.8); 2.9855 (1.6); 2.7062 (8.4); 2.5243 (0.7); 2.5195 (1.0); 2.5109 (14.1); 2.5064 (28.5); 2.5018 (37.1); 2.4972 (26.2); 2.4927 (12.4); 1.0452 (16.0); 1.0391 (0.4); 1.0299 (15.8); 0.0080 (0.8); −0.0002 (26.0); −0.0085 (0.8)

The determination of the [M+H]$^+$ by LC-MS in the acidic range was carried out at pH 2.7 using the mobile phases acetonitrile (containing 0.1% formic acid) and water; linear gradient from 10% acetonitrile to 95% acetonitrile, instrument: Agilent 1100 LC system, Agilent MSD system, HTS PAL.

The log P values reported in the tables and preparation examples above were determined in accordance with EEC directive 79/831 Annex V.A8 by HPLC (High Performance Liquid Chromatography) using a reversed-phase column (C18). Temperature 43° C. The calibration is effected with unbranched alkan-2-ones (having 3 to 16 carbon atoms), for which the log P values are known.

The determination of the $^1$H NMR data was effected with a Bruker Avance 400 or Bruker Avance III 600 equipped with a sample flow head (capacity 60 μl), with tetramethylsilane as reference (0.0) and the solvents CD$_3$CN, CDCl$_3$ or D$_6$-DMSO.

NMR Peak List Method

The $^1$H NMR data of selected examples are stated in the form of $^1$H NMR peak lists. For each signal peak, first the δ value in ppm and then the signal intensity in round brackets are listed. The pairs of δ value-signal intensity numbers for differing signal peaks are listed with separation from one another by semicolons.

The peak list for one example therefore has the form of:
δ$_1$ (intensity$_1$); δ$_2$ (intensity$_2$); . . . ; δ$_i$ (intensity$_i$); . . . ; δ$_n$ (intensity$_n$)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of $^1$H NMR spectra is accomplished using tetramethylsilane and/or the chemical shift of the solvent, particularly in the case of spectra which are measured in DMSO. Therefore, the tetramethylsilane peak may but need not occur in NMR peak lists.

The lists of the $^1$H NMR peaks are similar to the conventional $^1$H NMR printouts and thus usually contain all peaks listed in a conventional NMR interpretation.

In addition, like conventional $^1$H NMR printouts, they may show solvent signals, signals of stereoisomers of the target compounds which likewise form part of the subject-matter of the invention, and/or peaks of impurities.

In the reporting of compound signals within the delta range of solvents and/or water, our lists of $^1$H NMR peaks show the standard solvent peaks, for example peaks of DMSO in DMSO-D$_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. The peaks thereof can thus help in identifying reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the peak picking in question in conventional $^1$H NMR interpretation.

Further details of $^1$H NMR peak lists can be found in the Research Disclosure Database Number 564025.

Use Examples

The examples below demonstrate the insecticidal and acaricidal action of the compounds according to the invention. Here, the compounds according to the invention mentioned refer to the compounds listed in Table 1 with the corresponding reference number (No.):

*Ctenocephalides felis*—In Vitro Contact Tests with Adult Cat Fleas

For the coating of the test tubes, 9 mg of active compound are first dissolved in 1 ml of acetone p.a. and then diluted to the desired concentration with acetone p.a. 250 µl of the solution are distributed homogeneously on the inner walls and the base of a 25 ml test tube by turning and rocking on an orbital shaker (rocking rotation at 30 rpm for 2 h). With 900 ppm active compound solution and internal surface 44.7 cm$^2$, given homogeneous distribution, an area-based dose of 5 µg/cm$^2$ is achieved.

After the solvent has evaporated off, the tubes are populated with 5-10 adult cat fleas (*Ctenocephalides felis*), sealed with a perforated plastic lid and incubated in a horizontal position at room temperature and ambient humidity. After 48 h, efficacy is determined. To this end, the tubes are stood upright and the fleas are knocked to the base of the tube. Fleas which remain motionless at the base or are moved in an uncoordinated manner are considered to be dead or moribund.

A substance shows good efficacy against *Ctenocephalides felis* if at least 80% efficacy was achieved in this test at an application rate of 5 µg/cm$^2$. 100% efficacy means that all the fleas were dead or moribund. 0% efficacy means that no fleas were harmed.

In this test, for example, the following compounds from the preparation examples showed an efficacy of 100% at an application rate of 5 µg/cm$^2$ (=500 g of ai/ha): I-016

In this test, for example, the following compounds from the preparation examples showed an efficacy of 80% at an application rate of 5 µg/cm$^2$ (=500 g of ai/ha): I-047

*Ctenocephalides felis*—Oral Test

Solvent: dimethyl sulfoxide

To produce a suitable preparation of active compound, 10 mg of active compound are mixed with 0.5 ml of dimethyl sulfoxide. Dilution with titrated cattle blood gives the desired concentration.

About 20 unfed adult cat fleas (*Ctenocephalides felis*) are placed into a chamber which is closed at the top and bottom with gauze. A metal cylinder whose bottom end is closed with parafilm is placed on to the chamber. The cylinder contains the blood/active compound preparation, which can be adsorbed by the fleas through the parafilm membrane.

After 2 days, the kill in % is determined. 100% means that all of the fleas have been killed; 0% means that none of the fleas have been killed.

In this test, for example, the following compounds from the preparation examples showed an efficacy of 85% at an application rate of 100 ppm: I-018

*Musca domestica* Test

Solvent: dimethyl sulfoxide

To produce a suitable preparation of active compound, 10 mg of active compound are mixed with 0.5 ml of dimethyl sulfoxide, and the concentrate is diluted with water to the desired concentration.

Vessels containing a sponge treated with sugar solution and the active compound preparation of the desired concentration are populated with 10 adult houseflies (*Musca domestica*).

After 2 days, the kill in % is determined. 100% means that all of the flies have been killed; 0% means that none of the flies have been killed.

In this test, for example, the following compounds from the preparation examples showed an efficacy of 100% at an application rate of 100 ppm: I-018

*Diabrotica Balteata*—Spray Test

Solvents: 78 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Preswollen wheat grains (*Triticum aestivum*) are incubated in a multiwell plate filled with agar and a little water for one day (5 seed grains per well). The germinated wheat grains are sprayed with an active compound preparation of the desired concentration. Subsequently, each well is infested with 10-20 *Diabrotica balteata* beetle larvae.

After 7 days, the efficacy in % is determined. 100% means that all wheat plants have grown as in the untreated non-infested control; 0% means that no wheat plant has grown.

In this test, for example, the following compounds from the preparation examples showed an efficacy of 100% at an application rate of 160 µg/well: I-047

*Myzus persicae*—Oral Test

Solvent: 100 parts by weight of acetone

To produce a suitable preparation of active compound, 1 part by weight of active compound is mixed with the stated parts by weight of solvent and made up with water to the desired concentration.

50 µl of the active compound preparation are transferred into microtiter plates and made up with 150 µl of IPL41 insect medium (33%+15% sugar) to a final volume of 200 µl. The plates are then sealed with parafilm which can be pierced by a mixed population of the green peach aphid (*Myzus persicae*) located in a second microtiter plate in order to take up the solution.

After 5 days, the efficacy in % is determined. 100% means that all the aphids have been killed; 0% means that none of the aphids have been killed.

In this test, for example, the following compounds from the preparation examples showed an efficacy of 100% at an application rate of 4 ppm: I-002, I-003, I-004, I-007, I-018, I-051, I-082, I-085, I-086, I-091, I-094

In this test, for example, the following compounds from the preparation examples showed an efficacy of 90% at an application rate of 4 ppm: I-005, I-081, I-083, I-087, I-092, I-093

*Myzus persicae*—Spray Test

Solvents: 78 parts by weight of acetone
1.5 parts by weight of dimethylformamide
Emulsifier: alkylaryl polyglycol ether To produce a suitable preparation of active compound, 1 part by weight of active compound is dissolved using the stated parts by weight of solvent and made up with water containing an emulsifier concentration of 1000 ppm until the desired concentration is attained. To produce further test concentrations, the preparation is diluted with emulsifier-containing water.

Discs of Chinese cabbage leaves (Brassica pekinensis) infested by all stages of the green peach aphid (Myzus persicae) are sprayed with an active compound preparation of the desired concentration.

After 5 days, the efficacy in % is determined. 100% means that all the aphids have been killed; 0% means that none of the aphids have been killed.

In this test, for example, the following compounds from the preparation examples showed an efficacy of 100% at an application rate of 500 g/ha: I-012, I-016

In this test, for example, the following compounds from the preparation examples showed an efficacy of 90% at an application rate of 500 g/ha: I-007, I-089

The invention claimed is:
1. A Compound of formula (I)

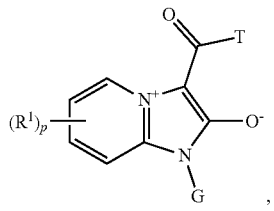

(I)

in which
T represents hydrogen, $C(R^{5a})(R^{5b})(R^{5c})$, $C_2$-$C_6$-alkenyl, $C_3$-$C_6$-alkynyl or $C_3$-$C_6$-cycloalkyl, where $C_2$-$C_6$-alkenyl, $C_3$-$C_6$-alkynyl and $C_3$-$C_6$-cycloalkyl may each optionally be mono- to trisubstituted and the substituents independently of one another are selected from the group consisting of halogen, and/or may each optionally be monosubstituted and the substituent is selected from the group consisting of cyano, $C_1$-$C_4$ alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylsulfinyl and $C_1$-$C_4$-alkylsulfonyl,
or
T represents aryl, $C_1$-$C_6$-alkylenedioxyphenyl, hetaryl or $C_3$-$C_6$-heterocyclyl, where the radicals mentioned above may each optionally be mono- to pentasubstituted and the substituents independently of one another are selected from the group consisting of halogen, nitro, cyano, $C_1$-$C_4$-alkyl, $C_3$-$C_6$-heterocyclyl, $C_1$-$C_4$-haloalkyl, $C_1$-$C_4$-alkoxy, $C_1$-$C_4$-haloalkoxy, $C_2$-$C_4$-alkenyl, $C_3$-$C_4$-alkynyl, $C_1$-$C_4$-alkylthio, $C_1$-$C_4$-alkylsulfinyl, $C_1$-$C_4$-alkylcarbonyl, $C_3$-$C_6$-cycloalkylcarbonyl, $C_2$-$C_4$-alkenylcarbonyl, $C_1$-$C_4$-haloalkylcarbonyl, $C_1$-$C_4$-alkoxycarbonyl, $C_1$-$C_4$-alkylsulfonyl, $C_1$-$C_4$-haloalkylsulfonyl, aryl, hetaryl, heterocyclyl, aryl-$C_1$-$C_6$-alkyl and hetaryl-$C_1$-$C_6$-alkyl, where aryl, hetaryl, aryl-$C_1$-$C_6$-alkyl and hetaryl-$C_1$-$C_6$-alkyl for their part may each be mono- to trisubstituted and the substituents independently of one another are selected from the group consisting of halogen, cyano, $C_1$-$C_4$-alkyl, $C_1$-$C_4$-haloalkyl, $C_1$-$C_4$-alkoxy and $C_1$-$C_4$-haloalkoxy,
or
T represents $N(R^{7a})(R^{7b})$ or $N(R^8)$—$N(R^{11a})(R^{11b})$,
or
T represents $C(=W)R^{12}$ or $C(=O)OR^{13}$,
W represents O or N—$OR^{15}$, G represents $C_1$-$C_6$-alkyl or $C_2$-$C_6$-alkenyl, where the radicals mentioned above are each mono- to pentasubstituted by halogen and/or mono- to disubstituted by cyano, $C_1$-$C_4$-alkoxy, $C_1$-$C_4$-alkylcarbonyl, $C_1$-$C_4$-alkoxycarbonyl, $C_1$-$C_4$-carbonyl-$C_1$-$C_4$-alkoxy or $C_1$-$C_4$-alkoximino-$C_1$-$C_4$-alkyl,
$R^1$ in each case represents hydrogen, halogen, cyano, $C_1$-$C_4$-alkyl, $C_1$-$C_4$-haloalkyl, $C_1$-$C_4$-alkoxy or $C_1$-$C_4$-haloalkoxy,
p represents 1 or 2,
$R^{5a}$ and $R^{5b}$ independently of one another represent hydrogen, halogen, cyano, $C_1$-$C_4$-alkyl, $C_1$-$C_4$-haloalkyl or $C_1$-$C_4$-alkoxy,
$R^{5c}$ represents hydrogen, fluorine, chlorine, bromine, cyano, $C_1$-$C_4$-alkoxycarbonyl, $C_1$-$C_4$-alkyl, $C_1$-$C_4$-alkoxy, $C_3$-$C_6$-cycloalkyl, $C_2$-$C_6$-alkenyl or $C_2$-$C_6$-alkynyl, where $C_1$-$C_4$-alkyl, $C_3$-$C_6$-cycloalkyl, $C_2$-$C_6$-alkenyl and $C_2$-$C_6$-alkynyl may each optionally be mono- to pentasubstituted and the substituents independently of one another are selected from the group consisting of halogen, and/or may each optionally be monosubstituted and the substituent is selected from the group consisting of nitro, cyano, $C_1$-$C_4$-haloalkyl, $C_1$-$C_4$-alkoxy, $C_1$-$C_4$-haloalkoxy, $C_1$-$C_4$-alkylcarbonyl and $C_1$-$C_4$-alkoxycarbonyl,
or
$R^{5c}$ represents aryl or C-bound hetaryl, where the radicals mentioned above may each optionally be mono- to pentasubstituted and the substituents independently of one another are selected from the group consisting of halogen, nitro, amino, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxycarbonyl, $C_1$-$C_4$-alkylthio, $C_1$-$C_4$-alkylsulfinyl and $C_1$-$C_4$-alkylsulfonyl,
or
$R^{5c}$ represents Y,
Y represents one of the radicals Y-1 to Y-23

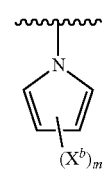

Y-1

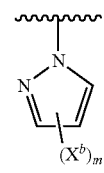

Y-2

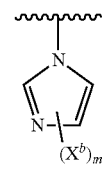

Y-3

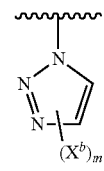

Y-4

-continued
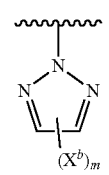 Y-5
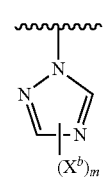 Y-6
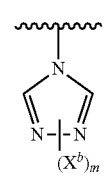 Y-7
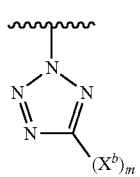 Y-8
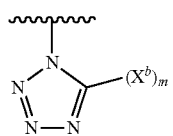 Y-9
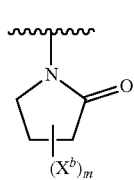 Y-10
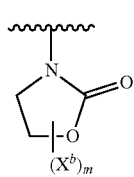 Y-11
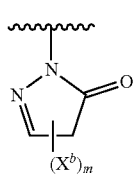 Y-12
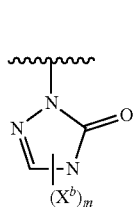 Y-13
-continued
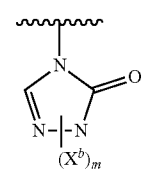 Y-14
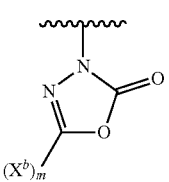 Y-15
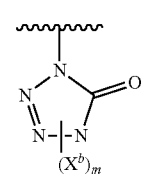 Y-16
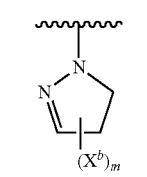 Y-17
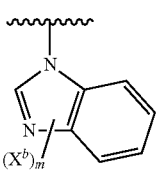 Y-18
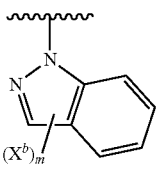 Y-19
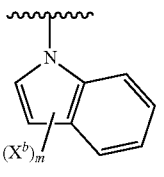 Y-20
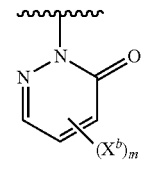 Y-21
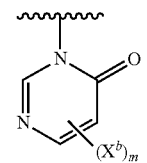 Y-22

-continued

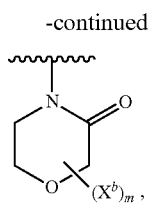

Y-23

$X^b$ represents halogen, nitro, cyano, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_3$-$C_6$-alkynyl, $C_1$-$C_6$-alkylthio, $C_1$-$C_6$-alkylcarbonyl, $C_3$-$C_6$-cycloalkylcarbonyl, $C_2$-$C_6$-alkenylcarbonyl, $C_1$-$C_6$-haloalkylcarbonyl, $C_1$-$C_6$-alkoxycarbonyl, $C_1$-$C_6$-alkylsulfonyl, $C_1$-$C_6$-alkylsulfinyl, $C_1$-$C_6$-haloalkylsulfonyl, $C_1$-$C_6$-alkylaminocarbonyl, di-($C_1$-$C_6$)-alkylaminocarbonyl, $C_1$-$C_6$-alkylcarbonylamino, aryl or hetaryl, where aryl and hetaryl for their part may each optionally be mono- to trisubstituted and the substituents independently of one another are selected from the group consisting of halogen, cyano, nitro, hydroxy, $C_1$-$C_6$-alkyl, $C_2$-$C_6$-alkenyl, $C_2$-$C_6$-alkynyl, $C_1$-$C_6$-alkoxy, $C_1$-$C_6$-haloalkyl, $C_1$-$C_6$-haloalkoxy and $C_1$-$C_6$-alkylthio and where the ring nitrogen atoms in Y-13, Y-14 and Y-16 are not substituted by halogen, nitro, cyano, $C_1$-$C_4$-alkoxy, $C_1$-$C_4$-haloalkoxy or $C_1$-$C_4$-alkoxy-$C_1$-$C_4$-alkyloxy, m represents 0, 1 or 2, $R^{13}$ and $R^{15}$ independently of one another represent hydrogen, or represent $C_1$-$C_4$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl, $C_3$-$C_6$-heterocyclyl, $C_3$-$C_6$-heterocyclyl-$C_1$-$C_4$-alkyl, $C_3$-$C_6$-oxoheterocyclyl, $C_3$-$C_6$-dioxoheterocyclyl, phenyl, pyridyl, phenyl-$C_1$-$C_4$-alkyl or pyridyl-$C_1$-$C_4$-alkyl, where the radicals mentioned above may each optionally be mono- to trisubstituted and the substituents independently of one another are selected from the group consisting of halogen, and/or may each optionally be monosubstituted and the substituent is selected from the group consisting of nitro, cyano, $C_1$-$C_4$-alkyl, $C_1$-$C_4$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-alkoxycarbonyl, aryl and hetaryl, where aryl and hetaryl for their part may each optionally be mono- to trisubstituted and the substituents independently of one another are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy, $R^{7a}$ and $R^{11a}$ independently of one another represent hydrogen, $C_1$-$C_4$-alkyl, $C_1$-$C_4$-alkoxy, $C_1$-$C_4$-alkoxy-$C_1$-$C_4$-alkyl, $C_1$-$C_4$-alkoxycarbonyl or $C_1$-$C_6$-alkylcarbonyl, $R^{7b}$ and $R^{11b}$ independently of one another represent hydrogen, $C_1$-$C_6$-alkyl, or $C_3$-$C_6$-cycloalkyl, where the radicals mentioned above may each optionally be mono- to trisubstituted and the substituents independently of one another are selected from the group consisting of halogen, and/or may optionally be monosubstituted and the substituent is selected from the group consisting of cyano, nitro, hydroxy and $C_1$-$C_4$-alkoxy, $C_3$-$C_6$-cycloalkyl, aryl and hetaryl, where aryl, $C_3$-$C_6$-cycloalkyl and hetaryl for their part may be mono- to trisubstituted and the substituents independently of one another are selected from the group consisting of halogen, nitro, cyano, $C_1$-$C_4$-alkyl, $C_1$-$C_4$-haloalkyl, $C_1$-$C_4$-alkoxy and $C_1$-$C_4$-haloalkoxy, or $R^{7b}$ and $R^{11b}$ independently of one another represent aryl or hetaryl, where the radicals mentioned above may each optionally be mono- to trisubstituted and the substituents independently of one another are selected from the group consisting of halogen, nitro, amino, cyano, $C_1$-$C_4$ alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylsulfinyl and $C_1$-$C_4$-alkylsulfonyl, or $R^{7a}$ and $R^{7b}$ may be attached to one another via two to six carbon atoms and form a ring which may optionally additionally contain a further atom from the group consisting of O, S and N and which may optionally be mono- to tetrasubstituted and where the substituents independently of one another are selected from the group consisting of $C_1$-$C_2$-alkyl, fluorine, chlorine, bromine and $C_1$-$C_2$-alkoxy, or $R^{11a}$ and $R^{11b}$ may be attached to one another via two to six carbon atoms and form a ring which may optionally additionally contain a further atom from the group consisting of O, S and N and which may optionally be mono- to tetrasubstituted and where the substituents independently of one another are selected from the group consisting of $C_1$-$C_2$-alkyl, fluorine, chlorine, bromine and $C_1$-$C_2$-alkoxy, or $R^8$ represents hydrogen, $C_1$-$C_6$-alkyl, $C_3$-$C_6$-cycloalkyl, $C_1$-$C_6$-alkoxycarbonyl or $C_1$-$C_6$-alkylcarbonyl, and $R^{12}$ represents $C_1$-$C_6$-alkyl which may optionally be mono- to pentasubstituted and where the substituents independently of one another are selected from the group consisting of halogen, and/or which may optionally be monosubstituted and where the substituent is selected from the group consisting of nitro, cyano, $C_1$-$C_4$-alkoxy and $C_1$-$C_4$-haloalkoxy, or $R^{12}$ represents aryl or hetaryl, where the radicals mentioned above may each optionally be mono- to trisubstituted and the substituents independently of one another are selected from the group consisting of halogen, nitro, cyano, $C_1$-$C_4$ alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylsulfinyl and $C_1$-$C_4$-alkylsulfonyl.

2. The compound according to claim 1, in which

T represents hydrogen, $C(R^{5a})(R^{5b})(R^{5c})$, $C_2$-$C_4$-alkenyl, $C_3$-$C_4$-alkynyl or $C_3$-$C_6$-cycloalkyl, where $C_2$-$C_4$-alkenyl, $C_3$-$C_4$-alkynyl or $C_3$-$C_6$-cycloalkyl may each optionally be mono- to trisubstituted and the substituents independently of one another are selected from the group consisting of halogen, and/or may each optionally be monosubstituted and the substituent is selected from the group consisting of cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylsulfinyl and $C_1$-$C_4$-alkylsulfonyl, or T represents phenyl, $C_1$-$C_4$-alkylenedioxyphenyl, naphthyl, furanyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidyl, thiophenyl, pyridazinyl, pyrazinyl, 1,2,3-triazinyl, 1,2,4-triazinyl, 1,3,5-triazinyl, benzofuranyl, indolyl, benzothiazolyl, benzoxazolyl, benzimidazolyl, pyrazolopyridinyl, quinolinyl, isoquinolinyl, cinnolinyl, azetidinyl, azolidinyl, azinanyl, oxetanyl, oxolanyl, oxanyl, dioxanyl, thiethanyl, thiolanyl, thianyl, or dihydroisoxazolyl, where the radicals mentioned above may each optionally be mono- to tetrasubstituted and the substituents independently of one another are selected from the group consisting of fluorine and chlorine, and/or may each optionally be mono- to disubstituted and the substituents independently of one another are selected from the group consisting of bromine, nitro, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-alkylsulfinyl, $C_1$-$C_4$-alkylsulfonyl, $C_1$-$C_4$-haloalkylsulfonyl, phenyl, pyridyl and morpholinyl, where in total at most five of the substituents mentioned above are present and where phenyl and pyridyl for their part may each additionally be mono- to trisubstituted and the substituents independently of one another are selected from the group consisting of halogen, cyano, $C_1$-$C_4$-alkyl, $C_1$-$C_4$-haloalkyl, $C_1$-$C_4$-alkoxy and $C_1$-$C_4$-haloalkoxy, or T represents $N(R^{7a})(R^{7b})$, or T represents $C(=W)R^{12}$ or $C(=O)OR^{13}$, W represents O or N—$OR^{15}$, G represents $C_1$-$C_4$-alkyl or $C_2$-$C_4$-alkenyl, where the radicals mentioned above are each mono- to trisubstituted by halogen and/or monosubstituted by cyano, $R^1$ represents hydrogen, fluorine, chlorine, methyl, ethyl, methoxy or ethoxy, p represents 1, $R^{5a}$ and $R^{5b}$ independently of one another represent hydrogen, halogen, $C_1$-$C_4$-alkyl or $C_1$-$C_4$-alkoxy, $R^{5c}$ represents hydrogen, fluorine, chlorine, bromine, $C_1$-$C_4$-alkoxycarbonyl, $C_1$-$C_4$-alkyl, $C_1$-$C_4$-alkoxy or $C_3$-$C_6$-cycloalkyl, where $C_1$-$C_4$-alkyl and $C_3$-$C_6$-cycloalkyl may each optionally be mono- to trisubstituted and the substituents independently of one another are selected from the group consisting of halogen, and/or may each optionally be monosubstituted and the substituent is selected from the group consisting of cyano, $C_1$-$C_4$-haloalkyl, $C_1$-$C_4$-alkoxy and $C_1$-$C_4$-alkoxycarbonyl, or $R^{5c}$ represents phenyl or C-bound pyridyl, where the radicals mentioned above may each optionally be mono- to trisubstituted and the substituents independently of one another are selected from the group consisting of halogen, nitro, cyano, $C_1$-$C_4$-alkyl, $C_1$-$C_4$-haloalkyl, $C_1$-$C_4$-alkoxy, $C_1$-$C_4$-haloalkoxy, $C_1$-$C_4$-alkoxycarbonyl, $C_1$-$C_4$-alkylthio, $C_1$-$C_4$-alkylsulfinyl and $C_1$-$C_4$-alkylsulfonyl, or $R^{5c}$ represents Y, Y represents one of the radicals Y-2, Y-3, Y-4, Y-5, Y-6 or Y-7, $X^b$ represents halogen, cyano, methyl, ethyl, trifluoromethyl, difluoromethyl, methylaminocarbonyl, methylcarbonylamino, methoxy, ethoxy, trifluoromethoxy, methylthio, ethylthio, methylsulfinyl, methylsulfonyl or methoxycarbonyl, m represents 0, 1 or 2, $R^{13}$ and $R^{15}$ independently of one another represent hydrogen, or represent $C_1$-$C_4$-alkyl, $C_3$-$C_6$-cycloalkyl, $C_3$-$C_6$-heterocyclyl or $C_3$-$C_6$-dioxoheterocyclyl, where the radicals mentioned above may each optionally be mono- to trisubstituted and the substituents independently of one another are selected from the group consisting of halogen, and/or may each optionally be monosubstituted and the substituent is selected from the group consisting of cyano, $C_1$-$C_4$-alkyl, $C_1$-$C_4$-haloalkyl, $C_3$-$C_6$-cycloalkyl, $C_1$-$C_4$-alkoxy, $C_1$-$C_4$-alkylthio, $C_1$-$C_4$-alkylsulfinyl, $C_1$-$C_4$-alkylsulfonyl, $C_1$-$C_4$-alkoxycarbonyl, phenyl and pyridyl, where phenyl and pyridyl for their part may each be mono- to trisubstituted and the substituents independently of one another are selected from the group consisting of halogen, cyano, nitro, $C_1$-$C_4$-alkyl, $C_1$-$C_4$-haloalkyl, $C_1$-$C_4$-alkoxy and $C_1$-$C_4$-haloalkoxy, $R^{7a}$ represents hydrogen or $C_1$-$C_4$-alkyl, $R^{7b}$ represents hydrogen, or represents $C_1$-$C_6$-alkyl or $C_3$-$C_6$-cycloalkyl, where the radicals mentioned above may each optionally be mono- to trisubstituted and the substituents independently of one another are selected from the group consisting of halogen, and/or may optionally be monosubstituted and the substituent is selected from the group consisting of $C_3$-$C_6$-cycloalkyl and phenyl, where $C_3$-$C_6$-cycloalkyl and phenyl for their part may be mono- to trisubstituted and the substituents independently of one another are selected from the group consisting of halogen, $C_1$-$C_4$-alkyl, $C_1$-$C_4$-haloalkyl and $C_1$-$C_4$-alkoxy, or $R^{7b}$ represents phenyl, pyridyl or pyrazolyl, where the radicals mentioned above may each optionally be mono- to trisubstituted and the substituents independently of one another are selected from the group consisting of halogen, cyano, $C_1$-$C_4$-alkyl, $C_1$-$C_4$-haloalkyl, $C_1$-$C_4$-alkoxy, $C_1$-$C_4$-alkylthio, $C_1$-$C_4$-alkylsulfinyl and $C_1$-$C_4$-alkylsulfonyl, or $R^{7a}$ and $R^{7b}$ may be attached to one another via two to six carbon atoms and form a ring which may optionally additionally contain a further atom from the group consisting of O, S and N and which may optionally be mono- to trisubstituted and where the substituents independently of one another are selected from the group consisting of methyl, ethyl, fluorine, methoxy and ethoxy, and $R^{12}$ represents $C_1$-$C_4$-alkyl which may optionally be mono- to pentasubstituted and where the substituents independently of one another are selected from the group consisting of halogen, or $R^{12}$ represents phenyl which may optionally be mono- to trisubstituted and where the substituents independently of one another are selected from the group consisting of halogen.

3. The compound according to claim 1, in which

T represents hydrogen, $C(R^{5a})(R^{5b})(R^{5c})$, ethenyl, propenyl, cyclopropyl, cyclobutyl, cyclopentyl or cyclohexyl, where ethenyl, propenyl, cyclopropyl, cyclobutyl, cyclopentyl and cyclohexyl may each optionally be mono- to trisubstituted and the substituents independently of one another are selected from the group consisting of fluorine and chlorine, and/or may each optionally be monosubstituted and the substituent is selected from the group consisting of cyano, methyl, ethyl, trifluoromethyl and methoxy, or T represents phenyl, pyridyl, pyrimidyl, thiophenyl, furanyl, pyrrolyl, thiazolyl, isothiazolyl, 1,3-oxazolyl, 1,2-oxazolyl, pyrazolyl, imidazolyl, 1,2,4-oxadiazolyl, pyrazolopyridinyl, benzothiazolyl, benzofuranyl, benzoxazolyl, quinolinyl, oxolanyl or dihydroisoxazolyl, where the radicals mentioned above may each optionally be mono- to tetrasubstituted and the substituents independently of one another are selected from the group consisting of fluorine and chlorine, and/or may each optionally be mono- to disubstituted and the substituents independently of one another are selected from the group consisting of bromine, cyano, methyl, ethyl, difluoromethyl, trifluoromethyl, trifluoroethyl, pentafluoroethyl, trifluoropropyl, methoxy, ethoxy, trifluoromethoxy, methylthio, methylsulfinyl, methylsulfonyl, morpholinyl and phenyl, or T represents $N(R^{7a})(R^{7b})$, or T represents $C(=W)R^{12}$ or $C(=O)OR^{13}$, W represents O or $N-OR^{15}$, G represents cyanomethyl, 2-cyanoethyl, 2,2,2-trifluoroethyl or 3,3,3-trifluoropropyl, $R^1$ represents hydrogen or methyl, p represents 1, $R^{5a}$ and $R^{5b}$ independently of one another represent hydrogen, fluorine, chlorine, methyl, ethyl, methoxy or ethoxy, $R^{5c}$ represents hydrogen, fluorine, chlorine, bromine, cyano, methoxy or methoxycarbonyl, or represents methyl, ethyl, n-propyl, isopropyl, n-butyl, isobutyl, sec-butyl, tert-butyl, cyclopropyl or phenyl, where the radicals mentioned above may each optionally be mono- to trisubstituted and the substituents independently of one another are selected from the group consisting of fluorine and chlorine, and/or may each optionally be monosubstituted and the substituent is selected from the group consisting of cyano, methoxy, methoxycarbonyl and trifluoromethyl, where in total at most three of the substituents mentioned above are present, or $R^{5c}$ represents Y, Y represents the radical Y-2, $X^b$ represents fluorine, chlorine, bromine, cyano, methyl, ethyl, methoxy, ethoxy, methylthio, difluoromethyl or trifluoromethyl, m represents 0 or 1, $R^{13}$ and $R^{15}$ independently of one another represent hydrogen, or represent $C_1$-$C_4$-alkyl, cyclopropyl, cyclobutyl, cyclopentyl, cyclohexyl, oxanyl or 1,1-dioxothianyl, where the radicals mentioned above may each optionally be mono- to trisubstituted and the substituents independently of one another are selected from the group consisting of fluorine and chlorine, and/or may each optionally be monosubstituted and the substituent is selected from the group consisting of cyano, methyl, methoxy, trifluoromethyl, or $R^{13}$ and $R^{15}$ independently of one another represent cyclopropylmethyl or cyclobutylmethyl, or represent phenylmethyl or pyridylmethyl, where the radicals mentioned above may each optionally be mono- to trisubstituted and the substituents independently of one another are selected from the group consisting of fluorine and chlorine, and/or may each optionally be monosubstituted and the substituent is selected from the group consisting of cyano, methyl, methoxy, trifluoromethyl, where in total at most three of the substituents mentioned above are present, $R^{7a}$ represents hydrogen, $R^{7b}$ represents $C_1$-$C_4$-alkyl, cyclopropyl, benzyl or cyclopropylmethyl, where the radicals mentioned above may each optionally be mono- to trisubstituted and the substituents independently of one another are selected from the group consisting of fluorine and chlorine, or represents phenyl, pyridyl or pyrazolyl, where the radicals mentioned above may optionally be mono- to trisubstituted and the substituents independently of one another are selected from the group consisting of fluorine, chlorine and methyl, and/or may optionally be monosubstituted and the substituent is selected from the group consisting of cyano, methyl, methoxy, trifluoromethyl, methylthio, methylsulfinyl and methylsulfonyl, where in total at most three of the substituents mentioned above are present, and $R^{12}$ represents methyl, ethyl, n-propyl, isopropyl, n-butyl, isobutyl, sec-butyl, tert-butyl or phenyl, where the radicals mentioned above may each optionally be mono- to trisubstituted and the substituents independently of one another are selected from the group consisting of fluorine and chlorine.

4. The compound according to claim 1, having a structure according to formula (I-1)

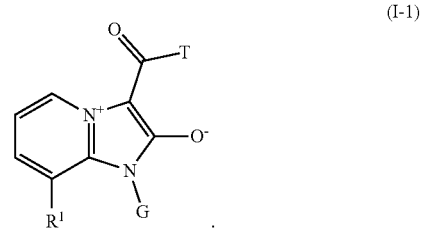

(I-1)

5. The compound according to claim 1, having a structure according to formula (I-1a)

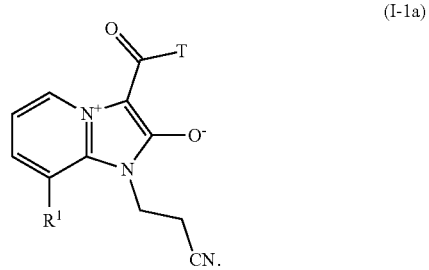

(I-1a)

6. The compound according to claim 1, having a structure according to formula (I-1b)

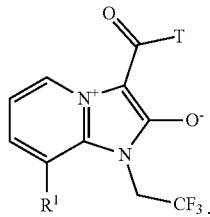

(I-1b)

7. A compound of formula (IV)

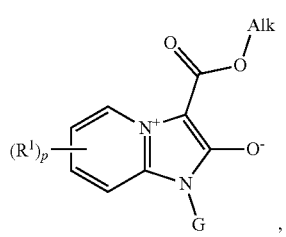

(IV)

in which
G represents $C_1$-$C_6$-alkyl or $C_2$-$C_6$-alkenyl, where the radicals mentioned above are each mono- to pentasubstituted by halogen and/or mono- to disubstituted by cyano, $C_1$-$C_4$-alkoxy, $C_1$-$C_4$-alkylcarbonyl, $C_1$-$C_4$-alkoxycarbonyl, $C_1$-$C_4$-carbonyl-$C_1$-$C_4$-alkoxy or $C_1$-$C_4$-alkoximino-$C_1$-$C_4$-alkyl,
$R^1$ in each case represents hydrogen, halogen, cyano, nitro, $SF_5$, SCN, amino, $C_1$-$C_6$-alkylamino, di-($C_1$-$C_6$)-alkylamino, hydroxy, COOH, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_3$-$C_6$-halocycloalkyl-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_2$-$C_6$-alkenyloxy, $C_3$-$C_6$-alkynyl, $C_3$-$C_6$-alkynyloxy, SH, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-haloalkylsulfinyl, $C_1$-$C_6$-haloalkylsulfonyl, $C_1$-$C_6$-alkylcarbonyl, $C_3$-$C_6$-cycloalkylcarbonyl, $C_1$-$C_6$-haloalkylcarbonyl, $C_1$-$C_6$-alkoxyimino-$C_1$-$C_6$-alkyl, $C_1$-$C_6$-alkoxycarbonyl, $C_1$-$C_6$-alkylaminocarbonyl, di-($C_1$-$C_6$)-alkylaminocarbonyl, aryl, hetaryl, aryl-$C_1$-$C_6$-alkyl or hetaryl-$C_1$-$C_6$-alkyl,
where aryl, hetaryl, aryl-$C_1$-$C_6$-alkyl and hetaryl-$C_1$-$C_6$-alkyl may each optionally be mono- or polysubstituted and the substituents independently of one another are selected from the group consisting of halogen, cyano, nitro, hydroxy, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkyl, $C_1$-$C_6$-haloalkoxy and $C_1$-$C_6$-alkylthio,
or
two radicals $R^1$ together form a 5- or 6-membered aliphatic, aromatic, heteroaromatic or heterocyclic ring which may optionally contain 1 to 2 atoms from the group consisting of O, S and N and which may optionally be mono- or polysubstituted, where the substituents independently of one another are selected from the group consisting of halogen and $C_1$-$C_4$-alkyl,
p represents 0, 1, 2 or 3, and
Alk represents $C_1$-$C_4$-alkyl, optionally methyl and ethyl.

8. A compound of formula (V)

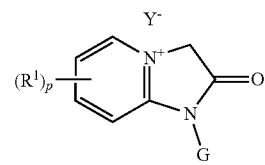

(V)

in which
G represents $C_1$-$C_6$-alkyl or $C_2$-$C_6$-alkenyl, where the radicals mentioned above are each mono- to pentasubstituted by halogen and/or mono- to disubstituted by cyano, $C_1$-$C_4$-alkoxy, $C_1$-$C_4$-alkylcarbonyl, $C_1$-$C_4$-alkoxycarbonyl, $C_1$-$C_4$-carbonyl-$C_1$-$C_4$-alkoxy or $C_1$-$C_4$-alkoximino-$C_1$-$C_4$-alkyl,
$R^1$ in each case represents hydrogen, halogen, cyano, nitro, $SF_5$, SCN, amino, $C_1$-$C_6$-alkylamino, di-($C_1$-$C_6$)-alkylamino, hydroxy, COOH, $C_1$-$C_6$-alkyl, $C_3$-$C_6$-cycloalkyl, $C_1$-$C_6$-haloalkyl, $C_1$-$C_6$-alkoxy, $C_1$-$C_6$-haloalkoxy, $C_3$-$C_6$-halocycloalkyl, $C_3$-$C_6$-halocycloalkyl-$C_1$-$C_6$-alkyl, $C_1$-$C_6$-alkoxy-$C_1$-$C_6$-alkyl, $C_1$-$C_6$-haloalkoxy-$C_1$-$C_6$-alkyl, $C_1$-$C_6$-alkoxy-$C_1$-$C_6$-alkyloxy, cyano-$C_1$-$C_6$-alkyl, $C_3$-$C_6$-cycloalkyl-$C_1$-$C_6$-alkyl, $C_2$-$C_6$-alkenyl, $C_2$-$C_6$-alkenyloxy, $C_3$-$C_6$-alkynyl, $C_3$-$C_6$-alkynyloxy, SH, $C_1$-$C_6$-alkylthio, $C_1$-$C_6$-alkylsulfinyl, $C_1$-$C_6$-alkylsulfonyl, $C_1$-$C_6$-haloalkylthio, $C_1$-$C_6$-haloalkylsulfinyl, $C_1$-$C_6$-haloalkylsulfonyl, $C_1$-$C_6$-alkylcarbonyl, $C_3$-$C_6$-cycloalkylcarbonyl, $C_1$-$C_6$-haloalkylcarbonyl, $C_1$-$C_6$-alkoxyimino-$C_1$-$C_6$-alkyl, $C_1$-$C_6$-alkoxycarbonyl, $C_1$-$C_6$-alkylaminocarbonyl, di-($C_1$-$C_6$)-alkylaminocarbonyl, aryl, hetaryl, aryl-$C_1$-$C_6$-alkyl or hetaryl-$C_1$-$C_6$-alkyl,
where aryl, hetaryl, aryl-$C_1$-$C_6$-alkyl and hetaryl-$C_1$-$C_6$-alkyl may each optionally be mono- or polysubstituted and the substituents independently of one another are selected from the group consisting of halogen, cyano, nitro, hydroxy, $C_1$-$C_6$-alkyl, $C_2$-$C_6$-alkenyl, $C_2$-$C_6$-alkynyl, $C_3$-$C_6$-cycloalkyl, $C_1$-$C_6$-alkoxy, $C_1$-$C_6$-haloalkyl, $C_1$-$C_6$-haloalkoxy and $C_1$-$C_6$-alkylthio,
or
two radicals $R^1$ together form a 5- or 6-membered aliphatic, aromatic, heteroaromatic or heterocyclic ring which may optionally contain 1 to 2 atoms from the group consisting of O, S and N and which may optionally be mono- or polysubstituted, where the substituents independently of one another are selected from the group consisting of halogen and $C_1$-$C_4$-alkyl,
p represents 0, 1, 2 or 3, and
Y represents $F^-$, $Cl^-$, $Br^-$, $I^-$, $NO_3^-$, $SO_4^-$, $ClO_4^-$ or $BF_4$.

9. A formulation, comprising at least one compound of the formula (I) according to claim 1.

10. The formulation according to claim 9, further comprising at least one extender and/or at least one surface-active substance.

11. The formulation according to claim 9, wherein the compound of the formula (I) is in a mixture with at least one further active compound.

12. A method for controlling one or more pests, optionally animal pests, comprising allowing a compound of formula (I) according to claim 1 or a formulation thereof to act on the pests and/or a habitat thereof.

13. The method according to claim 12, wherein the pest is an animal pest and comprises an insect, an arachnid or a nematode, or wherein the pest is an insect, an arachnid or a nematode.

14. A product comprising a compound of formula (I) according to claim 1 or a formulation thereof for controlling one or more animal pests.

15. The product according to claim 14, wherein the animal pest comprises an insect, an arachnid or a nematode, or the pest is an insect, an arachnid or a nematode.

16. The product according to claim 14 for use in crop protection.

17. The product according to claim 14 for use in the field of animal health.

18. A method for protecting seed or a germinating plant from one or more pests, optionally animal pests, comprising contacting seed with a compound of the formula (I) according to claim 1 or with a formulation thereof.

19. Seed obtained by a method according to claim 18.

* * * * *